US007790881B2

(12) United States Patent
Storey et al.

(10) Patent No.: US 7,790,881 B2
(45) Date of Patent: Sep. 7, 2010

(54) METHODS OF CHEMICAL SYNTHESIS AND PURIFICATION OF DIAMINOPHENOTHIAZINIUM COMPOUNDS INCLUDING METHYLTHIONINIUM CHLORIDE (MTC)

(75) Inventors: John Mervyn David Storey, Strathcarron (GB); James Peter Sinclair, Aberdeen (GB); Colin Marshall, Aberdeen (GB); Han Wan Tan, Singapore (SG)

(73) Assignee: Wista Laboratories Ltd., Singapore (SG)

( * ) Notice: Subject to any disclaimer, the term of this patent is extended or adjusted under 35 U.S.C. 154(b) by 598 days.

(21) Appl. No.: 11/575,845

(22) PCT Filed: Sep. 21, 2005

(86) PCT No.: PCT/GB2005/003634

§ 371 (c)(1),
(2), (4) Date: Nov. 9, 2007

(87) PCT Pub. No.: WO2006/032879

PCT Pub. Date: Mar. 30, 2006

(65) Prior Publication Data

US 2008/0207603 A1 Aug. 28, 2008

(30) Foreign Application Priority Data

Sep. 23, 2004 (GB) .................................. 0421234.6
Feb. 17, 2005 (GB) .................................. 0503343.6
Sep. 7, 2005 (WO) ............... PCT/GB2005/003441

(51) Int. Cl.
*C07D 279/20* (2006.01)
*A61K 31/5415* (2006.01)
(52) U.S. Cl. ................................ 544/35; 544/36; 544/37
(58) Field of Classification Search .................... 544/35, 544/36, 37
See application file for complete search history.

(56) References Cited

U.S. PATENT DOCUMENTS 6,953,794 B2  10/2005  Wischik et al.
2007/0191352 A1  8/2007  Wischik et al.

FOREIGN PATENT DOCUMENTS

| DE | 1 886 | 12/1877 |
|---|---|---|
| DE | 1886 | 12/1877 |
| EP | 0 510 668 | 4/1992 |
| GB | 2 373 787 | 10/2002 |
| WO | WO 96/30766 | 10/1996 |
| WO | WO 98/31219 | 7/1998 |
| WO | WO 01/96322 | 12/2001 |
| WO | WO 02/055720 | 7/2002 |

OTHER PUBLICATIONS

Bernthsen, A, 1885a, "Studien in der Methylenblaugruppe," Justus Liebig's Annalen der Chemie, Band 230, pp. 73-136 (in German with partial English translation).
Bernthsen, A, 1885b, "Studien in der Methylenblaugruppe," Justus Liebig's Annalen der Chemie, Band 230, pp. 137-211 (in German with partial English translation).
Bernthsen, A, 1889, "Studien in der Methylenblaugruppe," Justus Liebig's Annalen der Chemie, Band 251, pp. 1-96 (in German with partial English translation).
Bonneau, R., et al, 1967, "Purification des colorants thiaziniques, Azur A, Azur B, Azur C, par une méthode de partage", *Talanta*, vol. 14, pp. 121-122 (in French with English translation).
Braswell, E., 1968, "Evidence for trimerization in aqueous solutions of methylene blue", *Journal of Phys. Chem.*, vol. 72, pp. 2477-2483.
Colour Index, vol. 4 (3rd Edition, 1971), p. 4470, Entry No. 52015.
Fierz-David and Blangley, 1949, "F. oxazine and thiazine dyes", *Fundamental Processes of Dye Chemistry*, pp. 308-314.
Guttmann, P., et al, 1891, Über die Wirkung des Methylenblau bei Malaria. Berl Klin Wochenschr; vol. 28, pp. 953-956.
Kuban, V., et al, 1985, "Preparation of highly pure methylene blue compositions by an extraction procedure", *Chemicke Listy*, vol. 79, pp. 1200-1205 (in Russian with English abstract).
Leventis, N., et al., 1997, "Synthesis of substituted phenothiazines analogous to methylene blue by electrophilic and nucleophilic aromatic substitutions in tandem. A mechanistic perspective," *Tetrahedron*, vol. 53, pp. 10083-10092.

(Continued)

*Primary Examiner*—Kahsay T Habte
(74) *Attorney, Agent, or Firm*—Foley & Lardner LLP

(57) ABSTRACT

This invention pertains generally to the field of chemical synthesis and purification, and more specifically to methods of synthesizing and purifying certain 3,7 diamino-phenothiazin-5-ium compounds (referred to herein as "diaminophenothiazinium compounds") including Methylthioninium Chloride (MTC) (also known as Methylene Blue). In one embodiment, the method comprises the steps of, in order: nitrosylation (NOS); nitrosyl reduction (NR); thiosulfonic acid formation (TSAF); oxidative coupling (OC); Cr(VI) reduction (CR); isolation and purification of zwitterionic intermediate (IAPOZI); ring closure (RC); chloride salt formation (CSF); one of: sulphide treatment (ST); dimethyldithiocarbamate treatment (DT); carbonate treatment (CT); ethylenediaminetetraacetic acid treatment (EDTAT); organic extraction (OE); and recrystallisation (RX). The present invention also pertains to the resulting (high purity) compounds, compositions comprising them (e.g., tablets, capsules), and their use in methods of inactivating pathogens, and methods of medical treatment and diagnosis, etc., for example, for tauopathies, Alzheimer's disease (AD), skin cancer, melanoma, viral diseases, bacterial diseases, or protozoal diseases. Wherein: each of $R^1$ and $R^9$ is independently selected from: —H; $C_{1-4}$ alkenyl; and halogenated $C_{1-4}$ alkyl; each of $R^{3NA}$ and $R^{3NB}$ is independently selected from: $C_{1-4}$ alkyl; $C_{2-4}$ alkenyl; and halogenated $C_{4-1}$ alkyl; each of $R^{7NA}$ and $R^{7NB}$ is independently selected from: $C_{1-4}$ alkyl; $C_{2-4}$ alkenyl; and halogenated $C_{1-4}$ alkyl; and X is one or more anionic counter ions to achieve electrical neutrality.

60 Claims, No Drawings

OTHER PUBLICATIONS

Lillie, R.D., et al., 1979, "Zinc chloride methylene Blue, I. Biological stain history, physical characteristics and approximation of Azure B content of commercial samples," *Stain Technology*, vol. 54, No. 1, pp. 33-39.

Lohr, W., et al., 1975, "The azure dyes: their purification and physiochemical properties. Purification of Azure B," *Stain Technology*, vol. 50 (3), pp. 149-156.

Marshall, P.N., et al., 1975a, "The purification of Methylene Blue and Azure B by solvent extraction and crystallisation," *Stain Technology*, vol. 50(6), pp. 375-381.

Marshall, P.N., et al., 1975b, "Metal contaminants in commercial dye," *Stain Technology*, vol. 50 (3), pp. 143-147.

Michaelis, L., et al. 1940, "Semiquinone Radicals of the Thiazine," *Journal of the American Chemical Society*, vol. 62, pp. 204-211.

Rengelshausen, J., et al., 2004, "Pharmacokinetic interaction of chloroquine and methylene blue combination against malaria", *European Journal of Clinical Pharmacology*, vol. 60, pp. 709-715.

Schirmer, H., et al., 2003, "Methylene blue as an antimalarial agent", *Redox Report*, vol. 8, pp. 272-275.

International Search Report (ISR) and Written Opinion of the International Searching Authority (WOISA) for PCT/GB2005/003634. (22 pgs.), Apr. 18, 2006.

International Preliminary Report on Patentability (IPRP) for PCT/GB2005/003634. (12 pgs.), Apr. 18, 2006.

UK Search Report for GB 0421234.6, Mar. 27, 2007.

Bernthsen, A., "Studien in der Methylenblaugruppe", *Justus Liebig's Annalen der Chemie*, Band 230, (1885), pp. 73-136.

Bonneau, et al., "Purification des colorants thiaziniques, Azur A, Azur B, Azur C, par une méthode de partage", *Talanta*, vol. 14, (1967), pp. 121-122.

Braswell, E., "Evidence for trimerization in aqueous solutions of methylene blue", *Journal of Phys. Chem.*, vol. 72, (1968), pp. 2477-2483.

Colour Index, vol. 4, 3$^{rd}$ Ed., (1971), p. 4470, Entry No. 52015.

Fierz-David et al., "F. oxazine and thiazine dyes", *Fundamental Processes of Dye Chemistry*, (1949), pp. 308-314.

Guttmann, P., "Über die Wirkung des Methylenblau bei Malaria", *Berl Klin. Wochenschr*, vol. 28, (1891), pp. 953-956.

Kuban et al., "Preparation of highly pure methylene blue compositions by an extraction procedure", *Chemicke Listy*, vol. 79, (1985), pp. 1200-1205.

Leventis et al., "Synthesis of substituted phenothiazines analogous to methylene blue by electrophilic and nucleophilic aromatic substitutions in tandem. A mechanistic perspective", *Tetrahedron*, vol. 53, (1997), pp. 10083-10092.

Lillie et al., "Zinc chloride methylene blue, I. Biological stain history, physical characteristics and approximation of Azure B content of commercial samples", *Stain Technology*, vol. 54 (3), (1979), pp. 33-39.

Lohr et al., "The azure dyes: their purification and physiochemical properties. Purification of Azure B", *Stain Technology*, vol. 50 (3), (1975), pp. 149-156.

Marshall et al., "The purification of Methylene Blue and Azure B by solvent extraction and crystallization", *Stain Technology*, vol. 50 (6), (1975a), pp. 375-381.

Marshall et al., "Metal contaminants in commercial dyes", *Stain Technology*, vol. 50 (3), (1975b), pp. 143-147.

Michaelis et al., "Semiquinone Radicals of the Thiazines", *Journal of the American Chemical Society*, vol. 32, (1940), pp. 204-211.

Rengelshausen et al., "Pharmacokinetic interaction of chloroquine and methylene blue combination against malaria", *European Journal of Clinical Pharmacology*, vol. 60, (2004), pp. 709-715.

Schirmer et al., "Methylene blue as an antimalarial agent", *Redox Report*, vol. 8, (2003), pp. 272-275.

Search Report under Section 17 for Application No. GB0421234.6, Dated Jan. 20, 2005, 1 page.

International Search Report and Written Opinion of the International Searching Authority (WOISA) for International Application No. PCT/GB2005/003634, mailed Apr. 18, 2006, (22 pgs.).

International Preliminary Report on Patentability (IPRP) for International Application No. PCT/GB2005/003634, Mar. 27, 2007, (12 pgs.).

METHODS OF CHEMICAL SYNTHESIS AND PURIFICATION OF DIAMINOPHENOTHIAZINIUM COMPOUNDS INCLUDING METHYLTHIONINIUM CHLORIDE (MTC)

RELATED APPLICATIONS

This application is related to: United Kingdom patent application GB 0421234.6 filed 23 Sep. 2004; United Kingdom patent application GB 0503343.6 filed 17 Feb. 2005; International patent application PCT/GB2005/003441 filed 7 Sep. 2005, the contents of all of which are incorporated herein by reference in their entirety.

TECHNICAL FIELD

This invention pertains generally to the field of chemical synthesis and purification, and more specifically to methods of synthesizing and purifying certain 3,7-diaminophenothiazin-5-ium compounds (referred to herein as "diaminophenothiazinium compounds") including Methylthioninium Chloride (MTC) (also known as Methylene Blue). The present invention also pertains to the resulting (high purity) compounds, compositions comprising them (e.g., tablets, capsules), and their use in methods of inactivating pathogens, and methods of medical treatment and diagnosis, etc., for example, for tauopathies, Alzheimer's disease (AD), skin cancer, melanoma, viral diseases, bacterial diseases and protozoal diseases.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Methylthioninium Chloride (MTC) (also Known as Methylene Blue)

Methylthioninium Chloride (MTC) (also known as Methylene blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

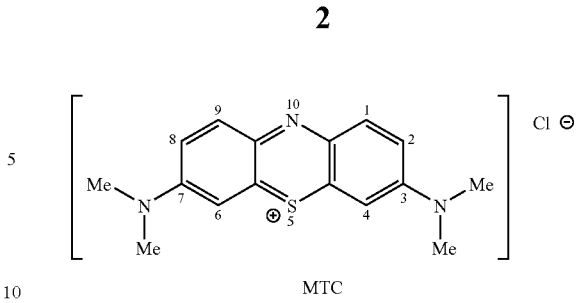

MTC

Methylthioninium Chloride (MTC) (also known as Methylene Blue), perhaps the most well known phenothiazine dye and redox indicator, has also been used as an optical probe of biophysical systems, as an intercalator in nanoporous materials, as a redox mediator, and in photoelectrochomic imaging.

See, for example, Colour Index (Vol. 4, 3rd edition, 1971) and Lillie et al., 1979, and references cited therein.

MTC was first described in a German Patent in 1877 (Badische Anilin-und Soda-Fabrik, 1877). In that patent, MTC was synthesized by nitrosylation of dimethylaniline, subsequent reduction to form N,N-dimethyl-1,4-diaminobenzene, and subsequent oxidative coupling in the presence of hydrogen sulphide ($H_2S$) and iron(III) chloride ($FeCl_3$).

Bernthsen described subsequent studies of MTC and methods for its synthesis (see Bernthsen, 1885a, 1885b, 1889).

Fierz-David and Blangley, 1949, also describes methods for the synthesis of MTC from dimethylaniline, as illustrated in the following scheme

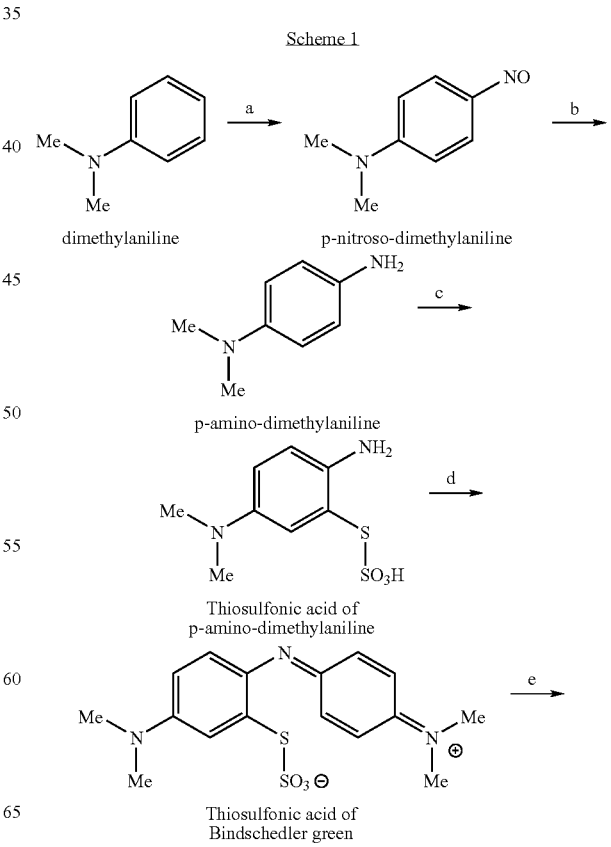

-continued

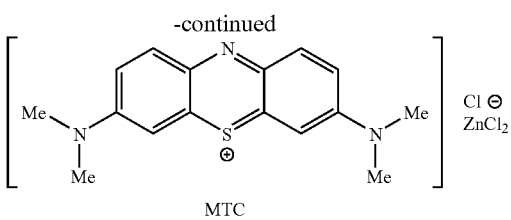

MTC

In step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline in aqueous acid (HCl) solution using zinc dust solution. In steps (c), (d), and (e), the p-aminodimethylaniline is oxidized in aqueous acid solution with another molecule of dimethylaniline, and simultaneously a thiosulfonic acid group is introduced; the ring is then closed using manganese dioxide or copper sulfate. More specifically, a clear neutral solution of p-aminodimethylaniline is acidified ($H_2SO_4$), and a non-reducing zinc chloride solution is added ($ZnCl_2$ with $Na_2Cr_2O_7$). Aluminium thiosulfate ($Al_2(S_2O_3)_3$) and sodium thiosulfate ($Na_2S_2O_3$) are added. Sodium dichromate ($Na_2Cr_2O_7$) is added. The mixture is heated and aerated. Dimethylaniline is added. Sodium dichromate ($Na_2Cr_2O_7$) is added. The mixture is heated, and becomes dark greenish-blue in colour due to the formation of the thiosulfonic acid of Bindschedler green. Manganese dioxide or copper sulfate is added, and the mixture heated, and the dye precipitates from the concentrated zinc chloride solution.

Very similar synthesis methods are described in the Colour Index (Vol. 4, 3rd edition, 1971), p. 4470.

Masuya et al., 1992, describe certain phenothiazine derivatives, and methods for their preparation and use in photodynamic therapy of cancer and in immunoassays utilizing chemiluminescence. The compounds are prepared by routes similar to those discussed above.

Leventis et al., 1997, describe methods for the synthesis of certain MTC analogs, which employ phenothiazine as a starting material and which add the desired 3,7-substituents by halogenation followed by amination. The authors assert that MTC is synthesized commercially by oxidation of N,N-dimethyl-p-phenylene diamine with $Na_2Cr_2O_7$ in the presence of $Na_2S_2O_3$, followed by further oxidation in the presence of N,N-dimethylamine.

Marshall and Lewis, 1975a, describes the purification of commercial MTC and Azure B by solvent extraction and crystallisation. They assert that aqueous MTC/Azure B mixtures at a buffered pH of 9.5 can be separated by extraction with carbon tetrachloride. The carbon tetrachloride removes the Azure B while leaving the MTC in the aqueous layer. They further assert that low temperature crystallisation of MTC at a concentration of 0.25 N with hydrochloric acid removes metal contaminants. However, the organic purity analysis reported therein is based on thin-layer chromatography, which is not suitable for quantification. Also, the microanalysis for sulphated ash does not indicate a metal free sample. (The preferred technique in 1975 was atomic absorption.)

Marshall and Lewis, 1975b, describes the analysis of metal contaminants in commercial thiazine dyes by atomic absorption spectrophotometry. They report 38 samples with metal concentrations that vary widely between 0.02% and 25.35% of individual samples; the metals examined were iron, potassium, sodium and zinc. They also report that other metals may be present which were not analysed. Aluminium, chromium, manganese, and copper, are all involved in synthetic procedures for MTC and are almost certain to be present. Importantly, they report large variations in the metal content of commercial samples of MTC.

Lohr et al., 1975, describes the purification of Azure B by column chromatography, specifically by separation to isolate the desired product followed by ion exchange back to the chloride. They assert that other cationic dyes such as MTC can be purified by this method. However, column chromatography is not a suitable method for the purification of MTC on a large scale.

Fierz-David et al., 1949, describes the synthesis of the zinc chloride double salt of MTC and the removal of zinc by chelation with sodium carbonate followed by filtration to generate zinc free methylene blue. However, the authors acknowledge that this technique cannot be used on a large scale, because the yields are poor.

MTC is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria either singly (Guttmann & Ehrlich, 1891) or in combination with chloroquine (Schirmer et al. 2003; Rengelhausen et al. 2004). Malaria in humans is caused by one of four protozoan species of the genus *Plasmodium*: *P. falciparum*, *P. vivax*, *P. ovale*, or *P. malariae*. All species are transmitted by the bite of an infected female *Anopheles* mosquito. Occasionally, transmission occurs by blood transfusion, organ transplantation, needle-sharing, or congenitally from mother to fetus. Malaria causes 300-500 million infections worldwide and approximately 1 million deaths annually. Drug resistance, however is a major concern and is greatest for *P. falciparum*, the species that accounts for almost all malaria-related deaths. Drugs or drug combinations that are currently recommended for prophylaxis of malaria include chloroquine/proguanil hydrochloride, mefloquine, doxycycline and primaquine.

MTC (under the name Virostat, from Bioenvision Inc., New York) has shown potent viricidal activity in vitro. Specifically Virostat is effective against viruses such as HIV and West Nile Virus in laboratory tests. West Nile virus (WNV) is a potentially serious illness affecting the central nervous system. The large majority of infected people will show no visible symptoms or mild flu-like symptoms such as fever and headache. About one in 150 will develop severe symptoms including tremors, convulsions, muscle weakness, vision loss, numbness, paralysis or coma. Generally, WNV is spread by the bite of an infected mosquito, but can also spread through blood transfusions, organ transplants, breastfeeding or during pregnancy from mother to child. Virostat is also currently in clinical trials for the treatment of chronic Hepatitis C. Hepatitis C is a viral infection of the liver. The virus, HCV, is a major cause of acute hepatitis and chronic liver disease, including cirrhosis and liver cancer. HCV is spread primarily by direct contact with human blood. The major causes of HCV infection worldwide are use of unscreened blood transfusions, and re-use of needles and syringes that have not been adequately sterilized. The World Health Organization has declared hepatitis C a global health problem, with approximately 3% of the world's population infected with HCV and it varies considerably by region. The prevalence in the US is estimated at 1.3% or approximately 3.5 million people. Egypt has a population of approximately 62 million and contains the highest prevalence of hepatitis C in the world, estimated at over 20% of the nation's approximately 62 million people.

MTC, when combined with light, can prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compounds then bind to the nucleic acid of the viral or bacterial pathogen, preventing replication of the DNA or RNA. Because MTC designed to inactivate pathogens, it has the potential to reduce the risk of transmission of pathogens that would remain undetected by testing.

MTC and derivatives thereof (e.g., "diaminophenothiazinium compounds") have been found to be useful in the treatment of tauopathies (such as, for example, Alzheimer's disease) (see, for example, Wischik, C. M., et al., 1996, 2002).

Oral and parenteral formulations of MTC are commercially available in the United States, usually under the name Urolene Blue®. However, these formulations contain substantial amounts of metal impurities. These impurities are highly undesirable, and many (e.g., including Al, Cr, Fe, Cu) exceed the safety limits set by European health agencies.

Consequently, there is a great need for higher purity (e.g., pharmaceutical grade purity, e.g., a purity safe for human consumption, e.g., with low or reduced metal content) diaminophenothiazinium compounds, including MTC.

The inventors have developed methods for the synthesis of diaminophenothiazinium compounds (including MTC), that yield products with extremely high purity and in particular, products with extremely low levels of undesired impurities (both organic and metal) that meet (and often exceed) the safety limits set by European health agencies (e.g., the European Pharmacopoeia).

Without exaggeration, MTC prepared by the methods described herein is the purest available worldwide.

SUMMARY OF THE INVENTION

One aspect of the present invention pertains to a method of synthesis of diaminophenothiazinium compounds, including high purity diaminophenothiazinium compounds.

Another aspect of the present invention pertains to a method of purification of diaminophenothiazinium compounds.

Another aspect of the invention pertains to a high purity diaminophenothiazinium compound which is obtained by, or obtainable by, a method as described herein.

Another aspect of the invention pertains to a composition (e.g., a pharmaceutical composition, e.g., a tablet, a capsule) comprising a high purity diaminophenothiazinium compound as described herein.

Another aspect of the invention pertains to a high purity diaminophenothiazinium compound as described herein for use in a method of treatment of the human or animal body by therapy, for example in respect of any of the diseases or indications discussed herein.

Another aspect of the invention pertains to a high purity diaminophenothiazinium compound as described herein for use in a method of inactivating pathogens.

Another aspect of the invention pertains to use of a high purity diaminophenothiazinium compound as described herein for the manufacture of a medicament for use in the treatment of, e.g., a tauopathy (e.g., Alzheimer's disease).

Another aspect of the invention pertains to use of a method of synthesis of a high purity diaminophenothiazinium compound, as described herein, as part of a method of manufacturing a medicament for use in the treatment of, e.g., a tauopathy (e.g., Alzheimer's disease).

Another aspect of the invention pertains to a method of treatment of, e.g., a tauopathy (e.g., Alzheimer's disease) in a patient, comprising administering to said patient a therapeutically-effective amount of a high purity diaminophenothiazinium compound, as described herein.

As will be appreciated by one of skill in the art, features and preferred embodiments of one aspect of the invention will also pertain to other aspects of the invention.

DETAILED DESCRIPTION

The Compounds

In general, the present invention pertains to methods for the preparation of certain 3,7-diamino-phenothiazin-5-ium compounds of the following formula, collectively referred to herein as "diaminophenothiazinium compounds":

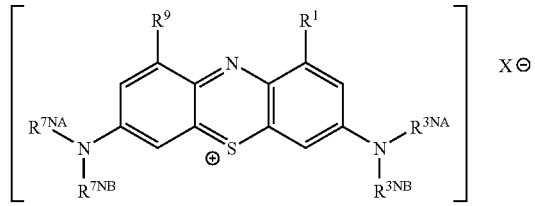

wherein:
each of $R^1$ and $R^9$ is independently selected from: —H; $C_{1-4}$alkyl; $C_{2-4}$alkenyl; and halogenated $C_{1-4}$alkyl;
each of $R^{3NA}$ and $R^{3NB}$ is independently selected from: $C_{1-4}$alkyl; $C_{2-4}$alkenyl; and halogenated $C_{1-4}$alkyl;
each of $R^{7NA}$ and $R^{7NB}$ is independently selected from: $C_{1-4}$alkyl; $C_{2-4}$alkenyl; and halogenated $C_{1-4}$alkyl; and
X is one or more anionic counter ions to achieve electrical neutrality.

The above structure is only one of many equivalent resonance structures, some of which are shown below, and all of which are intended to be encompassed by the above structure:

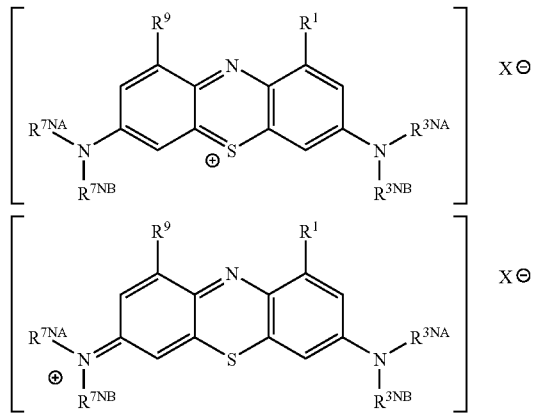

-continued

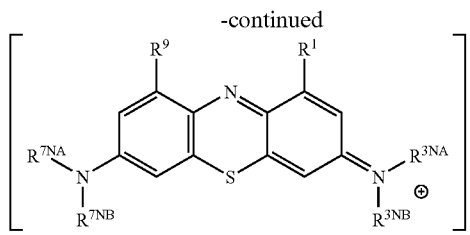

In one embodiment, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{1-4}$alkenyl groups, such as —CH=CH$_2$ (vinyl) and —CH$_2$—CH=CH$_2$ (allyl).

In one embodiment, the halogenated $C_{1-4}$alkyl groups are selected from: —CF$_3$, —CH$_2$CF$_3$, and —CF$_2$CF$_3$.

In one embodiment, each of $R^1$ and $R^9$ is independently —H, -Me, -Et, or —CF$_3$.

In one embodiment, each of $R^1$ and $R^9$ is independently —H, -Me, or -Et.

In one embodiment, each of $R^1$ and $R^9$ is independently —H.

In one embodiment, each of $R^1$ and $R^9$ is independently -Me.

In one embodiment, each of $R^1$ and $R^9$ is independently -Et.

In one embodiment, $R^1$ and $R^9$ are the same.

In one embodiment, $R^1$ and $R^9$ are different.

In one embodiment, each of $R^{3NA}$ and $R^{3NB}$ independently -Me, -Et, -nPr, -nBu, —CH$_2$—CH=CH$_2$, or —CF$_3$.

In one embodiment, each of $R^{3NA}$ and $R^{3NB}$ is independently -Me or -Et.

In one embodiment, each of $R^{3NA}$ and $R^{3NB}$ is independently -Me.

In one embodiment, each of $R^{3NA}$ and $R^{3NB}$ is independently -Et.

In one embodiment, $R^{3NA}$ and $R^{3NB}$ are the same.

In one embodiment, $R^{3NA}$ and $R^{3NB}$ are different.

In one embodiment, each of $R^{7NA}$ and $R^{7NB}$ independently -Me, -Et, -nPr, -nBu, —CH$_2$—CH=CH$_2$, or —CF$_3$.

In one embodiment, each of $R^{7NA}$ and $R^{7NB}$ is independently -Me or -Et.

In one embodiment, each of $R^{7NA}$ and $R^{7NB}$ is independently -Me.

In one embodiment, each of $R^{7NA}$ and $R^{7NB}$ is independently -Et.

In one embodiment, $R^{7NA}$ and $R^{7NB}$ are the same.

In one embodiment, $R^{7NA}$ and $R^{7NB}$ are different.

In one embodiment, $R^{3NA}$ and $R^{3NB}$ and $R^{7NA}$ and $R^{7NB}$ are the same.

In one embodiment, the groups —N($R^{3NA}$)($R^{3NB}$) and —N($R^{7NA}$)($R^{7NB}$) are the same.

In one embodiment, the groups —N($R^{3NA}$)($R^{3NB}$) and —N($R^{7NA}$)($R^{7NB}$) are the same, and are selected from: —NMe$_2$, —NEt$_2$, —N(nPr)$_2$, —N(Bu)$_2$, —NMeEt, —NMe(nPr), and —N(CH$_2$CH=CH$_2$)$_2$.

In one embodiment, the groups —N($R^{3NA}$)($R^{3NB}$) and —N($R^{7NA}$)($R^{7NB}$) are the same, and are selected from: —NMe$_2$ and —NEt$_2$.

In one embodiment, the groups —N($R^{3NA}$)($R^{3NB}$) and —N($R^{7NA}$)($R^{7NB}$) are other than —NMe$_2$.

In one embodiment, one or more of the carbon atoms is $^{11}$C or $^{13}$C.

In one embodiment, one or more of the carbon atoms is $^{11}$C.

In one embodiment, one or more of the carbon atoms is $^{13}$C.

In one embodiment, one or more of the nitrogen atoms is $^{15}$N.

In one embodiment, one or more or all of the carbon atoms of one or more or all of the groups $R^{3NA}$, $R^{3NB}$, $R^{7NA}$ and $R^{7NB}$ is $^{13}$C.

In one embodiment, each of the groups —N($R^{3NA}$)($R^{3NB}$) and —N($R^{7NA}$)($R^{7NB}$) is —N($^{13}$CH$_3$)$_2$.

In one embodiment, each of $R^1$ and $R^9$ is —H, and each of the groups —N($R^{3NA}$)($R^{3NB}$) and —N($R^{7NA}$)($R^{7NB}$) is —N($^{13}$CH$_3$)$_2$.

In one embodiment, each of $R^1$ and $R^9$ is —H; each of the groups —N($R^{3NA}$)($R^{3NB}$) and N($R^{7NA}$)($R^{7NB}$) is —N($^{13}$CH$_3$)$_2$; and X$^-$ is Cl$^-$.

In one embodiment, X$^-$ is independently a halogen anion (i.e., halide).

In one embodiment, X$^-$ is independently Cl$^-$, Br$^-$, or I$^-$.

In one embodiment, X$^-$ is independently Cl$^-$.

In one embodiment, the compound is in the form of a mixed salt, for example, a ZnCl$_2$ mixed salt.

Examples of such compounds include the following:

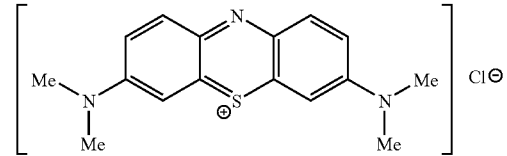

MTC
(Methylene Blue)

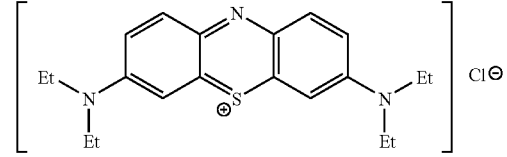

ETC

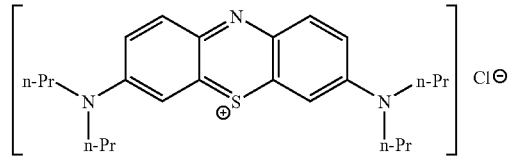

PTC

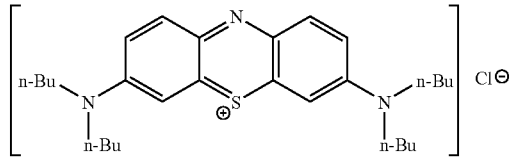

BTC

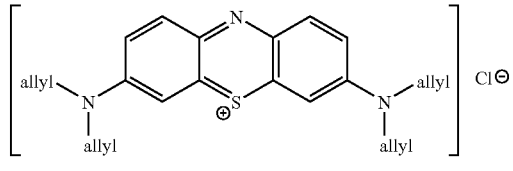

ATC

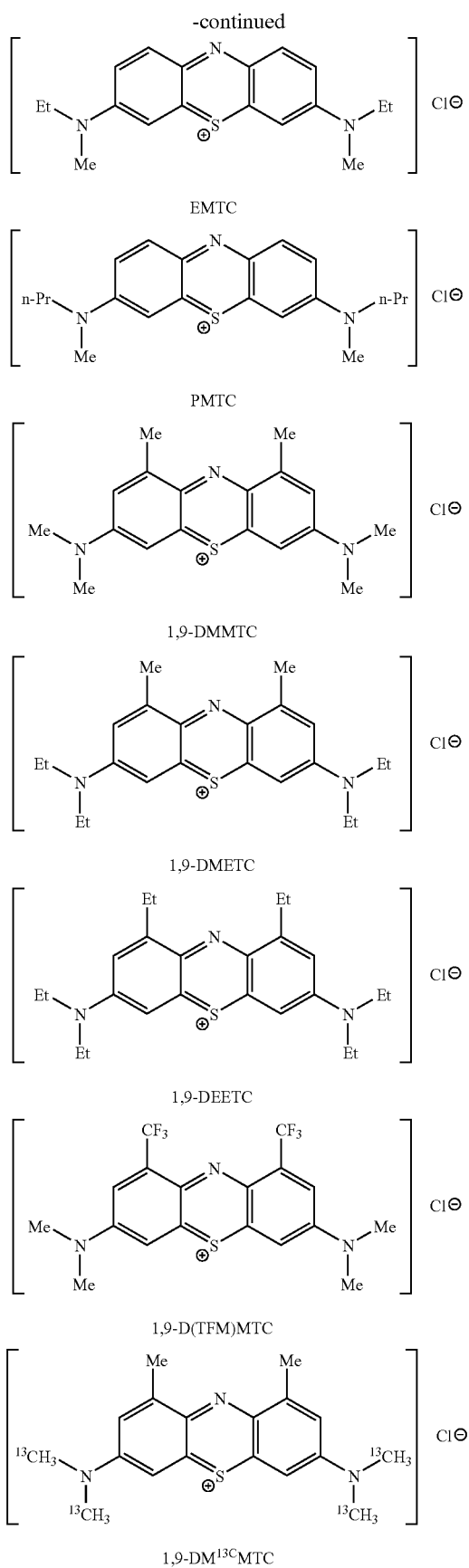
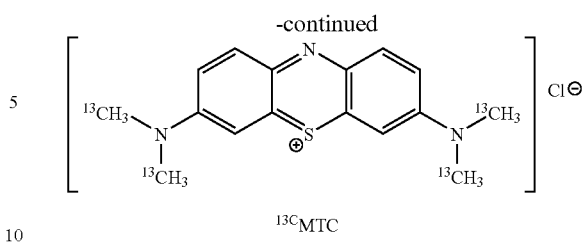

Synthesis Method A

One important difference between known methods and the presently claimed Method A is the step of isolation and purification of the zwitterionic intermediate, 6 (IAPOZI). This step of isolation and purification gives rise to improved yield in the subsequent ring closure step (due to, inter alia, improved stability of the zwitterionic intermediate and reduced side reactions), as well as improved purity of the final diaminophenothiazinium compound. In conventional methods, the zwitterionic intermediate is not isolated, and the reaction mixture is used, unchanged, in the subsequent step.

Another important difference between known methods and the presently claimed Method A is the step of Cr(VI) reduction. Cr(VI) is used (at least) in the oxidative coupling step. Residual Cr(VI) presents several serious problems. First, high levels of highly toxic contaminants such as residual Cr(VI) are unacceptable in products destined for use in pharmacy. By reducing residual Cr(VI) to Cr(III), which is a much less toxic form, pharmaceutical standards can more easily be satisfied. Second, residual Cr(VI) destabilizes the zwitterionic intermediate and impedes the subsequent ring closure (RC) step, and thus reduces the yield of the final diaminophenothiazinium compound. By reducing residual Cr(VI) to Cr(III), the yield of the final diaminophenothiazinium compound is greatly increased.

In addition, chromium can more easily be removed when in the form of Cr(III) than when in the form of Cr(VI). By reducing residual Cr(VI) to Cr(III), it is possible to obtain a product with very low levels of residual chromium.

Another important difference between known methods and the presently claimed Method A is the treatment step, that is, treatment of the chloride salt with one or more of sulphide (ST), dimethyldithiocarbamate (DT), carbonate (CT), ethylenediaminetetraacetic acid (EDTAT), or an organic solvent (OE). This additional step (or these additional steps) greatly improves the purity of the diaminophenothiazinium compound.

In one embodiment, the method of synthesis comprises the steps of, in order:

oxidative coupling (OC);
isolation and purification of zwitterionic intermediate (IAPOZI);
ring closure (RC).

In one embodiment, the method of synthesis comprises the steps of, in order:

oxidative coupling (OC);
Cr(VI) reduction (CR);
isolation and purification of zwitterionic intermediate (IAPOZI);
ring closure (RC).

In one embodiment, the method of synthesis additionally comprises the initial step of:

thiosulfonic acid formation (TSAF).

In one embodiment, the method of synthesis additionally comprises the initial steps of:
nitrosyl reduction (NR);
thiosulfonic acid formation (TSAF);
In one embodiment, the method of synthesis additionally comprises the initial steps of:
nitrosylation (NOS);
nitrosyl reduction (NR);
thiosulfonic acid formation (TSAF);
In one embodiment, the method of synthesis additionally comprises the subsequent step of:
chloride salt formation (CSF).
In one embodiment, the method of synthesis additionally comprises a subsequent step selected from:
sulphide treatment (ST);
dimethyldithiocarbamate treatment (DT);
carbonate treatment (CT); and
ethylenediaminetetraacetic acid treatment (EDTAT).
In one embodiment, the method of synthesis additionally comprises a subsequent step selected from:
sulphide treatment (ST);
dimethyldithiocarbamate treatment (DT);
carbonate treatment (CT);
ethylenediaminetetraacetic acid treatment (EDTAT); and
organic extraction (OE).
In one embodiment, the method of synthesis additionally comprises a subsequent step selected from:
sulphide treatment (ST);
dimethyldithiocarbamate treatment (DT);
carbonate treatment (CT); and
ethylenediaminetetraacetic acid treatment (EDTAT);

followed by the subsequent step of:
organic extraction (OE).
In one embodiment, the method of synthesis additionally comprises a subsequent step selected from:
sulphide treatment (ST);

followed by the subsequent step of:
organic extraction (OE).
In one embodiment, the method of synthesis additionally comprises the subsequent step of:
organic extraction (OE).
In one embodiment, the method of synthesis additionally comprises the subsequent step of:
recrystallisation (RX).
Thus, in one embodiment, the method of synthesis comprises the steps of, in order:
nitrosylation (NOS);
nitrosyl reduction (NR);
thiosulfonic acid formation (TSAF);
oxidative coupling (OC);
Cr(VI) reduction (CR);
isolation and purification of zwitterionic intermediate (IAPOZI);
ring closure (RC);
chloride salt formation (CSF);
one or more of:
sulphide treatment (ST);
dimethyldithiocarbamate treatment (DT);
carbonate treatment (CT); and
ethylenediaminetetraacetic acid treatment (EDTAT);
organic extraction (OE);
recrystallisation (RX).
In one embodiment, the method of synthesis is a 2-pot method.
In one embodiment, the method of synthesis is a 3-pot method.

These methods are well suited for the synthesis of diaminophenothiazinium compounds wherein $R^1$ and $R^9$ are —H.

These methods are especially well suited for the synthesis of Methylthioninium Chloride (MTC) (also known as Methylene Blue).

Purification Methods

Another aspect of the present invention pertains to methods of purification of certain 3,7-diamino-phenothiazin-5-ium compounds, specifically, the "diaminophenothiazinium compounds" described above under the heading "The Compounds".

In one embodiment, the method of purification is a method of purification of MTC.

In one embodiment, the method of purification is applied to a diaminophenothiazinium compound (e.g., MTC) in general, that is, that may or may not have been prepared by a method of synthesis as described herein.

For example, the method of purification may be applied to a commercially available diaminophenothiazinium compound (e.g., MTC), e.g., that is relatively impure or that contains undesirable or unacceptably high levels of certain impurities (e.g., organic impurities, metals, etc.).

For example, In one embodiment the method of purification is applied to commercially available Medex™ (e.g., to MTC initially provided by Medex Medical Export Co. Ltd.)

For example, In one embodiment the method of purification is applied to commercially available Urolene Blue® (e.g., to MTC initially provided as Urolene Blue®).

In one embodiment, the method of purification is applied to a diaminophenothiazinium compound (e.g., MTC) that has been prepared by a method of synthesis as described herein (e.g., to MTC initially provided as the product of a method of synthesis as described herein.

In one embodiment, the method of purification comprises one or more steps, in order, selected from:
recrystallisation (RX);
organic extraction (OE);
recrystallisation (RX);
a treatment step, selected from:
sulphide treatment (ST);
dimethyldithiocarbamate treatment (DT);
carbonate treatment (CT); and
ethylenediaminetetraacetic acid treatment (EDTAT);
recrystallisation (RX);
organic extraction (OE); and
recrystallisation (RX).

In one embodiment, the method of purification comprises a step of:
a treatment step, selected from:
sulphide treatment (ST);
dimethyldithiocarbamate treatment (DT);
carbonate treatment (CT); and
ethylenediaminetetraacetic acid treatment (EDTAT).

In one embodiment, the method of purification additionally comprises a step of:
a treatment step, selected from:
sulphide treatment (ST);
dimethyldithiocarbamate treatment (DT);
carbonate treatment (CT); and
ethylenediaminetetraacetic acid treatment (EDTAT).

In one embodiment, the method of purification comprises a step of:
sulphide treatment (ST).

In one embodiment, the method of purification additionally comprises a step of:
sulphide treatment (ST).

In one embodiment, the method of purification comprises a step of:
organic extraction (OE).

In one embodiment, the method of purification additionally comprises a step of:
organic extraction (OE).

In one embodiment, the method of purification comprises a step of:
recrystallisation (RX).

In one embodiment, the method of purification additionally comprises a step of:
recrystallisation (RX).

In one embodiment, the method of purification comprises the steps of, in order:
a treatment step, selected from:
sulphide treatment (ST);
dimethyldithiocarbamate treatment (DT),
carbonate treatment (CT); and
ethylenediaminetetraacetic acid treatment (EDTAT); and
organic extraction (OE).

In one embodiment, the method of purification comprises the steps of, in order:
sulphide treatment (ST); and
organic extraction (OE).

In one embodiment, the method of purification comprises the steps of, in order:
a treatment step, selected from:
sulphide treatment (ST);
dimethyldithiocarbamate treatment (DT);
carbonate treatment (CT); and
ethylenediaminetetraacetic acid treatment (EDTAT); and
recrystallisation (RX).

In one embodiment, the method of purification comprises the steps of, in order:
sulphide treatment (ST); and
recrystallisation (RX).

In one embodiment, the method of purification comprises the steps of, in order:
organic extraction (OE); and
recrystallisation (RX).

In one embodiment, the method of purification comprises the steps of, in order:
a treatment step, selected from:
sulphide treatment (ST);
dimethyldithiocarbamate treatment (DT);
carbonate treatment (CT); and
ethylenediaminetetraacetic acid treatment (EDTAT);
organic extraction (OE); and
recrystallisation (RX).

In one embodiment, the method of purification comprises the steps of, in order:
sulphide treatment (ST);
organic extraction (OE); and
recrystallisation (RX).

In one embodiment, the method of purification comprises the steps of, in order:
recrystallisation (RX); and
a treatment step, selected from:
sulphide treatment (ST);
dimethyldithiocarbamate treatment (DT);
carbonate treatment (CT); and
ethylenediaminetetraacetic acid treatment (EDTAT).

In one embodiment, the method of purification comprises the steps of, in order:
recrystallisation (RX); and
sulphide treatment (ST).

In one embodiment, the method of purification comprises the steps of, in order:
recrystallisation (RX); and
organic extraction (OE).

In one embodiment, the method of purification comprises the steps of, in order:
recrystallisation (RX);
a treatment step, selected from:
sulphide treatment (ST);
dimethyldithiocarbamate treatment (DT);
carbonate treatment (CT); and
ethylenediaminetetraacetic acid treatment (EDTAT); and
organic extraction (OE).

In one embodiment, the method of purification comprises the steps of, in order:
recrystallisation (RX);
sulphide treatment (ST); and
organic extraction (OE).

In one embodiment, the method of purification comprises the steps of, in order:
a treatment step, selected from:
sulphide treatment (ST);
dimethyldithiocarbamate treatment (DT);
carbonate treatment (CT); and
ethylenediaminetetraacetic acid treatment (EDTAT);
recrystallisation (RX); and
organic extraction (OE).

In one embodiment, the method of purification comprises the steps of, in order:
sulphide treatment (ST);
recrystallisation (RX); and
organic extraction (OE).

In one embodiment, the organic extraction (OE) employs dichloromethane (DCM, $CH_2Cl_2$).

In one embodiment, the recrystallisation (RX) step is a cool acidic recrystallisation (RX-CAR) step.

Nitrosylation (NOS)

In this step, an N,N-disubstituted-3-optionally substituted aniline, 1, is 4-nitrosylated to give an N,N-disubstituted-3-optionally substituted-4-nitrosyl aniline, 2, as illustrated in the following scheme:

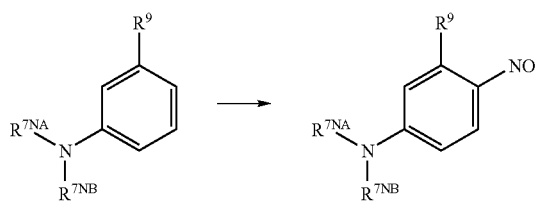

In one embodiment, an N,N-dimethyl aniline, 1', is 4-nitrosylated to give an N,N-dimethyl-4-nitrosyl aniline, 2', as illustrated in the following scheme:

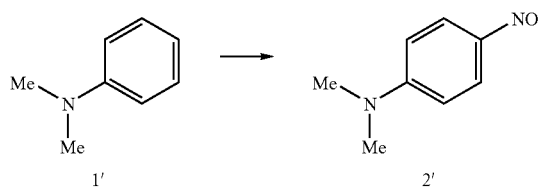

In one embodiment, the nitrosylation is performed using a nitrite.

In one embodiment, the nitrite is or comprises $NO_2^-$.

In one embodiment, the nitrite is or comprises alkali metal nitrite.

In one embodiment, the nitrite is or comprises sodium nitrite or potassium nitrite.

In one embodiment, the nitrite is sodium nitrite ($NaNO_2$).

In one embodiment, the molar ratio of nitrite to aniline, 1, is 0.8 to 1.5.

In one embodiment, the molar ratio is 1.0 to 1.5.

In one embodiment, the molar ratio is 1.1 to 1.5.

In one embodiment, the molar ratio is 1.1 to 1.3.

In one embodiment, the nitrosylation is performed under acidic conditions.

In one embodiment, the nitrosylation is performed at a pH of 1 or less.

In one embodiment, the nitrosylation is performed at a pH of 1 to −1.

In one embodiment, the nitrosylation is performed at a pH of 1 to 0.

(Unless otherwise specified, all pH values are measured at room temperature.)

In one embodiment, the acidic conditions are obtained using a strong acid.

In one embodiment, the acidic conditions are obtained using HCl (which has one strong acid proton).

In one embodiment, the molar ratio of acid protons to aniline, 1, is 1 to 4.

In one embodiment, the range is 2 to 4.

In one embodiment, the range is 3 to 4.

In one embodiment, the ratio is about 3.2.

In one embodiment, the range is 2 to 3.

In one embodiment, the range is 2.25 to 2.75.

In one embodiment, the ratio is about 2.5.

In one embodiment, the reaction is performed in an aqueous medium.

In one embodiment, the reaction temperature is 2 to 25° C.

In one embodiment, the reaction temperature is 2 to 15° C.

In one embodiment, the reaction temperature is 2 to 10° C.

In one embodiment, the reaction temperature is about 5° C.

In one embodiment, the reaction time is 10 to 240 minutes.

In one embodiment, the reaction time is 30 to 120 minutes.

In one embodiment, the reaction time is about 60 minutes.

In one embodiment, the reaction mixture is stirred during the reaction step.

Nitrosyl Reduction (NR)

In this step, an N,N-disubstituted-3-optionally substituted-4-nitrosyl aniline, 2, is reduced to form a N,N-disubstituted-1,4-diamino-5-optionally substituted benzene, 3, as illustrated in the following scheme:

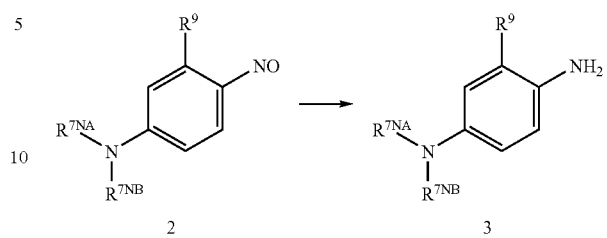

In one embodiment, an N,N-dimethyl-4-nitrosyl aniline, 2', is reduced to form a N,N-dimethyl-1,4-diamino-benzene, 3', as illustrated in the following scheme:

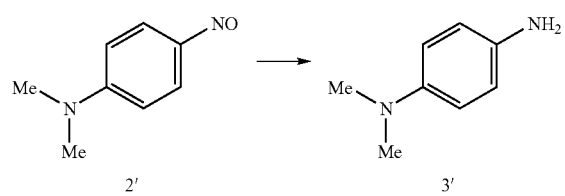

In one embodiment, the reduction is by reaction with a reducing agent.

In one embodiment, the reducing agent is or comprises Fe(0).

In one embodiment, the reducing agent is or comprises metallic iron.

In one embodiment, the reducing agent is metallic iron.

Metallic iron may be obtained commercially, for example, as metal filings.

In one embodiment, the molar ratio of Fe(0) to aniline, 1, is 1.0 to 4.0.

In one embodiment, the range is 1.5 to 4.0.

In one embodiment, the range is 1.5 to 3.0.

In one embodiment, the range is 1.5 to 2.5.

In one embodiment, the range is 1.5 to 3.5.

In one embodiment, the range is 2.0 to 3.0.

In one embodiment, the ratio is about 2.4.

In one embodiment, the reaction is performed under acidic conditions.

In one embodiment, the reaction is performed at a pH of 1 or less.

In one embodiment, the reaction is performed at a pH of 1 to −1.

In one embodiment, the reaction is performed at a pH of 1 to 0.

In one embodiment, the acidic conditions are obtained using a strong acid.

In one embodiment, the acidic conditions are obtained using HCl (which has one strong acid proton).

In one embodiment, the molar ratio of acid protons to aniline, 1, is 1 to 4.

In one embodiment, the range is 2 to 4.

In one embodiment, the range is 3 to 4.

In one embodiment, the ratio is about 3.2.

In one embodiment, the range is 2 to 3.

In one embodiment, the range is 2.25 to 2.75.

In one embodiment, the ratio is about 2.5

In one embodiment, the reaction is performed in an aqueous medium.

In one embodiment, the reaction is performed at a temperature of 2 to 35° C.

In one embodiment, the reaction is performed at a temperature of 10 to 30° C.

In one embodiment, the reaction is performed at a temperature of about 10° C.

In one embodiment, the reaction is performed for a time of 10 to 240 minutes.

In one embodiment, the reaction is performed for a time of 30 to 180 minutes.

In one embodiment, the reaction is performed for a time of about 120 minutes.

In one embodiment, the reaction mixture is stirred during the reaction step.

In one embodiment, when the reducing agent is metallic iron, excess metallic iron is removed from the reaction mixture after reaction completion, for example, by filtration.

Thiosulfonic Acid Formation (TSAF)

In this step, an N,N-disubstituted-1,4-diamino-5-optionally substituted benzene, 3, is oxidized in the presence of a thiosulfate to give a thiosulfuric acid S-{2-(amino)-3-(optionally substituted)-5-(disubstituted-amino)-phenyl}ester, 4, as illustrated in the following scheme:

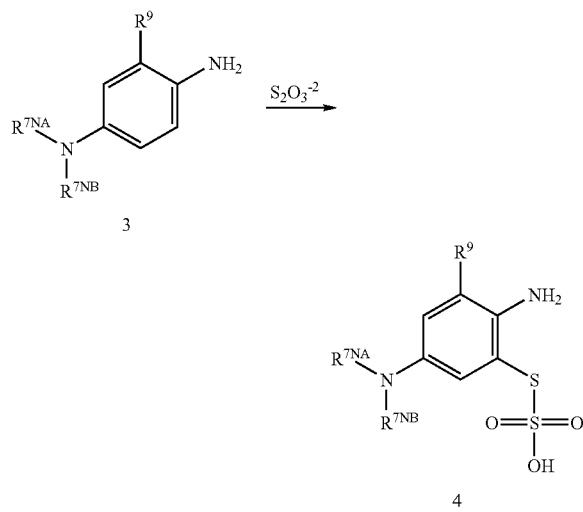

In one embodiment, an N,N-dimethyl-1,4-diamino-benzene, 3', is oxidized in the presence of a thiosulfate to give a thiosulfuric acid S-{2-(amino)-5-(dimethylamino)-phenyl}ester, 4', as illustrated in the following scheme:

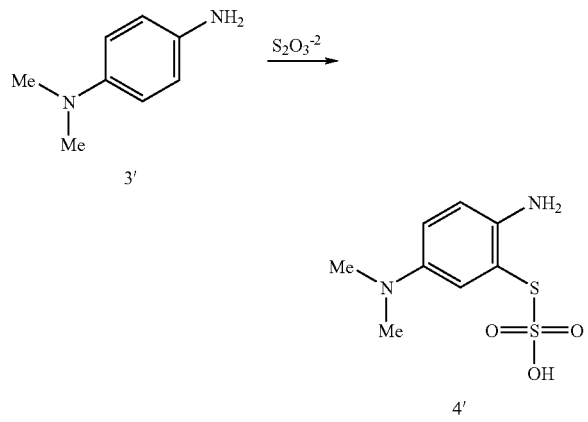

The thiosulfate is or comprises $S_2O_3^{-2}$.

In one embodiment, the thiosulfate is or comprises $Na_2S_2O_3$.

In one embodiment, the thiosulfate is $Na_2S_2O_3$ or a hydrate thereof.

$Na_2S_2O_3$ may be obtained commercially, for example, as the anhydrous salt or as the pentahydrate.

In one embodiment, the molar ratio of thiosulfate to diamine, 3, is 0.8 to 1.5.

In one embodiment, the molar ratio is 1.0 to 1.5.

In one embodiment, the molar ratio is 1.1 to 1.5.

In one embodiment, the molar ratio is 1.1 to 1.3.

In one embodiment, the oxidation is by reaction with an oxidizing agent.

In one embodiment, the oxidizing agent is or comprises Cr(VI).

In one embodiment, the oxidizing agent is or comprises $Cr_2O_7^{-2}$.

In one embodiment, the oxidizing agent is or comprises $Na_2Cr_2O_7$.

In one embodiment, the oxidizing agent is $Na_2Cr_2O_7$ or a hydrate thereof.

$Na_2Cr_2O_7$ may be obtained commercially, for example, as a dihydrate.

In one embodiment, the molar ratio of Cr(VI) to diamine, 3, is 0.2 to 2.0.

In one embodiment, the molar ratio is 0.2 to 1.0.

In one embodiment, the molar ratio is 0.2 to 0.8.

In one embodiment, the molar ratio is 0.3 to 0.7.

In one embodiment, the reaction is performed in an aqueous medium.

In one embodiment, the reaction temperature is 2 to 25° C.

In one embodiment, the reaction temperature is 2 to 15° C.

In one embodiment, the reaction temperature is 2 to 10° C.

In one embodiment, the reaction temperature is about 5° C.

In one embodiment, the reaction time is 10 to 240 minutes.

In one embodiment, the reaction time is 30 to 120 minutes.

In one embodiment, the reaction time is about 60 minutes.

In one embodiment, the reaction mixture is stirred during the reaction step.

Oxidative Coupling (OC)

In this step, a thiosulfuric acid S-{2-(amino)-3-(optionally substituted)-5-(disubstituted amino)-phenyl}ester, 4, is oxidatively coupled to an N,N-disubstituted-3-optionally substituted-aniline, 5, using an oxidizing agent that is or comprises Cr(VI), to give a [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, as illustrated in the following scheme:

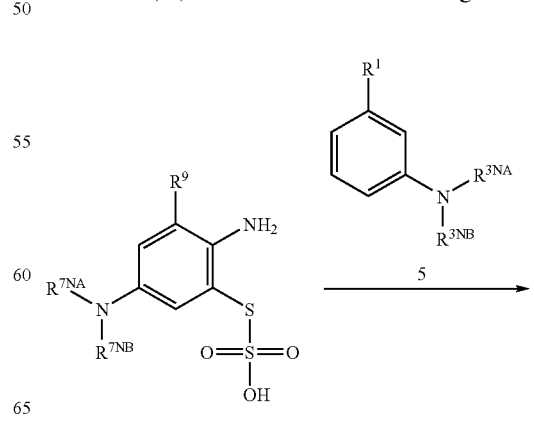

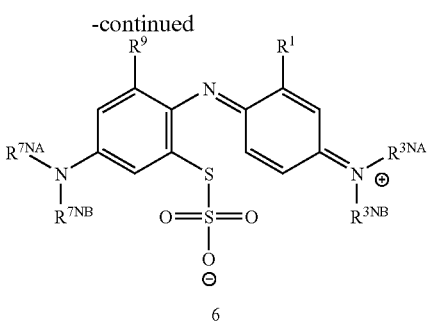

In one embodiment, a thiosulfuric acid S-{2-(amino)-5-(dimethylamino)-phenyl}ester, 4', is oxidatively coupled to an N,N-dimethyl-aniline, 5', using an oxidizing agent that is or comprises Cr(VI), to give a [4-{2-(thiosulfate)-4-(dimethylamino)-phenyl-imino}-cyclohexa-2,5-dienylidene]-N,N-dimethyl ammonium, 6', as illustrated in the following scheme:

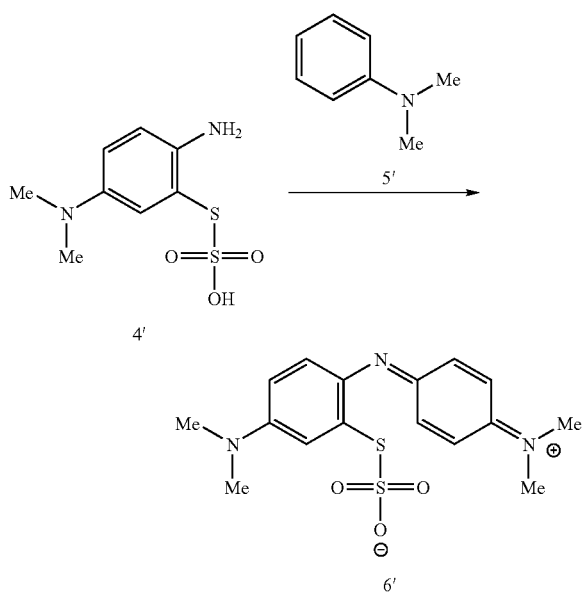

In one embodiment, the ester, 4, is added first, before the aniline, 5, is added.

In one embodiment, the oxidizing agent is or comprises $Cr_2O_7^{-2}$.

In one embodiment, the oxidizing agent is or comprises $Na_2Cr_2O_7$.

In one embodiment, the oxidizing agent is $Na_2Cr_2O_7$.

In one embodiment, the molar ratio of ester, 4, to aniline, 5, is 0.5 to 1.5.

In one embodiment, the range is 0.8 to 1.2.

In one embodiment, the range is about 1.0.

In one embodiment, the molar ratio of Cr(VI) to aniline, 5, is 1.0 to 4.0.

In one embodiment, the range is 1.6 to 3.0.

In one embodiment, the range is 2.0 to 3.0.

In one embodiment, the range is about 2.2.

In one embodiment, the reaction is performed under acidic conditions.

In one embodiment, the reaction is performed at a pH of 1 or less.

In one embodiment, the reaction is performed at a pH of 1 to −1.

In one embodiment, the reaction is performed at a pH of 1 to 0.

In one embodiment, the pH at the end of the reaction step, is 2 to 6.

In one embodiment, the pH at the end of the reaction step, is 3 to 5.

In one embodiment, the pH at the end of the reaction step, is about 4.

In one embodiment, the pH at the end of the reaction step, is about 3.94.

In one embodiment, the acidic conditions are obtained using a strong acid.

In one embodiment, the acidic conditions are obtained using $H_2SO_4$ (which has two strong acid protons).

In one embodiment, the molar ratio of acid protons to aniline, 5, is 1.0 to 4.0.

In one embodiment, the range is 1.5 to 2.5.

In one embodiment, the range is about 2.0.

In one embodiment, the reaction is performed in an aqueous medium.

In one embodiment, the reaction temperature is 2 to 20° C.

In one embodiment, the reaction temperature is 2 to 15° C.

In one embodiment, the reaction temperature is about 5° C.

In one embodiment, the reaction time is 10 minutes to 12 hours.

In one embodiment, the reaction time is 30 minutes to 4 hours.

In one embodiment, the reaction time is about 2 hours.

In one embodiment, the reaction mixture is stirred during the reaction step.

In one embodiment, aniline, 5, is the same as aniline, 1.

Cr(VI) Reduction (CR)

In this step, the product of the oxidative coupling (OC) step is treated to convert residual Cr(VI) to Cr(III).

In one embodiment, at least 25% of residual Cr(VI) is converted to Cr(III).

In one embodiment, the range is at least 35% (i.e., 35 to 100%).

In one embodiment, the range is at least 50% (i.e., 50 to 100%).

In one embodiment, the range is at least 60% (i.e., 60 to 100%).

In one embodiment, the range is at least 70% (i.e., 70 to 100%).

In one embodiment, the range is at least 80% (i.e., 80 to 100%).

In one embodiment, the range is at least 90% (i.e., 90 to 100%).

In one embodiment, the range is at least 95% (i.e., 95 to 100%).

In one embodiment, substantially all of residual Cr(VI) is converted to Cr(III).

The reaction time is selected so as to achieve conversion of a suitable proportion of Cr(VI) to Cr(III).

In one embodiment, the reaction mixture is stirred during the reaction step.

In one embodiment, the reaction is performed in an aqueous medium.

In one embodiment, the treatment is treatment with a reducing agent.

Hydrosulfite:

In one embodiment, the reducing agent is a hydrosulfite (also known as dithionite).

The hydrosulfite is or comprises $S_2O_4^{-2}$.

In one embodiment, the hydrosulfite is a metal hydrosulfite.

In one embodiment, the hydrosulfite is an alkali metal hydrosulfite.

In one embodiment, the hydrosulfite is or comprises $Na_2S_2O_4$ (also known as sodium hydrosulfite and sodium dithionite).

In one embodiment, the hydrosulfite is $Na_2S_2O_4$ or a hydrate thereof.

Without wishing to be bound to any particular theory, it is believed that Cr(VI) reacts with hydrosulfite to form Cr(III) and sodium sulfate (e.g., $Na_2Cr_2O_7+Na_2S_2O_4 \rightarrow Cr_2O_3+ 2Na_2SO_4$).

In one embodiment, the molar amount of hydrosulfite is from 0.02 to 1.0 times the total molar amount of Cr(VI) that was used in the thiosulfonic acid formation (TSAF) step (if performed, and if performed using Cr(VI)) and the oxidative coupling (OC) step.

In one embodiment, the range is 0.03 to 0.7.
In one embodiment, the range is 0.05 to 0.5.
In one embodiment, the range is 0.05 to 0.3.
In one embodiment, the range is 0.1 to 0.2.
In one embodiment, the molar amount is about 0.16 times.
In one embodiment, the hydrosulfite is aqueous hydrosulfite.
In one embodiment, the reaction time is 1 minute to 6 hours.
In one embodiment, the reaction time is 2 minutes to 1 hour.
In one embodiment, the reaction time is about 10 minutes.
In one embodiment, the reaction temperature is 2 to 50° C.
In one embodiment, the reaction temperature is 5 to 30° C.
In one embodiment, the reaction temperature is 10 to 25° C.
In one embodiment, the reaction temperature is room temperature.

Alkanol:

In one embodiment, the reducing agent is an alkanol.
In one embodiment, the alkanol is or comprises a $C_{1-6}$alkanol.
In one embodiment, the $C_{1-6}$alkanol is a saturated aliphatic $C_{1-6}$alkanol.
In one embodiment, the $C_{1-6}$alkanol is ethanol.

Without wishing to be bound to any particular theory, it is believed that Cr(VI) reacts with alkanol (e.g., ethanol) to form Cr(III) and the corresponding aldehyde, i.e., alkanal (e.g., ethanal), which can easily be removed by evaporation.

In one embodiment, the molar amount of alkanol (e.g., ethanol) is from 0.02 to 1.0 times the total molar amount of Cr(VI) that was used in the thiosulfonic acid formation (TSAF) step (if performed, and if performed using Cr(VI)) and the oxidative coupling (OC) step.

In one embodiment, the range is 0.03 to 0.7.
In one embodiment, the range is 0.05 to 0.5.
In one embodiment, the range is 0.05 to 0.3.
In one embodiment, the range is 0.1 to 0.2.
In one embodiment, the molar amount is about 0.12 times.
In one embodiment, the reaction time is 1 hour to 48 hours.
In one embodiment, the reaction time is 2 hours to 24 hours.
In one embodiment, the reaction time is about 16 hours.
In one embodiment, the reaction temperature is 2 to 50° C.
In one embodiment, the reaction temperature is 5 to 30° C.
In one embodiment, the reaction temperature is 10 to 25° C.
In one embodiment, the reaction temperature is room temperature.

Iodide:

In one embodiment, the reducing agent is an iodide.

Without wishing to be bound to any particular theory, it is believed that Cr(VI) reacts with iodide to form Cr(III) and iodine.

In one embodiment, the iodide is or comprises alkali metal iodide.

In one embodiment, the iodide is or comprises sodium iodide or potassium iodide.

In one embodiment, the iodide is or comprises potassium iodide.

In one embodiment, the iodide is potassium iodide.

In one embodiment, the molar amount of iodide is from 0.02 to 1.0 times the total molar amount of Cr(VI) that was used in the thiosulfonic acid formation (TSAF) step (if performed, and if performed using Cr(VI)) and the oxidative coupling (OC) step.

In one embodiment, the range is 0.03 to 0.7.
In one embodiment, the range is 0.05 to 0.5.
In one embodiment, the range is 0.05 to 0.3.
In one embodiment, the range is 0.1 to 0.3.
In one embodiment, the molar amount is about 0.18 times.
In one embodiment, the iodide is aqueous iodide (e.g., aqueous sodium iodide).
In one embodiment, the reaction time is 1 hour to 24 hours.
In one embodiment, the reaction time is 2 hours to 18 hours.
In one embodiment, the reaction time is about 12 hours.
In one embodiment, the reaction temperature is 2 to 50° C.
In one embodiment, the reaction temperature is 5 to 30° C.
In one embodiment, the reaction temperature is 10 to 25° C.
In one embodiment, the reaction temperature is 25° C. or less.
In one embodiment, the reaction temperature is 15° C. or less.
In one embodiment, the reaction temperature is 2 to 25° C.
In one embodiment, the reaction temperature is 2 to 15° C.

pH Adjustment:

In one embodiment, the treatment is treatment with an acid or a base (e.g., a strong acid or a strong base) to achieve a pH of 5.70 to 6.35 (measured at room temperature).

Without wishing to be bound to any particular theory, it is believed that, at a pH in this range, Cr(VI) reacts to form Cr(III).

In one embodiment, the pH range is 5.80 to 6.25.
In one embodiment, the pH range is 5.90 to 6.15.
In one embodiment, the pH range is 5.95 to 6.10.
In one embodiment, the pH is about 6.02.
In one embodiment, the treatment is with strong acid or strong base.
In one embodiment, the treatment is with strong base.
In one embodiment, the treatment is with aqueous NaOH (e.g., 10%).
In one embodiment, the reaction time is 1 hour to 48 hours.
In one embodiment, the reaction time is 2 hours to 24 hours.
In one embodiment, the reaction time is about 16 hours.
In one embodiment, the reaction temperature is 2 to 25° C.
In one embodiment, the reaction temperature is 2 to 15° C.
In one embodiment, the reaction temperature is 5 to 10° C.

Isolation and Purification of Zwitterionic Intermediate (IAPOZI)

In this step, the zwitterionic intermediate, 6, is isolated and purified.

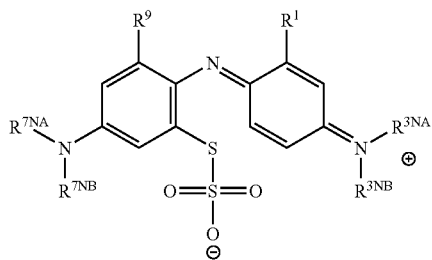

In one embodiment, the isolation and purification is by filtration.

In one embodiment, the isolation and purification is by filtration followed by washing.

In one embodiment, the washing is washing with $H_2O$.

In one embodiment, the washing is washing with $H_2O$ and tetrahydrofuran (THF).

In one embodiment, the volume ratio of $H_2O$ to THF is 1:1 to 10:1, preferably 4:1.

In one embodiment, the isolation and purification is by filtration followed by washing and drying.

In one embodiment, the drying is air-drying.

In one embodiment, the drying is air-drying for 2 to 72 hours.

In one embodiment, the drying is air-drying for 2 to 48 hours.

In one embodiment, the drying is air-drying for 2 to 24 hours.

In one embodiment, the drying is oven-drying.

In one embodiment, the drying is oven-drying for 2 to 72 hours.

In one embodiment, the drying is oven-drying for 2 to 48 hours.

In one embodiment, the drying is oven-drying for 2 to 24 hours.

In one embodiment, the drying is oven-drying at 30 to 60° C. for 2 to 48 hours.

For example, in one embodiment, the reaction mixture is filtered, and the residue (e.g., ~100 mmol crude product) is washed with $H_2O$ (e.g., 4×250 cm³) and THF (e.g., 100 cm³), and then air-dried overnight.

For example, in one embodiment, the reaction mixture is filtered (e.g., through a Buchner filter under vacuum), the solid removed, added to another vessel with fresh water, the mixture stirred vigorously, and filtered again. The "filter-recover-resuspend" process may be repeated a number of times. The finally obtained solid may be used in subsequent steps.

Ring Closure (RC)

In this step, a [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, is subjected to ring closure to give a 3,7-bis(disubstituted-amino)-1,9-(optionally substituted)-phenothiazin-5-ium salt, 7, as illustrated in the following scheme:

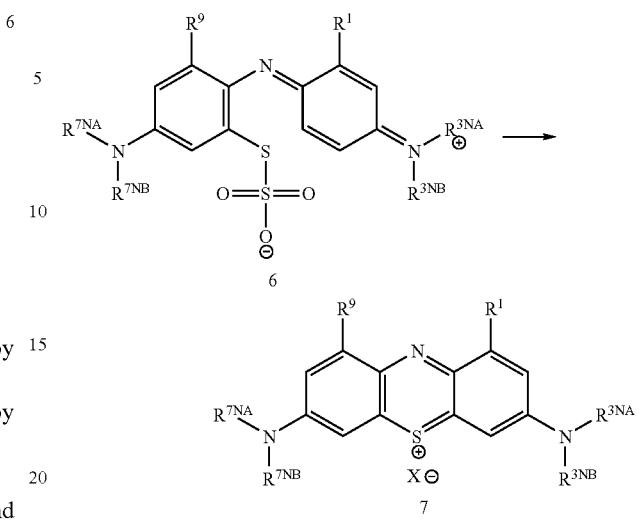

In one embodiment, a [{2-(thiosulfate)-4-(dimethylamino)-phenyl-imino}-cyclohexa-2,5-dienylidene]-N,N-dimethyl ammonium, 6', is subjected to ring closure to give a 3,7-bis(dimethylamino)-phenothiazin-5-ium salt, 7', as illustrated in the following scheme:

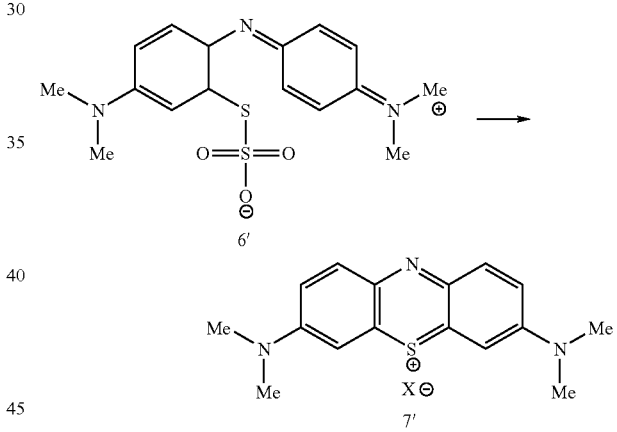

In one embodiment, ring closure is achieved by treatment with an oxidizing agent.

In one embodiment, the oxidizing agent is or comprises Cu(II).

In one embodiment, the oxidizing agent is or comprises Cu(II) sulfate.

In one embodiment, the oxidizing agent is Cu(II) sulfate or a hydrate thereof.

Cu(II) sulfate may be obtained commercially, for example, as a pentahydrate.

Without wishing to be bound by any particular theory, it is believed that the Cu(II) is converted to Cu(I) in the reaction, and precipitates as insoluble $Cu_2O$.

In one embodiment, ring closure is performed under acidic conditions.

In one embodiment, ring closure is performed at a pH of 1 to 5.

In one embodiment, ring closure is performed at a pH of 2 to 5.

In one embodiment, ring closure is performed at a pH of 3 to 4.5.

In one embodiment, ring closure is performed at a pH of 3.5 to 4.1.

In one embodiment, ring closure is performed at a pH of about 3.8.

In one embodiment, the desired pH is obtained by the addition of strong acid.

In one embodiment, the desired pH is obtained by the addition of HCl.

In one embodiment, the molar ratio of Cu(II) to ammonium, 6, is 0.02 to 0.10.

In one embodiment, the range is 0.03 to 0.07

In one embodiment, the range is about 0.05.

In one embodiment, the reaction is performed in an aqueous medium.

In one embodiment, the reaction temperature is 30 to 95° C.

In one embodiment, the reaction temperature is 50 to 90° C.

In one embodiment, the reaction temperature is 60 to 90° C.

In one embodiment, the reaction temperature is about 85° C.

In one embodiment, the reaction time is 10 to 120 minutes.

In one embodiment, the reaction time is 20 to 90 minutes.

In one embodiment, the reaction time is about 60 minutes.

In one embodiment, the reaction is performed until the reaction mixture changes colour, e.g., becomes a deep blue colour.

In one embodiment, the reaction mixture is stirred during the reaction step.

In one embodiment, after reaction, the reaction mixture is filtered and the filtrate collected. (The filtrate contains the desired product in solution.)

In one embodiment, the filtration is performed at a temperature near to the reaction temperature, to give a "hot" filtrate.

In one embodiment, the reaction mixture is first cooled, and the filtration is performed at about room temperature, to give a "cool" filtrate.

Chloride Salt Formation (CSF)

In this step, a 3,7-bis(disubstituted-amino)-1,9-(optionally substituted)-phenothiazin-5-ium salt, 7, is reacted with chloride, to give a 3,7-bis(disubstituted-amino)-1,9-(optionally substituted)-phenothiazin-5-ium chloride salt, 8, as illustrated in the following scheme:

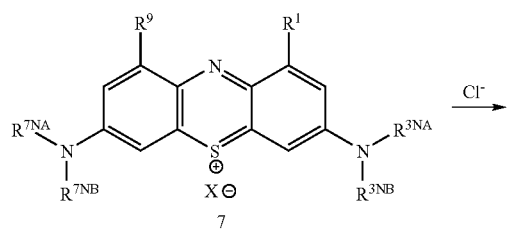

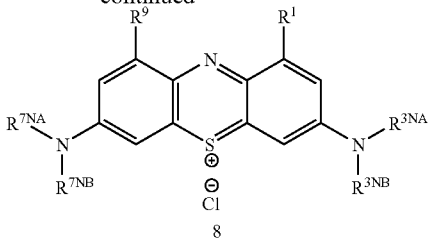

In one embodiment, a 3,7-bis(dimethylamino)-phenothiazin-5-ium salt, 7', is reacted with chloride, to give a 3,7-bis(dimethylamino)-phenothiazin-5-ium chloride salt, 8' (i.e., MTC), as illustrated in the following scheme:

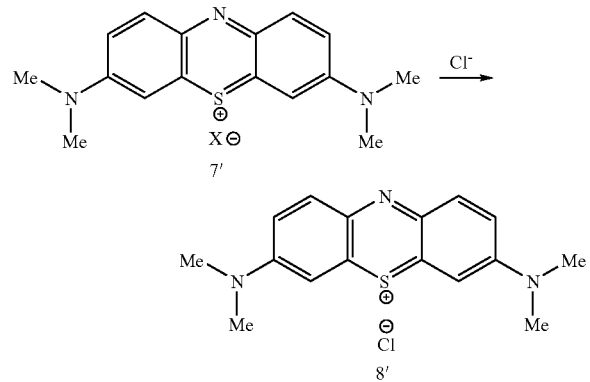

Treatment with Hydrochloric Acid as a Source of Chloride:

In one embodiment, the chloride is hydrochloric acid.

In one embodiment, the reaction is performed at a relatively low pH.

In one embodiment, the relatively low pH is −1 to 3.

In one embodiment, the relatively low pH is 0 to 3.

In one embodiment, the relatively low pH is 0 to 2.

In one embodiment, the relatively low pH is about 1.

In one embodiment, the pH is adjusted to the relatively low pH slowly.

In one embodiment, the pH is adjusted over a period of 5 to 120 minutes.

In one embodiment, the pH is adjusted over a period of 5 to 60 minutes.

In one embodiment, the pH is adjusted over a period of 5 to 30 minutes.

In one embodiment, the pH is adjusted over a period of about 10 minutes.

In one embodiment, the reaction is performed at a relatively cool temperature.

In one embodiment, the relatively cool temperature is 2 to 40° C.

In one embodiment, the relatively cool temperature is 2 to 30° C.

In one embodiment, the relatively cool temperature is 5 to 30° C.

In one embodiment, the relatively cool temperature is 10 to 30° C.

In one embodiment, the relatively cool temperature is 15 to 30° C.

In one embodiment, the relatively cool temperature is 20 to 30° C.

In one embodiment, the relatively cool temperature is about 25° C.

In one embodiment, the reaction is performed until the reaction mixture (initially, e.g., a deep blue colour) becomes light blue to colourless.

In one embodiment, the reaction mixture is stirred during the reaction step.

Treatment with a Chloride Salt as a Source of Chloride:

In one embodiment, the chloride is chloride salt.

In one embodiment, the chloride is alkali metal chloride.

In one embodiment, the chloride is sodium chloride.

In one embodiment, there is a large molar excess of (sodium) chloride.

In one embodiment, the molar ratio of chloride to salt, 7, is 5 to 100.

In one embodiment, the molar ratio is 10 to 80.

In one embodiment, the molar ratio is 10 to 50.

In one embodiment, the molar ratio is about 20.

In one embodiment, the reaction is performed in an aqueous medium.

In one embodiment, the reaction temperature is 20 to 95° C.

In one embodiment, the reaction temperature is 30 to 95° C.

In one embodiment, the reaction temperature is 50 to 80° C.

In one embodiment, the reaction temperature is about 65° C.

In one embodiment, the reaction temperature is about room temperature.

In one embodiment, the reaction time is 10 to 30 minutes.

In one embodiment, the reaction is performed until the reaction mixture (initially, e.g., a deep blue colour) becomes light blue to colourless.

In one embodiment, the reaction mixture is stirred during the reaction step.

In one embodiment, the reaction mixture is allowed to cool following addition of the chloride, to yield the product as a precipitate.

Additional Treatment

Following the chloride salt formation (CSF) step, one or more additional treatment steps (i.e., ST, DT, CT, EDTAT, OE) may be performed, as described next. If two or more of these treatment steps are performed, they may be performed in any order. These treatment steps give rise to improved purity, especially reduced metal content and reduced organic impurity content.

In one embodiment, one or more additional treatment steps selected from ST, DT, CT, and EDTAT are performed, followed by OE.

Sulphide Treatment (ST)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a sulphide.

In one embodiment, the salt, 7, is treated with a sulphide.

In one embodiment, the chloride salt, 8, is treated with a sulphide.

The sulphide is or comprises $S^{2-}$.

In one embodiment, the sulphide is a metal sulphide.

In one embodiment, the sulphide is an alkali metal sulphide.

In one embodiment, the sulphide is or comprises $Na_2S$.

In one embodiment, the sulphide is $Na_2S$.

In one embodiment, the sulphide is a transition metal sulphide.

In one embodiment, the sulphide is or comprises ZnS.

In one embodiment, the sulphide is ZnS.

In one embodiment, the amount of sulphide is 0.01 to 0.20 equivalents.

In one embodiment, the range is 0.05 to 0.15 equivalents.

In one embodiment, the range is about 0.1 equivalents.

In one embodiment, the (initial) concentration of salt 7 or 8 is 0.005 to 0.25 M.

In one embodiment, range is 0.02 to 0.30 M.

In one embodiment, range is 0.05 to 0.20 M.

In one embodiment, the (initial) concentration is about 0.10 M.

In one embodiment, the treatment is treatment with a sulphide and a chloride.

In one embodiment, the chloride is or comprises NaCl.

In one embodiment, the chloride is NaCl.

In one embodiment, there is a molar excess of chloride.

In one embodiment, the amount of chloride is 5 to 300 equivalents.

In one embodiment, the amount of chloride is 5 to 40 equivalents.

In one embodiment, the amount of chloride is 5 to 30 equivalents.

In one embodiment, the amount of chloride is about 20 equivalents.

In one embodiment, the amount of chloride is about 200 equivalents.

In one embodiment, the treatment is performed at a temperature of 2 to 20° C.

In one embodiment, the temperature range is 2 to 15° C.

In one embodiment, the temperature range is 5 to 15° C.

In one embodiment, the temperature is about 10° C. (e.g., 10±2° C.).

In one embodiment, the treatment is performed in an aqueous medium.

In one embodiment, the treatment is performed under basic conditions.

In one embodiment, the treatment is performed at a pH of 9 to 12.

In one embodiment, the treatment is performed at a pH of 10 to 11.

In one embodiment, the treatment is performed at a pH of about 10.5.

In one embodiment, the treatment is performed so that the pH of the reaction mixture reaches at least 9 to 12.

In one embodiment, the treatment is performed so that the pH of the reaction mixture reaches at least 10 to 11.

In one embodiment, the treatment is performed so that the pH of the reaction mixture reaches at least about 10.5.

In one embodiment, the treatment is performed at a temperature of about 10° C. (e.g., 10±2° C.) and at a pH of about 10.5, or is performed so that the pH of the reaction mixture reaches at least about 10.5.

In one embodiment, the reaction mixture is stirred during the reaction step.

For example, in one embodiment, crude MTC product is fully dissolved in water at a concentration of about 0.1 M at a temperature of about 65° C. The solution is cooled. The cooled solution is optionally filtered. The solution is treated with about 0.1 equivalents of aqueous sodium sulphide, or an amount sufficient to achieve a pH of about 10.5 (e.g., 10.5±0.5). The resulting mixture is stirred (e.g., for about 10 minutes), filtered, and the filtrate collected. In one embodiment, a large excess of sodium chloride (e.g., about 23 equivalents) is added to the filtrate with stirring, and the resulting precipitate is collected. Alternatively, in another embodiment, the pH of the cool (e.g., about 20° C.) solution is adjusted to about pH 1 using HCl, and the resulting precipitate collected.

In one embodiment, following treatment with sulphide (e.g., and before treatment with chloride), the product (e.g., in solution) is additionally washed with an organic solvent.

In one embodiment, the organic solvent is selected from dichloromethane, 1,2-dichloroethane, chloroform, ethyl acetate, diethyl ether, chlorobenzene, petroleum ether (e.g., 40:60), benzene, toluene, and methyl acetate. In one embodiment, the organic solvent is dichloromethane.

In one embodiment, e.g., following washing with an organic solvent, the pH of the solution of the washed product is adjusted to about 4.5 to about 5.5, or about 5.0. In one embodiment, the solution is (e.g., is additionally) heated/cooled to approximately 20° C. and then subjected to cool acid recrystallisation (e.g., pH adjusted to about 1 using HCl, and the resulting precipitate collected). In an alternative embodiment, the solution is (e.g., is additionally) heated to approximately 65° C. and subjected to hot salting out.

For example, in one embodiment, crude MTC product is fully dissolved in water at a concentration of about 0.06 M at a temperature of about 60° C. The solution is cooled. The cooled solution is optionally filtered. The solution is treated with about 0.07 equivalents of aqueous sodium sulphide. The resulting mixture is stirred (e.g., for about 15 minutes), filtered, and the filtrate collected. The filtrate is washed with dichloromethane (e.g., several times). In one embodiment, the washed filtrate is heated to about 60° C., and a large excess of sodium chloride (e.g., about 260 equivalents) is added to the (hot) filtrate with stirring. The hot solution is allowed to cool very slowly, and the (highly crystalline) precipitate is collected (e.g., "hot salting out"). Alternatively, in another embodiment, the pH of the cool (e.g., about 20° C.) washed filtrate is adjusted to about pH 1 using HCl, and the resulting precipitate collected.

Dimethyldithiocarbamate Treatment (DT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a dimethyldithiocarbamate.

In one embodiment, the salt, 7, is treated with a dimethyldithiocarbamate.

In one embodiment, the chloride salt, 8, is treated with a dimethyldithiocarbamate.

The dimethyldithiocarbamate is or comprises $(CH_3)_2NCS_2^-$.

In one embodiment, the dimethyldithiocarbamate is or comprises $(CH_3)_2NCS_2Na$.

In one embodiment, the dimethyldithiocarbamate is $(CH_3)_2NCS_2Na$.

In one embodiment, the amount of dimethyldithiocarbamate is 0.01 to 0.20 equivalents.

In one embodiment, the range is 0.05 to 0.15 equivalents.

In one embodiment, the range is about 0.1 equivalents.

In one embodiment, the (initial) concentration of salt 7 or 8 is 0.005 to 0.25 M.

In one embodiment, range is 0.02 to 0.30 M.

In one embodiment, range is 0.05 to 0.20 M.

In one embodiment, the (initial) concentration is about 0.10 M.

In one embodiment, the treatment is treatment with a dimethyldithiocarbamate and a chloride.

In one embodiment, the chloride is or comprises NaCl.

In one embodiment, the chloride is NaCl.

In one embodiment, there is a molar excess of chloride.

In one embodiment, the amount of chloride is 5 to 40 equivalents.

In one embodiment, the amount of chloride is 5 to 30 equivalents.

In one embodiment, the amount of chloride is about 20 equivalents.

In one embodiment, the treatment is performed in an aqueous medium.

In one embodiment, the reaction mixture is stirred during the reaction step.

For example, in one embodiment, crude MTC product is fully dissolved in water at a concentration of about 0.1 M at a temperature of about 65° C. The solution is cooled. The cooled solution is optionally filtered. The solution is treated with about 0.1 equivalents of aqueous dimethyldithiocarbamic acid, sodium salt. The resulting mixture is stirred (e.g., for about 10 minutes), filtered, and the filtrate collected. A large excess of sodium chloride (e.g., about 23 equivalents) is added to the filtrate with stirring, and the resulting precipitate is collected.

In one embodiment, following treatment with dimethyldithiocarbamate (e.g., and before treatment with chloride), the product (e.g., in solution) is additionally washed with an organic solvent, as described above for sulphide treatment.

In one embodiment, e.g., following washing with an organic solvent, the pH of the solution of the washed product is adjusted to about 4.5 to about 5.5, or about 5.0, as described above for sulphide treatment.

Carbonate Treatment (CT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a carbonate.

In one embodiment, the salt, 7, is treated with a carbonate.

In one embodiment, the chloride salt, 8, is treated with a carbonate.

The carbonate is or comprises $CO_3^{2-}$.

In one embodiment, the carbonate is or comprises alkali metal carbonate.

In one embodiment, the carbonate is or comprises sodium carbonate.

In one embodiment, the carbonate is sodium carbonate.

In one embodiment, the amount of sodium carbonate is 0.01 to 0.20 equivalents.

In one embodiment, the range is 0.05 to 0.15 equivalents.

In one embodiment, the amount is about 0.1 equivalents.

In one embodiment, the (initial) concentration of salt 7 or 8 is 0.005 to 0.25 M.

In one embodiment, range is 0.02 to 0.30 M.

In one embodiment, range is 0.05 to 0.20 M.

In one embodiment, the (initial) concentration is about 0.10 M.

In one embodiment, the treatment is treatment with a carbonate and a chloride.

In one embodiment, the chloride is or comprises NaCl.

In one embodiment, the chloride is NaCl.

In one embodiment, there is a molar excess of chloride.

In one embodiment, the amount of chloride is 5 to 40 equivalents.

In one embodiment, the amount of chloride is 5 to 30 equivalents.

In one embodiment, the amount of chloride is about 20 equivalents.

In one embodiment, the treatment is performed in an aqueous medium.

In one embodiment, the reaction mixture is stirred during the reaction step.

For example, in one embodiment, crude MTC product is fully dissolved in water at a concentration of about 0.1 M at a temperature of about 65° C. The solution is cooled. The cooled solution is optionally filtered. The solution is treated with about 0.1 equivalents of aqueous sodium carbonate. The resulting mixture is stirred (e.g., for about 10 minutes), filtered, and the filtrate collected. A large excess of sodium chloride (e.g., about 23 equivalents) is added to the filtrate with stirring, and the resulting precipitate is collected.

In one embodiment, following treatment with carbonate (e.g., and before treatment with chloride), the product (e.g., in solution) is additionally washed with an organic solvent, as described above for sulphide treatment.

In one embodiment, e.g., following washing with an organic solvent, the pH of the solution of the washed product is adjusted to about 4.5 to about 5.5, or about 5.0, as described above for sulphide treatment.

Ethylenediaminetetraacetic Acid Treatment (EDTAT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with ethylenediaminetetraacetic acid (EDTA) or an EDTA salt.

In one embodiment, the salt, 7, is treated with EDTA or an EDTA salt.

In one embodiment, the chloride salt, 8, is treated with EDTA or an EDTA salt.

In one embodiment, the EDTA salt is or comprises EDTA alkali metal salt.

In one embodiment, the EDTA salt is or comprises EDTA disodium salt.

In one embodiment, the EDTA salt is EDTA disodium salt.

In one embodiment, the amount of EDTA is 0.01 to 0.20 equivalents.

In one embodiment, the range is 0.05 to 0.15 equivalents.

In one embodiment, the amount is about 0.1 equivalents.

In one embodiment, the (initial) concentration of salt 7 or 8 is 0.005 to 0.25 M.

In one embodiment, range is 0.02 to 0.30 M.

In one embodiment, range is 0.05 to 0.20 M.

In one embodiment, the (initial) concentration is about 0.10 M.

In one embodiment, the treatment is treatment with EDTA or an EDTA salt and a chloride.

In one embodiment, the chloride is or comprises NaCl.

In one embodiment, the chloride is NaCl.

In one embodiment, there is a molar excess of chloride.

In one embodiment, the amount of chloride is 5 to 40 equivalents.

In one embodiment, the amount of chloride is 5 to 30 equivalents.

In one embodiment, the amount of chloride is about 10 equivalents.

In one embodiment, the treatment is performed in an aqueous medium.

In one embodiment, the reaction mixture is stirred during the reaction step.

For example, in one embodiment, crude MTC product is fully dissolved in water at a concentration of about 0.1 M at a temperature of about 65° C. The solution is cooled to room temperature, and then the solution is treated with about 0.1 equivalents of aqueous EDTA disodium salt. The resulting mixture is stirred (e.g., for about 1 hour), filtered, and the filtrate collected. A large excess of sodium chloride (e.g., about 10 equivalents) is added to the filtrate with stirring, and the resulting precipitate is collected.

In one embodiment, following treatment with EDTA (e.g., and before treatment with chloride), the product (e.g., in solution) is additionally washed with an organic solvent, as described above for sulphide treatment.

In one embodiment, e.g., following washing with an organic solvent, the pH of the solution of the washed product is adjusted to about 4.5 to about 5.5, or about 5.0, as described above for sulphide treatment.

Organic Extraction (OE)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, in aqueous solution or suspension, is treated with (e.g., washed with) an organic solvent.

In one embodiment, the salt, 7, in aqueous solution or suspension, is treated with (e.g., washed with) an organic solvent.

In one embodiment, the chloride salt, 8, in aqueous solution or suspension, is treated with (e.g., washed with) an organic solvent.

In one embodiment, the organic solvent is dichloromethane ($CH_2Cl_2$, DCM).

DCM is a "class 2" chemical, with a permitted daily exposure (PDE) of 6 mg/day.

In one embodiment, the volume ratio of aqueous solution or suspension of salt, 7 or 8, to organic solvent (e.g., DCM) is 0.1 to 10.

In one embodiment, the ratio is 0.5 to 5.

In one embodiment, the ration is 0.5 to 2.

In one embodiment, the treatment (e.g., washing) is performed iteratively using a plurality of aliquots of the organic solvent (e.g., DCM).

For example, in one embodiment, 250 mL of aqueous solution of the salt, 7 or 8, is washed with 50 mL of DCM, five times, for a total volume of 250 mL DCM, and a volume ratio of 1.

In one embodiment, aqueous solution or suspension of salt, 7 or 8, has a pH of 8 to 12.

In one embodiment, the pH range is 9 to 12.

In one embodiment, the pH range is 9 to 11.

In one embodiment, the pH range is about 10.8.

In one embodiment, the treatment (e.g., washing) is performed at a temperature of 2 to 20° C.

In one embodiment, the temperature range is 2 to 15° C.

In one embodiment, the temperature is about 10° C.

Treatment (e.g., washing) may be performed, for example, using a reaction vessel equipped with an overhead mechanical stirrer attached to a shaft with a paddle as well as a run-off tap at the bottom of the flask. Aqueous solution or suspension of salt, 7 or 8, is placed in the vessel, and an aliquot of organic solvent (e.g., DCM) is added and the heterogeneous mixture stirred for a suitable period. The layers are allowed to separate, and the lower (organic solvent) layer is discarded via the run-off tap. Another aliquot of organic solvent (e.g., DCM) is added and the process repeated, e.g., several times.

Organic extraction (OE) is particularly effective at greatly reducing the organic impurity levels of the solid (e.g., crystalline) product ultimately obtained.

In one embodiment, one or more additional treatment steps selected from ST, DT, CT, and EDTAT are performed first, followed by organic extraction (OE).

Recrystallisation (RX)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is recrystallised.

In one embodiment, the salt, 7, is recrystallised.

In one embodiment, the chloride salt, 8, is recrystallised.

The recrystallisation step further improves purity and also provides a product with a suitable particle size, e.g., a particle size suitable for use in subsequent pharmaceutical formulation.

For the avoidance of doubt, note that "crystallisation" and "recrystallisation" are used interchangeably herein to mean the formation of a solid precipitate (e.g., crystals) from a solution or suspension, and that "re-" in the term "recrystallisation" does not require that the newly crystallised product was previously in a solid or crystalline form.

Cool Acidic Recrystallisation (RX-CAR):

In one embodiment, the recrystallisation is recrystallisation from water (e.g., from an aqueous solution or aqueous suspension) at a relatively cool temperature by adjusting the pH to a relatively low pH (e.g., "cool acidic crystallisation").

In one embodiment, the pH is adjusted using HCl.

In one embodiment, the relatively cool temperature is 2 to 40° C.

In one embodiment, the relatively cool temperature is 2 to 30° C.

In one embodiment, the relatively cool temperature is 5 to 30° C.

In one embodiment, the relatively cool temperature is 10 to 30° C.

In one embodiment, the relatively cool temperature is 15 to 30° C.

In one embodiment, the relatively cool temperature is 20 to 30° C.

In one embodiment, the relatively cool temperature is about 25° C.

In one embodiment, the relatively low pH is −1 to 3.

In one embodiment, the relatively low pH is 0 to 3.

In one embodiment, the relatively low pH is 0 to 2.

In one embodiment, the relatively low pH is about 1.

In one embodiment, the pH is adjusted to the relatively low pH slowly.

In one embodiment, the pH is adjusted over a period of 5 to 120 minutes.

In one embodiment, the pH is adjusted over a period of 5 to 60 minutes.

In one embodiment, the pH is adjusted over a period of 5 to 30 minutes.

In one embodiment, the pH is adjusted over a period of about 10 minutes.

Cool acidic recrystallisation (RX-CAR) is particularly effective at greatly reducing the metal content of the results solid (e.g., crystalline) product.

Hot Salting Out (RX-HSO):

In one embodiment, the recrystallisation is recrystallisation from water (e.g., from an aqueous solution or aqueous suspension) at an initial elevated temperature, in the presence of a chloride, such as sodium chloride (e.g., "hot salting out").

In one embodiment, the (initial) concentration of salt 7 or 8 is 0.002 to 0.05 M.

In one embodiment, range is 0.005 to 0.04 M.

In one embodiment, range is 0.01 to 0.04 M.

In one embodiment, the (initial) concentration is about 0.03 M.

In one embodiment, the initial elevated temperature is 30 to 90° C.

In one embodiment, the range is 40 to 80° C.

In one embodiment, the range is 50 to 80° C.

In one embodiment, the initial elevated temperature is about 65° C.

In one embodiment, the (initial) concentration of (sodium) chloride is 0.1 to 3.0 M.

In one embodiment, the range is 0.5 to 2.5 M.

In one embodiment, the range is 1.0 to 2.2 M.

In one embodiment, the (initial) concentration is about 2.0 M.

In one embodiment, there is a large molar excess of (sodium) chloride.

In one embodiment, the molar ratio of (sodium) chloride to salt, 7 or 8, is 5 to 100.

In one embodiment, the molar ratio is 20 to 80.

In one embodiment, the molar ratio is 50 to 80.

In one embodiment, the molar ratio is about 65.

In one embodiment, the recrystallisation includes subsequent drying of the recrystallised (highly crystalline) precipitate, for example, in an oven at a suitable temperature (e.g., 50 to 120° C.) for a suitable time (e.g., 1 to 24 hours).

For example, in one embodiment, crude MTC product or treated crude MTC product is dissolved in $H_2O$ at a concentration of about 0.03 M, and at approximately 65° C. Optionally, the solution is filtered. Sodium chloride is added. The mixture is allowed to cool, for example, to about room temperature, slowly, for example, over 1 to 10 hours. The resulting (highly crystalline) precipitate is collected, and optionally dried, for example, in an oven (e.g., at about 75° C.) for an appropriate time (e.g., about 16 hours).

Trituration (RX-TRIT):

In one embodiment, the recrystallisation is recrystallisation from water (e.g., from an aqueous solution or aqueous suspension) at an initial elevated temperature, in the presence of tetrahydrofuran (THF) (e.g., trituration).

In one embodiment, the (initial) concentration of salt 7 or 8 is 0.002 to 0.20 M.

In one embodiment, range is 0.01 to 0.20 M.

In one embodiment, range is 0.05 to 0.15 M.

In one embodiment, the (initial) concentration is about 0.13 M.

In one embodiment, the initial elevated temperature is 30 to 90° C.

In one embodiment, the range is 40 to 80° C.

In one embodiment, the range is 50 to 80° C.

In one embodiment, the initial elevated temperature is about 65° C.

In one embodiment, the ratio of water to THF is 20:1 to 2:1, by volume.

In one embodiment, the range is 10:1 to 2:1.

In one embodiment, the range is 7:1 to 3:1.

In one embodiment, the ratio is about 5:1.

In one embodiment, the recrystallisation includes subsequent drying of the recrystallised (highly crystalline) precipitate, for example, in an oven at a suitable temperature (e.g., 50 to 120° C.) for a suitable time (e.g., 1 to 24 hours).

For example, in one embodiment, crude MTC product or treated crude MTC product is dissolved in water at a concentration of about 0.13 M, and at approximately 65° C. Optionally, the solution is filtered. The mixture is allowed to cool slowly, and THF is added when the temperature reaches about 25° C., at a water:THF volume ratio of about 5:1. The mixture is again allowed to cool, for example, to about 5° C., slowly, for example, over 1 to 10 hours. The resulting (highly crystalline) precipitate is collected, and optionally dried, for example, in an oven (e.g., at about 100° C.) for an appropriate time (e.g., about 2 hours).

Synthesis Method B

One important difference between the known methods and the presently claimed Method B is the use of sodium sulphide ($Na_2S$) instead of other sulphides, such as hydrogen sulphide ($H_2S$) in the ring fusion (RF-2) step. See, for example, Michaelis et al., 1940. However, hydrogen sulphide is extremely dangerous and is both difficult and expensive to use in an industrial process. By using sodium sulphide, these disadvantages are overcome. In addition, sodium sulphide is a solid, is easier to handle, and can be weighed more easily and accurately; this permits better control of the reaction.

In one embodiment, the method comprises the step of:
ring fusion (RF-2).

In one embodiment, the method additionally comprises the subsequent step of:
chloride salt formation (CSF-2).

In one embodiment, the method additionally comprises the initial step of:
nitrosyl reduction (NR-2).

In one embodiment, the method additionally comprises the initial steps of:
nitrosylation (NOS-2);
nitrosyl reduction (NR-2).

In one embodiment, the method additionally comprises the initial steps of:
N,N-disubstitution (NNDS-2);
nitrosylation (NOS-2);
nitrosyl reduction (NR-2).

Thus, in one embodiment, the method comprises the steps of, in order:
N,N-disubstitution (NNDS-2);
nitrosylation (NOS-2);
nitrosyl reduction (NR-2);
ring fusion (RF-2);
chloride salt formation (CSF-2).

This method is particularly well suited for the synthesis of diaminophenothiazinium compounds wherein $R^1$ and $R^9$ are other than —H, as in, for example, 1,9-diethyl methylthioninium chloride (DEMTC).

N,N-Disubstitution (NNDS-2)

In this step, a 3-optionally substituted-aniline, 9, is N,N-disubstituted using an alkyl halide, an alkenyl halide, or a haloalkyl halide, to give a N,N-disubstituted-3-optionally substituted-aniline, 10, as illustrated in the following scheme:

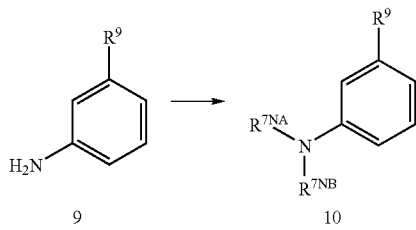

In one embodiment, a 3-ethyl-aniline, 9, is N,N-dimethylated using a methyl halide, to give a N,N-dimethyl-3-ethyl-aniline, 10, as illustrated in the following scheme:

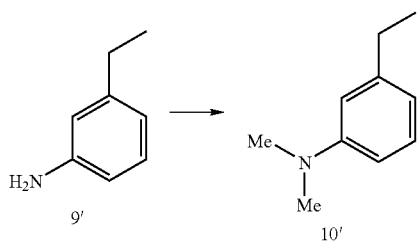

In one embodiment, the reaction uses an alkyl halide.

In one embodiment, the reaction uses an alkenyl halide.

In one embodiment, the reaction uses a haloalkyl halide.

In one embodiment, the halide is a chloride, bromide, or iodide.

In one embodiment, the halide is a bromide or iodide.

In one embodiment, the halide is an iodide.

In one embodiment, the reaction uses methyl iodide.

In one embodiment, the molar ratio of alkyl halide, alkenyl halide, or haloalkyl halide, to aniline, 9, is 2.0 to 4.0. In one embodiment, the molar ratio is 2.5 to 3.5.

In one embodiment, the reaction is performed under basic conditions.

In one embodiment, the reaction is performed at a pH of 8 or more.

In one embodiment, the reaction is performed at a pH of 8 to 14.

In one embodiment, the reaction is performed at a pH of 8 to 12.

In one embodiment, the reaction is performed at a pH of 8 to 10.

In one embodiment, the basic conditions are obtained using sodium carbonate.

In one embodiment, the molar ratio of alkyl halide, alkenyl halide, or haloalkyl halide to base (e.g., sodium carbonate) is about 2.0.

In one embodiment, the reaction temperature is 25 to 65° C.

In one embodiment, the reaction temperature is 35 to 55° C.

In one embodiment, the reaction temperature is about 45° C.

In one embodiment, the reaction time is 1 to 24 hours.

In one embodiment, the reaction time is 2 to 18 hours.

In one embodiment, the reaction time is about 10 hours.

In one embodiment, the reaction mixture is stirred during the reaction step.

In one embodiment, the reaction is terminated by the addition of water.

Nitrosylation (NOS-2)

In this step, an N,N-disubstituted-3-optionally substituted aniline, 10, is 4-nitrosylated to give the corresponding N,N-disubstituted-3-optionally substituted-4-nitrosyl aniline, 11, as illustrated in the following scheme:

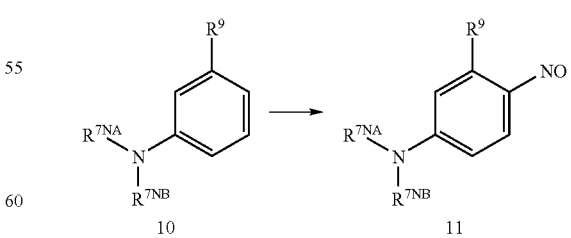

In one embodiment, an N,N-dimethyl-3-ethyl-aniline, 10', is 4-nitrosylated to form the corresponding N,N-dimethyl-3-ethyl-4-nitrosyl aniline, 11', as illustrated in the following scheme:

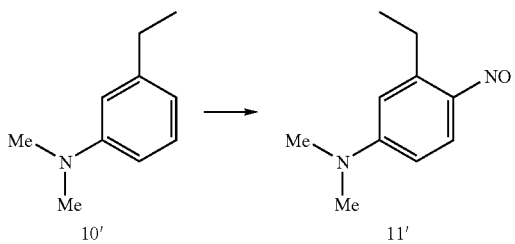

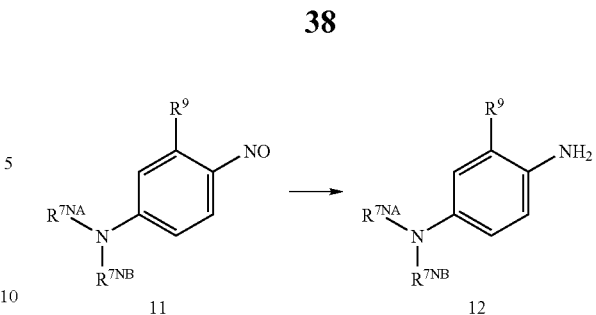

In one embodiment, the nitrosylation is performed using a nitrite.

In one embodiment, the nitrite is or comprises $NO_2^-$.

In one embodiment, the nitrite is or comprises alkali metal nitrite.

In one embodiment, the nitrite is or comprises sodium nitrite or potassium nitrite.

In one embodiment, the nitrite is or comprises sodium nitrite.

In one embodiment, the nitrite is sodium nitrite.

In one embodiment, the molar ratio of nitrite to aniline, 9, is 0.8 to 1.5.

In one embodiment, the molar ratio is 1.0 to 1.5.
In one embodiment, the molar ratio is 1.0 to 1.3.
In one embodiment, the molar ratio is 1.0 to 1.1.
In one embodiment, the molar ratio is 1.1 to 1.5.
In one embodiment, the molar ratio is 1.1 to 1.3.
In one embodiment, the reaction is performed under acidic conditions.

In one embodiment, the reaction is performed at a pH of 1 or less.

In one embodiment, the reaction is performed at a pH of 1 to −1.

In one embodiment, the reaction is performed at a pH of 1 to 0.

In one embodiment, the acidic conditions are obtained using a strong acid.

In one embodiment, the acidic conditions are obtained using HCl (which has one strong acid proton).

In one embodiment, the molar ratio of acid protons to aniline, 9, is 1 to 4.

In one embodiment, the range is 2 to 4.
In one embodiment, the range is 3 to 4.
In one embodiment, the ratio is about 3.2.
In one embodiment, the range is 2 to 3.
In one embodiment, the range is 2.25 to 2.75.
In one embodiment, the ratio is about 2.5.
In one embodiment, the reaction is performed in an aqueous medium.

In one embodiment, the reaction temperature is 2 to 25° C.
In one embodiment, the reaction temperature is 2 to 15° C.
In one embodiment, the reaction temperature is 2 to 10° C.
In one embodiment, the reaction temperature is about 5° C.
In one embodiment, the reaction time is 10 to 240 minutes.
In one embodiment, the reaction time is 30 to 120 minutes.
In one embodiment, the reaction time is about 60 minutes.
In one embodiment, the reaction mixture is stirred during the reaction step.

Nitrosyl Reduction (NR-2)

In this step, an N,N-disubstituted-3-optionally substituted-4-nitrosyl aniline, 11, is reduced to give an N,N-disubstituted-1,4-diamino-5-optionally substituted benzene, 12, as illustrated in the following scheme:

In one embodiment, an N,N-dimethyl-3-ethyl-4-nitrosyl-aniline, 11', is reduced to give an N,N-dimethyl-1,4-diamino-3-ethyl-benzene, 12', as illustrated in the following scheme:

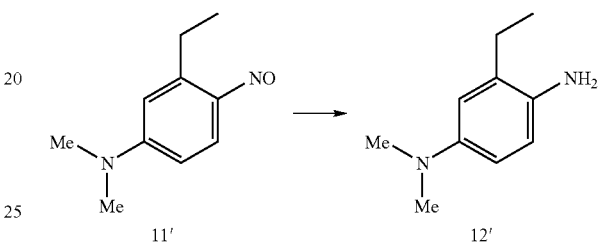

In one embodiment, the reduction is by reaction with a reducing agent.

In one embodiment, the reducing agent is or comprises Fe(0).

In one embodiment, the reducing agent is or comprises metallic iron.

In one embodiment, the reducing agent is metallic iron.

Metallic iron may be obtained commercially, for example, as metal filings.

In one embodiment, the molar ratio of Fe(0) to aniline, 9, is 1.0 to 4.0.

In one embodiment, the molar ratio is 1.5 to 4.0.
In one embodiment, the molar ratio is 1.5 to 3.0.
In one embodiment, the molar ratio is 1.5 to 2.5.
In one embodiment, the reaction is performed under acidic conditions.

In one embodiment, the reaction is performed at a pH of 1 or less.

In one embodiment, the reaction is performed at a pH of 1 to −1.

In one embodiment, the reaction is performed at a pH of 1 to 0.

In one embodiment, the acidic conditions are obtained using a strong acid.

In one embodiment, the acidic conditions are obtained using HCl (which has one strong acid proton).

In one embodiment, the molar ratio of acid protons to aniline, 9, is 1 to 4.

In one embodiment, the range is 2 to 4.
In one embodiment, the range is 3 to 4.
In one embodiment, the ratio is about 3.2.
In one embodiment, the range is 2 to 3.
In one embodiment, the range is 2.25 to 2.75.
In one embodiment, the ratio is about 2.5.
In one embodiment, the reaction is performed in an aqueous medium.

In one embodiment, the reaction is performed at a temperature of 2 to 35° C.

In one embodiment, the reaction is performed at a temperature of 10 to 30° C.

In one embodiment, the reaction is performed for a time of 10 minutes to 12 hours.

In one embodiment, the reaction is performed for a time of 30 minutes to 6 hours.

In one embodiment, the reaction is performed for a time of about 3 hours.

In one embodiment, the reaction mixture is stirred during the reaction step.

Ring Fusion (RF-2)

In this step, two molecules of N,N-disubstituted-1,4-diamino-5-optionally substituted benzene, 12, are fused in the presence of alkali metal sulphide and iron(III), at a pH of 0.6 to 2.6, to give a 3,7-bis(disubstituted-amino)-1,9-(optionally substituted)-phenothiazin-5-ium salt, 13, as illustrated in the following scheme:

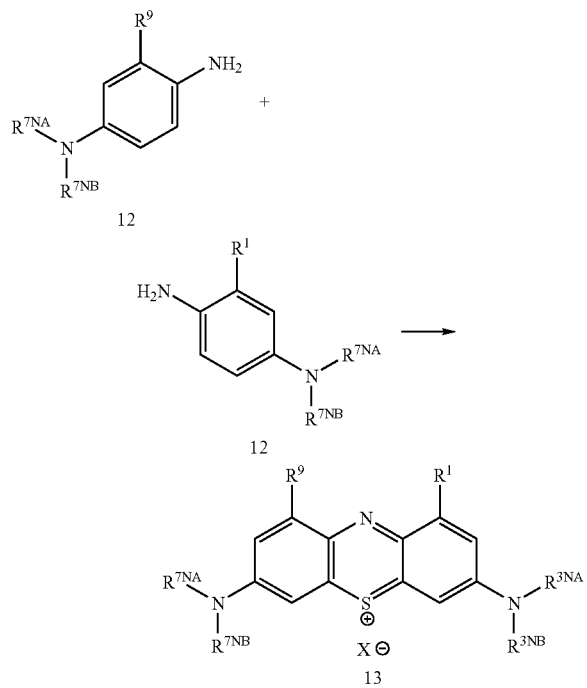

In one embodiment, two molecules of N,N-dimethyl-1,4-diamino-5-ethyl-benzene, 12, are fused in the presence of alkali metal sulphide and iron(III) at a pH of 0.6 to 2.6, to give a 3,7-bis(dimethyl-amino)-1,9-(diethyl)-phenothiazin-5-ium salt, 13, as illustrated in the following scheme:

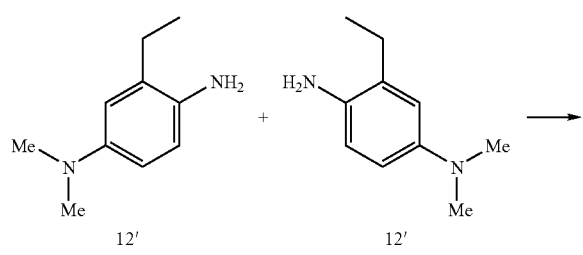

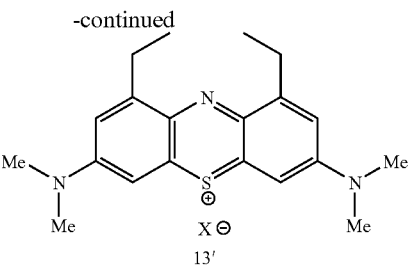

In one embodiment, the alkali metal sulphide is or comprises sodium sulphide or potassium sulphide.

In one embodiment, the alkali metal sulphide is or comprises sodium sulphide.

In one embodiment, the alkali metal sulphide is sodium sulphide.

In one embodiment, the iron(III) is or comprises iron(III) halide.

In one embodiment, the iron(III) is or comprises iron(III) chloride.

In one embodiment, the iron(III) is iron(III) chloride or a hydrate thereof.

Iron(III) chloride may be obtained commercially, for example, as the anhydrous salt or as the hexahydrate.

In one embodiment, the reaction is performed under acidic conditions.

In one embodiment, the reaction is performed at a pH of 0.8 to 2.4.

In one embodiment, the range is 1.0 to 2.2.
In one embodiment, the range is 1.2 to 2.0.
In one embodiment, the range is 1.4 to 1.8.
In one embodiment, the pH is about 1.6.
In one embodiment, the molar ratio of sulphide to aniline, 12, is 0.5 to 2.0.

In one embodiment, the molar ratio is 0.8 to 1.5.
In one embodiment, the molar ratio is about 1.0.
In one embodiment, the molar ratio of Fe(III) to aniline, 12, is 2.0 to 6.0.

In one embodiment, the molar ratio is 2.6 to 4.0.
In one embodiment, the molar ratio is about 3.0.
In one embodiment, the reaction is performed in an aqueous medium.

In one embodiment, the Fe(III) reagent is added in a plurality of approximately equal portions.

In one embodiment, the Fe(III) reagent is added in two approximately equal portions.

In one embodiment, the pH is adjusted to the desired value (e.g., by the addition of strong acid or strong base), the alkali metal sulphide is added, and one-half of the Fe(III) reagent is added. The mixture is then aerated (for example, for 1 hour), and then the remainder of the Fe(III) reagent is added.

In one embodiment, the reaction is performed at a temperature of 2 to 35° C.

In one embodiment, the reaction is performed at a temperature of 10 to 30° C.

In one embodiment, the reaction is performed for a time of 10 minutes to 12 hours.

In one embodiment, the reaction is performed for a time of 30 minutes to 6 hours.

In one embodiment, the reaction is performed for a time of about 3 hours.

In one embodiment, the reaction mixture is stirred during the reaction step.

In one embodiment, after reaction, the reaction mixture is filtered and the filtrate collected.

In one embodiment, the filtration is performed at a temperature near to the reaction temperature, to give a "hot" filtrate.

In one embodiment, the reaction mixture is first cooled, and the filtration is performed at about room temperature, to give a "cool" filtrate.

Chloride Salt Formation (CSF-2)

In this step, a 3,7-bis(disubstituted-amino)-1,9-(optionally substituted)-phenothiazin-5-ium salt, 13, is reacted with chloride, to give a 3,7-bis(disubstituted-amino)-1,9-(optionally substituted)-phenothiazin-5-ium chloride salt, 14, as illustrated in the following scheme:

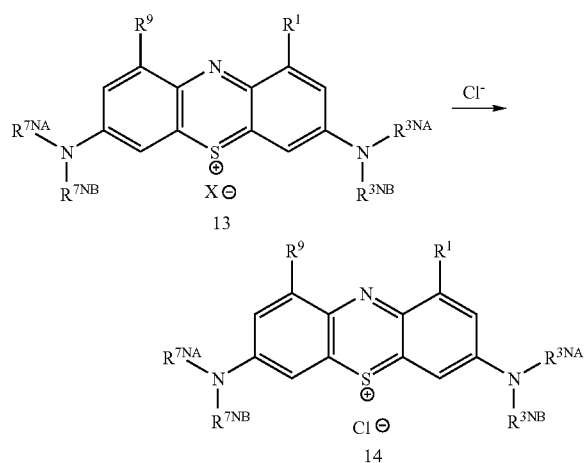

In one embodiment, a 3,7-bis(dimethylamino)-phenothiazin-5-ium salt, 13', is reacted with chloride, to give a 3,7-bis(dimethylamino)-phenothiazin-5-ium chloride salt, 14' (i.e., DEMTC), as illustrated in the following scheme:

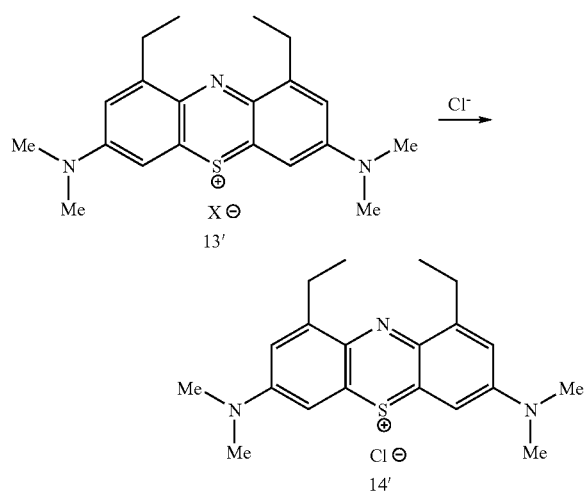

Treatment with Hydrochloric Acid as a Source of Chloride:
In one embodiment, the chloride is hydrochloric acid.
In one embodiment, the reaction is performed at a relatively low pH.
In one embodiment, the relatively low pH is −1 to 3.

In one embodiment, the relatively low pH is 0 to 3.
In one embodiment, the relatively low pH is 0 to 2.
In one embodiment, the relatively low pH is about 1.
In one embodiment, the pH is adjusted to the relatively low pH slowly.
In one embodiment, the pH is adjusted over a period of 5 to 120 minutes.
In one embodiment, the pH is adjusted over a period of 5 to 60 minutes.
In one embodiment, the pH is adjusted over a period of 5 to 30 minutes.
In one embodiment, the pH is adjusted over a period of about 10 minutes.
In one embodiment, the reaction is performed at a relatively cool temperature.
In one embodiment, the relatively cool temperature is 2 to 40° C.
In one embodiment, the relatively cool temperature is 2 to 30° C.
In one embodiment, the relatively cool temperature is 5 to 30° C.
In one embodiment, the relatively cool temperature is 10 to 30° C.
In one embodiment, the relatively cool temperature is 15 to 30° C.
In one embodiment, the relatively cool temperature is 20 to 30° C.
In one embodiment, the relatively cool temperature is about 25° C.
In one embodiment, the reaction is performed until the reaction mixture (initially, e.g., a deep blue colour) becomes light blue to colourless.
In one embodiment, the reaction mixture is stirred during the reaction step.

Treatment with a Chloride Salt as a Source of Chloride:
In one embodiment, the chloride is chloride salt.
In one embodiment, the chloride is alkali metal chloride.
In one embodiment, the chloride is sodium chloride.
In one embodiment, there is a large molar excess of (sodium) chloride.
In one embodiment, the molar ratio of chloride to salt, 13, is 5 to 100.
In one embodiment, the molar ratio is 10 to 80.
In one embodiment, the molar ratio is 10 to 50.
In one embodiment, the molar ratio is about 20.
In one embodiment, the reaction is performed in an aqueous medium.
In one embodiment, the reaction temperature is 2 to 30° C.
In one embodiment, the reaction temperature is 2 to 20° C.
In one embodiment, the reaction temperature is about 5° C.
In one embodiment, the reaction time is 5 to 30 minutes.
In one embodiment, the reaction is performed until the reaction mixture changes colour, e.g., becomes red/purple as the product precipitates.
In one embodiment, the reaction mixture is stirred during the reaction step.

If desired, one or more of the treatment steps (ST, DT, CT, EDTAT, OE) described above, may additionally be performed.

If desired, a recystallization step (RX), described above, may additionally be performed.

Synthesis Method C

This method is particularly well suited for the synthesis of diaminophenothiazinium compounds wherein the groups —N($R^{3NA}$)($R^{3NB}$) and —N($R^{7NA}$)($R^{7NB}$) are other than —N(CH$_3$)$_2$, for example, wherein the groups —N(R$^{3NA}$)(R$^{3NB}$) and —N(R$^{7NA}$)(R$^{7NB}$) are the same and are —N(CH$_3$CH$_2$)$_2$.

In one embodiment, the method comprises the steps of, in order:
thiosulfonic acid formation (TSAF-3);
oxidative coupling (OC-3);
ring closure (RC-3).

In one embodiment, the method additionally comprises the subsequent step of:
chloride salt formation (CSF-3).

Thus, in one embodiment, the method comprises the steps of, in order:
thiosulfonic acid formation (TSAF-3);
oxidative coupling (OC-3);
ring closure (RC-3);
chloride salt formation (CSF-3).

Thiosulfonic Acid Formation (TSAF-3)

In this step, an N,N-diethyl-1,4-diamino-benzene, 15, is oxidized in the presence of a thiosulfate to give a thiosulfuric acid S-(2-amino-5-diethylamino-phenyl) ester, 16, as illustrated in the following scheme:

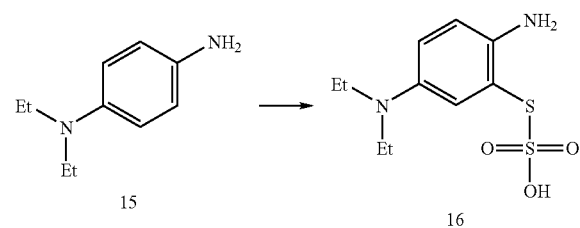

The thiosulfate is or comprises S$_2$O$_3^{-2}$.

In one embodiment, the thiosulfate is or comprises Na$_2$S$_2$O$_3$.

In one embodiment, the thiosulfate is Na$_2$S$_2$O$_3$.

Na$_2$S$_2$O$_3$ may be obtained commercially, for example, as the anhydrous salt or as the pentahydrate.

In one embodiment, the molar ratio of thiosulfate to diamine, 15, is 0.8 to 1.5.

In one embodiment, the molar ratio is 1.0 to 1.5.
In one embodiment, the molar ratio is 1.1 to 1.5.
In one embodiment, the molar ratio is 1.1 to 1.3.

In one embodiment, the oxidation is by reaction with an oxidizing agent.

In one embodiment, the oxidizing agent is or comprises Cr(VI).

In one embodiment, the oxidizing agent is or comprises Cr$_2$O$_7^{-2}$.

In one embodiment, the oxidizing agent is or comprises Na$_2$Cr$_2$O$_7$.

In one embodiment, the oxidizing agent is Na$_2$Cr$_2$O$_7$.

In one embodiment, the molar ratio of Cr(VI) to diamine, 15, is 0.2 to 2.0.

In one embodiment, the molar ratio is 0.2 to 1.0.
In one embodiment, the molar ratio is 0.2 to 0.8.
In one embodiment, the molar ratio is 0.3 to 0.7.

In one embodiment, the oxidizing agent additionally comprises Al(III).

In one embodiment, the oxidizing agent additionally comprises Al$_2$(SO$_4$)$_3$.

In one embodiment, the molar ratio of Al(III) to diamine, 15, is 0.2 to 2.0.

In one embodiment, the molar ratio is 0.2 to 1.0.

In one embodiment, the molar ratio is 0.2 to 0.8.
In one embodiment, the molar ratio is 0.3 to 0.7.
In one embodiment, the oxidizing agent further comprises a strong acid.
In one embodiment, the oxidizing agent further comprises sulfuric acid (H$_2$SO$_4$) (which has two strong acid protons).

In one embodiment, the molar ratio of acid protons to diamine, 15, is 1.0 to 4.0.
In one embodiment, the range is 1.5 to 2.5.
In one embodiment, the range is about 2.0.

In one embodiment, the reaction is performed in an aqueous medium.

In one embodiment, the reaction is performed at a temperature of 15 to 50° C.

In one embodiment, the reaction is performed for a time of 10 minutes to 2 hours.

In one embodiment, the reaction mixture is stirred during the reaction step.

In one embodiment, after reaction, the reaction mixture is filtered and the filtrate collected.

In one embodiment, the filtration is performed at a temperature near to the reaction temperature.

In one embodiment, the reaction mixture is first cooled, and the filtration is performed at about room temperature.

Oxidative Coupling (OC-3)

In this step, a thiosulfuric acid S-(2-amino-5-diethylamino-phenyl) ester, 16, is oxidatively coupled to an N,N-diethyl-aniline, 17, to give a [4-{2-(thiosulfate)-4-(diethylamino)-phenyl-imino}-cyclohexa-2,5-dienylidene]-N,N-diethyl ammonium, 18, as illustrated in the following scheme:

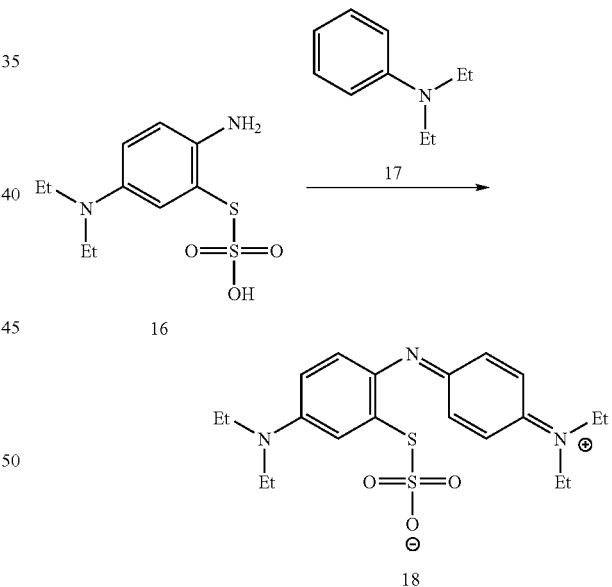

In one embodiment, the oxidation is performed using an oxidizing agent.

In one embodiment, the oxidizing agent is or comprises Cr(VI).

In one embodiment, the oxidizing agent is or comprises Cr$_2$O$_7^{-2}$.

In one embodiment, the oxidizing agent is or comprises Na$_2$Cr$_2$O$_7$.

In one embodiment, the oxidizing agent is Na$_2$Cr$_2$O$_7$.

In one embodiment, the molar ratio of ester, 16, to aniline, 17, is 0.5 to 1.5.

In one embodiment, the range is 0.8 to 1.2.
In one embodiment, the molar ratio is about 1.0.
In one embodiment, the molar ratio of Cr(VI) to aniline, 17, is 1.0 to 4.0.
In one embodiment, the range is 1.6 to 3.0.
In one embodiment, the range is 2.0 to 3.0.
In one embodiment, the molar ratio is about 2.2.
In one embodiment, the reaction is performed under acidic conditions.
In one embodiment, the reaction is performed at a pH of 1 or less.
In one embodiment, the reaction is performed at a pH of 1 to −1.
In one embodiment, the reaction is performed at a pH of 1 to 0.
In one embodiment, the acidic conditions are obtained using a strong acid.
In one embodiment, the acidic conditions are obtained using HCl (which has one strong acid proton).
In one embodiment, the molar ratio of acid protons to aniline, 17, is 1.0 to 4.0.
In one embodiment, the range is 1.5 to 2.5.
In one embodiment, the molar ratio is about 2.0.
In one embodiment, the reaction is performed in an aqueous medium.
In one embodiment, the reaction temperature is 20 to 95° C.
In one embodiment, the reaction temperature is 30 to 80° C.
In one embodiment, the reaction time is 10 minutes to 12 hours.
In one embodiment, the reaction time is 10 minutes to 4 hours.
In one embodiment, the reaction time is about 30 minutes.
In one embodiment, the reaction mixture is stirred during the reaction step.

Ring Closure (RC-3)

In this step, a [4-{2-(thiosulfate)-4-(diethylamino)-phenyl-imino}-cyclohexa-2,5-dienylidene]-N,N-diethyl ammonium, 18, is reacted with activated manganese dioxide (MnO$_2$) to achieve ring closure to give a 3,7-bis(diethylamino)-phenothiazin-5-ium salt, 19, as illustrated in the following scheme:

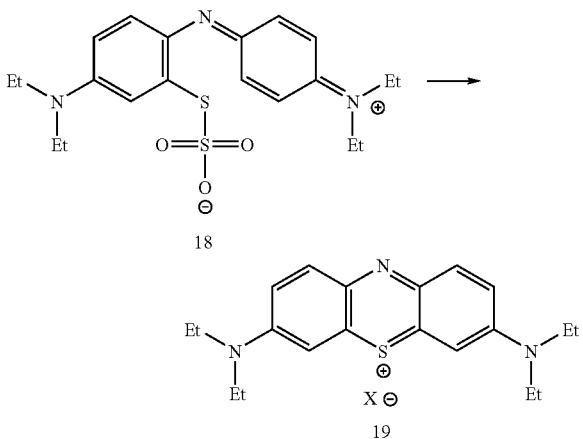

In one embodiment, the molar ratio of MnO$_2$ to ammonium, 18, is 1.0 to 3.0.
In one embodiment, the molar ratio is 1.5 to 2.5.

In one embodiment, the molar ratio is about 2.0.
In one embodiment, the reaction is performed in an aqueous medium.
In one embodiment, the reaction temperature is 30 to 95° C.
In one embodiment, the reaction temperature is 60 to 90° C.
In one embodiment, the reaction temperature is about 85° C.
In one embodiment, the reaction time is 10 minutes to 12 hours.
In one embodiment, the reaction time is 10 minutes to 4 hours.
In one embodiment, the reaction time is about 30 minutes.
In one embodiment, the reaction mixture is stirred during the reaction step.
In one embodiment, after completion of the reaction (a blue solution with precipitate is observed), strong acid (e.g., concentrated H$_2$SO$_4$) is added.

Without wishing to be bound by any particular theory, it is believed that the strong acid dissolves the manganese salts and chromium oxide (and other salts, if present).

In one embodiment, after reaction, the reaction mixture is filtered and the filtrate collected.

In one embodiment, the filtration is performed at a temperature near to the reaction temperature, to give a "hot" filtrate.

In one embodiment, the reaction mixture is first cooled, and the filtration is performed at about room temperature, to give a "cool" filtrate.

Chloride Salt Formation (CSF-3)

In this step, a 3,7-bis(diethylamino)-phenothiazin-5-ium salt, 19, is reacted with chloride, to give a 3,7-bis(diethylamino)-phenothiazin-5-ium chloride zinc chloride mixed salt, 20, as illustrated in the following scheme:

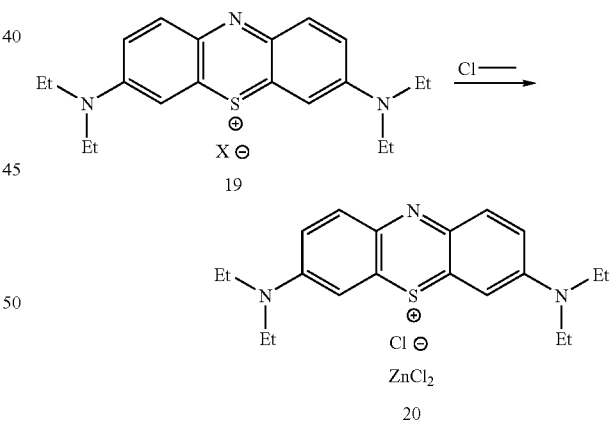

Treatment with Hydrochloric Acid as a Source of Chloride:

In one embodiment, the chloride is hydrochloric acid.
In one embodiment, the reaction is performed at a relatively low pH.
In one embodiment, the relatively low pH is −1 to 3.
In one embodiment, the relatively low pH is 0 to 3.
In one embodiment, the relatively low pH is 0 to 2.
In one embodiment, the relatively low pH is about 1.
In one embodiment, the pH is adjusted to the relatively low pH slowly.

In one embodiment, the pH is adjusted over a period of 5 to 120 minutes.

In one embodiment, the pH is adjusted over a period of 5 to 60 minutes.

In one embodiment, the pH is adjusted over a period of 5 to 30 minutes.

In one embodiment, the pH is adjusted over a period of about 10 minutes.

In one embodiment, the reaction is performed at a relatively cool temperature.

In one embodiment, the relatively cool temperature is 2 to 40° C.

In one embodiment, the relatively cool temperature is 2 to 30° C.

In one embodiment, the relatively cool temperature is 5 to 30° C.

In one embodiment, the relatively cool temperature is 10 to 30° C.

In one embodiment, the relatively cool temperature is 15 to 30° C.

In one embodiment, the relatively cool temperature is 20 to 30° C.

In one embodiment, the relatively cool temperature is about 25° C.

In one embodiment, the reaction is performed until the reaction mixture (initially, e.g., a deep blue colour) becomes light blue to colourless.

In one embodiment, the reaction mixture is stirred during the reaction step.

Treatment with a Chloride Salt as a Source of Chloride:

In one embodiment, the chloride is chloride salt.

In one embodiment, the chloride is alkali metal chloride.

In one embodiment, the chloride is sodium chloride.

In one embodiment, the chloride is alkali metal chloride and zinc chloride.

In one embodiment, the chloride is sodium chloride and zinc chloride.

In one embodiment, there is a large molar excess of (sodium and zinc) chloride.

In one embodiment, the molar ratio of chloride to salt, 19, is 5 to 100.

In one embodiment, the molar ratio is 10 to 80.

In one embodiment, the molar ratio is 10 to 50.

In one embodiment, the molar ratio is about 20.

In one embodiment, the reaction is performed in an aqueous medium.

In one embodiment, the reaction temperature is 2 to 30° C.

In one embodiment, the reaction temperature is 2 to 20° C.

In one embodiment, the reaction temperature is about 5° C.

In one embodiment, the reaction time is 30 minutes to 24 hours.

In one embodiment, the reaction mixture is stirred during the reaction step.

If desired, one or more of the treatment steps (ST, DT, CT, EDTAT, OE) described above, may additionally be performed.

If desired, a recystallization step (RX), described above, may additionally be performed.

Compounds

The methods described herein yield diaminophenothiazinium compounds at a purity that, until now, has been unavailable worldwide.

For example, many of the methods described herein yield very high purity MTC with extremely low levels of both organic impurities (e.g., of Azure B and Methylene Violet Bernthsen (MVB)) and metal impurities (e.g., meeting or exceeding the European Pharmacopoeia limits).

Thus, one aspect of the present invention pertains to a diaminophenothiazinium compound as described herein, obtained by, or obtainable by, a method as described herein.

In one embodiment, the present invention pertains to MTC obtained by, or obtainable by, a method as described herein.

In one embodiment, the compound (e.g., MTC) has a purity of greater than 98%.

In one embodiment, the compound (e.g., MTC) has a purity of greater than 97%.

In one embodiment, the compound (e.g., MTC) has a purity of greater than 96%.

In one embodiment, the compound (e.g., MTC) has a purity of greater than 95%.

In one embodiment, the compound (e.g., MTC) has a purity of greater than 94%.

In one embodiment, the compound has less than 2% Azure B as impurity.

In one embodiment, the compound has less than 3% Azure B as impurity.

In one embodiment, the compound has less than 4% Azure B as impurity.

In one embodiment, the compound has less than 0.13% MVB as impurity.

In one embodiment, the compound has less than 0.14% MVB as impurity.

In one embodiment, the compound has less than 0.15% MVB as impurity.

(All Percentage Purities Recited Herein are by Weight Unless Otherwise Specified.)

In one embodiment, the compound (e.g., MTC) has an elementals purity (e.g., for Al, Cr, Zn, Cu, Fe, Mn, Ni, Mo, Cd, Sn, and Pb) that is better than the European Pharmacopoeia (EP) limits.

The term "elementals purity" referred to herein pertains to the amounts of the eleven (11) metals specified by the European Pharmacopoeia: Al, Cr, Zn, Cu, Fe, Mn, Ni, Mo, Cd, Sn, and Pb.

The European Pharmacopoeia limits referred to herein are set out in the table below:

TABLE 1

| European Pharmacopoeia Limits (µg/g) | |
|---|---|
| Aluminium (Al) | 100 |
| Chromium (Cr) | 10 |
| Zinc (Zn) | 10 |
| Copper (Cu) | 10 |
| Iron (Fe) | 100 |
| Manganese (Mn) | 10 |
| Nickle (Ni) | 10 |
| Molybdenum (Mo) | 10 |
| Cadmium (Cd) | 1 |
| Tin (Sn) | 1 |
| Lead (Pb) | 10 |

In one embodiment, the compound (e.g., MTC) has an elementals purity that is better than 0.9 times the European Pharmacopoeia (EP) limits.

In one embodiment, the compound (e.g., MTC) has an elementals purity that is better than 0.5 times the European Pharmacopoeia (EP) limits.

In one embodiment, the compound (e.g., MTC) has an elementals purity that is better than 0.2 times the European Pharmacopoeia (EP) limits.

In one embodiment, the compound (e.g., MTC) has an elementals purity that is better than 0.1 times the European Pharmacopoeia (EP) limits.

(For example, 0.5 times the European Pharmacopoeia (EP) limits is 50 µg/g Al, 5 µg/g Cr, 5 µg/g Zn, etc.)

All plausible and compatible combinations of the above purity grades are disclosed herein as if each individual combination was specifically and explicitly recited.

Compositions

One aspect of the present invention pertains to compositions comprising a diaminophenothiazinium compound, as described herein.

One aspect of the present invention pertains to compositions comprising a diaminophenothiazinium compound which is obtained by, or is obtainable by, a method as described herein.

In one embodiment, the composition further comprises a pharmaceutically acceptable carrier, diluent, or excipient.

Methods of Inactivating Pathogens

One aspect of the present invention pertains to use of a diaminophenothiazinium compound, as described herein, in a method of inactivating a pathogen in sample (for example a blood or plasma sample) the method comprising introducing the compound into the sample, and exposing the sample to light.

One aspect of the present invention pertains to use of a diaminophenothiazinium compound, which is obtained by, or is obtainable by, a method as described herein, in a method of inactivating a pathogen in sample (for example a blood or plasma sample) the method comprising introducing the compound into the sample, and exposing the sample to light.

Methods of Medical Treatment

One aspect of the present invention pertains to a diaminophenothiazinium compound, as described herein, for use in a method of treatment (e.g., of a disease condition) of the human or animal body by therapy.

One aspect of the present invention pertains to a diaminophenothiazinium compound, which is obtained by, or is obtainable by, a method as described herein, for use in a method of treatment (e.g., of a disease condition) of the human or animal body by therapy.

One aspect of the present invention pertains to use of a diaminophenothiazinium compound, as described herein, for the manufacture of a medicament for use in the treatment of a disease condition.

One aspect of the present invention pertains to use of a diaminophenothiazinium compound, which is obtained by, or is obtainable by, a method as described herein, for the manufacture of a medicament for use in the treatment of a disease condition.

One aspect of the present invention pertains to a method of treatment of a disease condition in a patient, comprising administering to said patient a therapeutically-effective amount of a diaminophenothiazinium compound, as described herein.

One aspect of the present invention pertains to a method of treatment of a disease condition in a patient, comprising administering to said patient a therapeutically-effective amount of a diaminophenothiazinium compound, which is obtained by, or is obtainable by, a method as described herein.

Disease Conditions

In one embodiment, the disease condition is a tauopathy.

A "tauopathy" is a condition in which tau protein (and aberrant function or processing thereof) plays a role. Alzheimer's Disease is an example of a tauopathy. The pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see, e.g., Wischik et al., 2000, especially Table 5.1 therein). Each of these diseases, which is characterized primarily or partially by abnormal tau aggregation, is referred to herein as a "tauopathy."

In one embodiment, the disease condition is Alzheimer's disease (AD).

In one embodiment, the disease condition is skin cancer.

In one embodiment, the disease condition is melanoma.

In one embodiment, the disease condition is viral, bacterial or protozoal.

In one embodiment, the protozoal disease condition is malaria. In this embodiment treatment may be in combination with another antimicrobial agent e.g. in combination with chloroquine or atovaquone.

In one embodiment, the viral disease condition is caused by Hepatitis C, HIV or West Nile virus.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

The diaminophenothiazinium compound, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the diaminophenothiazinium compound to be used (e.g., administered) alone, it is often preferable to present it as a composition or formulation.

In one embodiment, the composition is a pharmaceutical composition (e.g., formulation, preparation, medicament) comprising a diaminophenothiazinium compound, as described herein, and a pharmaceutically acceptable carrier, diluent, or excipient.

In one embodiment, the composition is a pharmaceutical composition comprising at least one diaminophenothiazinium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, New York, USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled phenothiazine or phenothiazine-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Preferred Formulations

One aspect of the present invention pertains to a dosage unit (e.g., a pharmaceutical tablet or capsule) comprising 20 to 300 mg of a diaminophenothiazinium compound as described herein (e.g., obtained by, or obtainable by, a method as described herein; having a purity as described herein; etc.), and a pharmaceutically acceptable carrier, diluent, or excipient.

In one embodiment, the dosage unit is a tablet.
In one embodiment, the dosage unit is a capsule.
In one embodiment, the amount is 30 to 200 mg.
In one embodiment, the amount is about 30 mg.
In one embodiment, the amount is about 60 mg.
In one embodiment, the amount is about 100 mg.
In one embodiment, the amount is about 150 mg.
In one embodiment, the amount is about 200 mg.
In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Dosage

It will be appreciated by one of skill in the art that appropriate dosages of the diaminophenothiazinium compound, and compositions comprising the diaminophenothiazinium compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound (e.g., MTC) is administered to a human patient according to the following dosage regime: about 100 mg, 3 times daily.

In one embodiment, the active compound (e.g., MTC) is administered to a human patient according to the following dosage regime: about 150 mg, 2 times daily.

In one embodiment, the active compound (e.g., MTC) is administered to a human patient according to the following dosage regime: about 200 mg, 2 times daily.

EXAMPLES

The following are examples are provided solely to illustrate the present invention and are not intended to limit the scope of the invention, as described herein.

Example 1

Methylthioninium Chloride (MTC) 3-Pot Synthesis Using Hydrosulfite with Isolation of Intermediate To a round bottom flask (RBF) was added N,N-dimethylaniline ($C_6H_5N(CH_3)_2$, MW 121.2, 20 g, 0.165 mol), water (100 cm$^3$), and HCl (37%, 44 cm$^3$). The mixture was cooled to ~5° C. To this mixture was added dropwise an aqueous solution of sodium nitrite (NaNO$_2$, MW 69.0, 12.6 g, 0.183 mol) in water (100 cm$^3$). The resulting suspension was stirred at a low temperature (5-10° C.) for 1 hour. The mixture was cooled to approximately 5° C. Iron fillings (Fe, MW 55.85, 22.0 g, 0.40 mol) and HCl (37%, 44 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 45.0 g, 0.181 mol) in water (50 cm$^3$). A solution of sodium dichromate dihydrate (Na$_2$Cr$_2$O$_7$.2H$_2$O, MW 298.0, 20.0 g, 67.1 mmol) in water (40 cm$^3$) was added dropwise over a 40 minute period. The solution was then stirred at low temperature (about 5° C.) for 1 hour. A homogenous solution of N,N-dimethylaniline ($C_6H_5N(CH_3)_2$, MW 121.2, 20 g, 0.165 mol), water (20 cm$^3$) and H$_2$SO$_4$ (98%, 16 g) was then added to the chilled solution. Then, a solution of sodium dichromate dihydrate (Na$_2$Cr$_2$O$_7$.2H$_2$O, MW 298.0, 52.0 g, 0.174 mmol) in water (140 cm$^3$) was added dropwise over a 90 minute period. The mixture was stirred at approximately 5° C. for 2 hours. A solution of sodium hydrosulfite (Na$_2$S$_2$O$_4$, MW 174.1, 15.2 g, 87.2 mmol) in H$_2$O (20 cm$^3$) was added to the mixture. The mixture was stirred for another 10 minutes (at about 5° C.). The resulting green-brown suspension was filtered. The residue was washed with water (4×250 cm$^3$) and tetrahydrofuran (THF) (200 cm$^3$) to provide a green solid. The solid was air-dried overnight.

The solid was added to an aqueous HCl solution (900 cm$^3$, pH 2) of copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to room temperature. The mixture was filtered. The residue was washed with water (4×200 cm$^3$). The filtrate was collected. The filtrate was treated with sodium chloride (NaCl, MW 57.96, 200 g, 3.45 mol). The mixture was stirred until the deep blue colour disappeared. The mixture was filtered to provide crude methylthioninium chloride (MTC) as a solid (18.1 g, 35%).

The crude product was optionally subjected to further treatment (e.g., with sodium sulphide, etc.), as described in Examples 9 to 13, and then optionally (further) purified by recrystallisation, as described in Examples 14 and 15.

Example 2

Methylthioninium Chloride (MTC) 3-Pot Synthesis using Ethanol with Isolation of Intermediate To a round bottom flask (RBF) was added N,N-dimethylaniline ($C_6H_5N(CH_3)_2$, MW 121.2, 10 g, 82.15 mmol), water (100 cm$^3$), and HCl (37%, 22 cm$^3$). The mixture was cooled to ~5° C. To this mixture was added dropwise an aqueous solution of sodium nitrite (NaNO$_2$, MW 69.0, 6.3 g, 90.8 mmol) in water (50 cm$^3$). The resulting suspension was stirred at a low temperature (about 5° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 22.52 g, 90.75 mmol) in water (25 cm$^3$). A solution of sodium dichromate dihydrate (Na$_2$Cr$_2$O$_7$.2H$_2$O, MW 298.0, 10.0 g, 33.6 mmol) in water (20 cm$^3$) was added dropwise over a 20 minute period. The solution was then stirred at low temperature (about 5° C.) for 1 hour. A homogenous solution of N,N-dimethylaniline ($C_6H_5N(CH_3)_2$, MW 121.2.10 g, 82.15 mmol), water (10 cm$^3$) and H$_2$SO$_4$ (98%, 8 g) was then added to the chilled solution. Then, a solution of sodium dichromate dihydrate (Na$_2$Cr$_2$O$_7$.2H$_2$O, MW 298.0, 26.15 g, 87.7 mmol) in water (35 cm$^3$) was added dropwise over a 25 minute period. The mixture was stirred at approximately 5° C. for 2 hours. Ethanol ($C_2H_5OH$, MW 46.07, 1 cm$^3$, 2.4 g, 52 mmol) was added to the mixture. The mixture was stirred for another 16 hours (at 5-10° C.). The resulting green-brown suspension was filtered. The residue was washed with water (4×250 cm$^3$) and tetrahydrofuran (THF) (100 cm$^3$) to provide a green solid. The solid was air-dried overnight.

The solid was added to an aqueous HCl solution (450 cm$^3$, pH 2) of copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to room temperature. The mixture was filtered. The residue was washed with water (4×100 cm$^3$). The filtrate was collected. The filtrate was treated with sodium chloride (NaCl, MW 57.96, 100 g, 1.73 mol). The mixture was stirred until the deep blue colour disappeared. The mixture was filtered to provide crude methylthioninium chloride (MTC) as a solid.

The crude product was optionally subjected to further treatment (e.g., with sodium sulphide, etc.), as described in Examples 9 to 13, and then optionally (further) purified by recrystallisation, as described in Examples 14 and 15.

Example 3

Methylthioninium Chloride (MTC) 3-Pot Synthesis using Iodide with Isolation of Intermediate To a round bottom flask (RBF) was added N,N-dimethylaniline (C$_6$H$_5$N(CH$_3$)$_2$, MW 121.2, 10 g, 82.15 mmol), water (100 cm$^3$), and HCl (37%, 22 cm$^3$). The mixture was cooled to ~5° C. To this mixture was added dropwise an aqueous solution of sodium nitrite (NaNO$_2$, MW 69.0, 6.3 g, 90.8 mmol) in water (50 cm$^3$). The resulting suspension was stirred at a low temperature (about 5-10° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 22.52 g, 90.75 mmol) in water (25 cm$^3$). A solution of sodium dichromate dihydrate (Na$_2$Cr$_2$O$_7$.2H$_2$O, MW 298.0, 10.0 g, 33.6 mmol) in water (20 cm$^3$) was added dropwise over a 20 minute period. The solution was then stirred at low temperature (about 5° C.) for 1 hour. A homogenous solution of N,N-dimethylaniline (C$_6$H$_5$N(CH$_3$)$_2$, MW 121.2, 10 g, 82.15 mmol), water (10 cm$^3$) and H$_2$SO$_4$ (98%, 8 g) was then added to the chilled solution. Then, a solution of sodium dichromate dihydrate (Na$_2$Cr$_2$O$_7$.2H$_2$O, MW 298.0, 26.15 g, 87.7 mmol) in water (25 cm$^3$) was added dropwise over a 25 minute period. The mixture was stirred at approximately 5° C. for 2 hours. A solution of potassium iodide (KI, MW 166.01, 7.3 g, 43.6 mmol) in H$_2$O (10 cm$^3$) was added to the mixture. The mixture was stirred for another 12 hours (at room temperature). The resulting green-brown suspension was filtered. The residue was washed with water (4×250 cm$^3$) and tetrahydrofuran (THF) (100 cm$^3$) to provide a green solid. The solid was air-dried overnight.

The solid was added to an aqueous HCl solution (450 cm$^3$, pH 2) of copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to room temperature. The mixture was filtered. The residue was washed with water (4×100 cm$^3$). The filtrate was collected. The filtrate was treated with sodium chloride (NaCl, MW 57.96, 100 g, 1.73 mol). The mixture was stirred until the deep blue colour disappeared. The mixture was filtered to provide crude methylthioninium chloride (MTC) as a solid (9.1 g).

The crude product was optionally subjected to further treatment (e.g., with sodium sulphide, etc.), as described in Examples 9 to 13, and then (further) purified by recrystallisation, as described in Examples 14 and 15.

Example 4

Methylthioninium Chloride (MTC) 3-Pot Synthesis using pH Adjustment with Isolation of Intermediate To a round bottom flask (RBF) was added N,N-dimethylaniline (C$_6$H$_5$N(CH$_3$)$_2$, MW 121.2, 10 g, 82.15 mmol), water (100 cm$^3$), and HCl (37%, 22 cm$^3$). The mixture was cooled to, ~5° C. To this mixture was added dropwise an aqueous solution of sodium nitrite (NaNO$_2$, MW 69.0, 6.3 g, 90.8 mmol) in water (50 cm$^3$). The resulting suspension was stirred at a low temperature (about 5-10° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 22.52 g, 90.75 mmol) in water (25 cm$^3$). A solution of sodium dichromate dihydrate (Na$_2$Cr$_2$O$_7$.2H$_2$O, MW 298.0, 10.0 g, 33.6 mmol) in water (20 cm$^3$) was added dropwise over a 20 minute period. The solution was then stirred at low temperature (about 5° C.) for 1 hour. A homogenous solution of N,N-dimethylaniline (C$_6$H$_5$N(CH$_3$)$_2$, MW 121.2, 10 g, 82.15 mmol), water (10 cm$^3$) and H$_2$SO$_4$ (98%, 8 g) was then added to the chilled solution. Then, a solution of sodium dichromate dihydrate (Na$_2$Cr$_2$O$_7$.2H$_2$O, MW 298.0, 26.15 g, 87.7 mmol) in water (25 cm$^3$) was added dropwise over a 25 minute period. The mixture was stirred at approximately 5° C. for 2 hours (final pH 4.02 at 18° C.). The pH of the reaction mixture was adjusted to 6.0 at 8.6° C. with aqueous NaOH (10%) while keeping the temperature below 10° C. The mixture was stirred for another 16 hours at room temperature. The resulting green-brown suspension was filtered. The residue was washed with water (4×250 cm$^3$) and tetrahydrofuran (THF) (100 cm$^3$) to provide a green solid. The solid was air-dried overnight.

The solid was added to an aqueous HCl solution (450 cm$^3$, pH 2) of copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to room temperature. The mixture was filtered. The residue was washed with water (4×100 cm$^3$). The filtrate was collected. The filtrate was treated with sodium chloride (NaCl, MW 57.96, 100 g, 1.73 mol). The mixture was stirred until the deep blue colour disappeared. The mixture was filtered to provide crude methylthioninium chloride (MTC) as a solid (30%).

The crude product was optionally subjected to further treatment (e.g., with sodium sulphide, etc.), as described in Examples 9 to 13, and then optionally (further) purified by recrystallisation, as described in Examples 14 and 15.

Example 5

Methylthioninium Chloride (MTC) 2-Pot Synthesis using pH Adjustment without Isolation of Intermediate

To a round bottom flask (RBF) was added N,N-dimethylaniline ($C_6H_6N(CH_3)_2$, MW 121.2, 10 g, 82.15 mmol), water (100 cm$^3$), and HCl (37%, 22 cm$^3$). The mixture was cooled to ~5° C. To this mixture was added dropwise an aqueous solution of sodium nitrite (NaNO$_2$, MW 69.0, 6.3 g, 90.8 mmol) in water (50 cm$^3$). The resulting suspension was stirred at a low temperature (5-10° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 22.52 g, 90.75 mmol) in water (25 cm$^3$). A solution of sodium dichromate dihydrate (Na$_2$Cr$_2$O$_7$.2H$_2$O, MW 298.0, 10.0 g, 33.6 mmol) in water (20 cm$^3$) was added dropwise over a 20 minute period. The solution was then stirred at low temperature (5° C.) for 1 hour. A homogenous solution of N,N-dimethylaniline ($C_6H_5N(CH_3)_2$, MW 121.2, 10 g, 82.15 mmol), water (10 cm$^3$) and H$_2$SO$_4$ (98%, 8 g) was then added to the chilled solution. Then, a solution of sodium dichromate dihydrate (Na$_2$Cr$_2$O$_7$.2H$_2$O, MW 298.0, 26.15 g, 87.7 mmol) in water (25 cm$^3$) was added dropwise over a 25 minute period. The mixture was stirred at approximately 5° C. for 1 hour (final pH 4.51). The pH of the reaction mixture was adjusted to 6.02 at 8.6° C. with aqueous NaOH (10%) while keeping the temperature below 10° C. The mixture was stirred for another 10 minutes at this temperature (8.6° C.), before readjusting the pH to 3.80 with 10% aqueous HCl. Copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to 65° C. The mixture was filtered. The residue was washed with water (4×100 cm$^3$). The filtrate was collected. The filtrate was treated with sodium chloride (NaCl, MW 57.96, 120 g, 2.07 mol). The mixture was stirred until the deep blue colour disappeared. The mixture was filtered to provide crude methylthioninium chloride (MTC) as a solid (7.48 g, 29%).

The crude product was optionally subjected to further treatment (e.g., with sodium sulphide, etc.), as described in Examples 9 to 13, and then optionally (further) purified by recrystallisation, as described in Examples 14 and 15.

Example 6

Methylthioninium Chloride (MTC) 2-Pot Synthesis using Sodium Hydrosulfite without Isolation of Intermediate

To a round bottom flask (RBF) was added N,N-dimethylaniline ($C_6H_5N(CH_3)_2$, MW 121.2, 10 g, 82.15 mmol), water (100 cm$^3$) and HCl (37%, 22 cm$^3$). The mixture was cooled to ~5° C. To this mixture was added dropwise an aqueous solution of sodium nitrite (NaNO$_2$, MW 69.0, 6.3 g, 90.8 mmol) in water (50 cm$^3$). The resulting suspension was stirred at a low temperature (5-10° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate (Na$_2$S$_2$O$_3$.5H$_2$O, MW 248.2, 22.52 g, 90.75 mmol) in water (25 cm$^3$). A solution of sodium dichromate dihydrate (Na$_2$Cr$_2$O$_7$.2H$_2$O, MW 298.0, 10.0 g, 33.6 mmol) in water (20 cm$^3$) was added dropwise over a 20 minute period. The solution was then stirred at low temperature (5° C.) for 1 hour. A homogenous solution of N,N-dimethylaniline ($C_6H_5N(CH_3)_2$, MW 121.2, 10 g, 82.15 mmol), water (10 cm$^3$) and H$_2$SO$_4$ (98%, 8 g) was then added to the chilled solution. Then a solution of sodium dichromate dihydrate (Na$_2$Cr$_2$O$_7$.2H$_2$O, MW 298.0, 26.15 g, 87.7 mmol) in water (25 cm$^3$) was added dropwise over a 25 minute period. The mixture was stirred at approximately 5° C. for 1 hour. The filtrate was treated with sodium hydrosulfite (Na$_2$S$_2$O$_4$, MW 174.11, ~83%, 9.2 g, 43.9 mmol) in water (10 cm$^3$). The mixture was stirred for 10 minutes at ~5° C. (final pH=3.05). The pH was adjusted to 3.85 using aqueous sodium hydroxide (NaOH, 10%). Copper (II) sulfate pentahydrate (CuSO$_4$.5H$_2$O, MW 249.7, 2.06 g, 8.25 mmol). The temperature was increased to 85° C. The mixture was stirred at this temperature for 1 hour. A deep blue colour was formed. The mixture was cooled to 65° C. The mixture was filtered. The residue was washed with water (4×100 cm$^3$). The filtrate was collected. The filtrate was treated with sodium chloride (NaCl, MW 57.96, 120 g, 2.07 mol). The mixture was stirred until the deep blue colour disappeared. The mixture was filtered to provide crude methylthioninium chloride (MTC) as a solid (7.48 g, 29%).

The crude product was optionally subjected to further treatment (e.g., with sodium sulphide, etc.), as described in Examples 9 to 13, and then optionally (further) purified by recrystallisation, as described in Examples 14 and 15.

Example 7

Methylthionium Chloride (MTC) 3-Pot Synthesis using Hydrosulfite with Isolation of Intermediate

To a round bottom flask (RBF) was added N,N-dimethylaniline ($C_6H_5N(CH_3)_2$, MW 121.2, 20 g, 0.165 mol) and water (200 cm$^3$) to form a heterogeneous mixture. The mixture was cooled to ~5° C. To the cooled mixture was added HCl (37%, 44 cm$^3$) over a 10-15 minute period. To this mixture was added dropwise an aqueous solution of sodium nitrite (NaNO$_2$, MW 69.0, 12.6 g, 0.183 mol) in water (100 cm$^3$) over a 20-30 minute period. The resulting suspension was stirred at a low temperature (~5° C.) for 1 hour. The mixture was maintained at ~5° C. and HCl (37%, 44 cm$^3$) was added over a 5-10 minute period. After an additional 5 minutes of stirring, iron fillings (Fe, MW 55.85, 22.0 g, 0.40 mol) were added over a 15-20 minute periods, in order to maintain a reaction temperature below 30° C. during the addition. The mixture was stirred for 2 hours at a temperature of ~10° C. The mixture was filtered. The solid residue was washed with water (20 cm$^3$) and the filtrate collected.

The filtrate was cooled to approximately 5° C. within a 10-15 minute period. The filtrate was treated with a solution of sodium thiosulphate (Na$_2$S$_2$O$_3$.5H$_2$O, MW 248.2, 45.0 g, 0.181 mol) in water (50 cm$^3$) as one aliquot in a quick addition. A solution of sodium dichromate dihydrate ($Na_2Cr_2O_7 \cdot 2H_2O$, MW 298.0, 20.0 g, 67.1 mmol) in water (80 cm$^3$) was added dropwise over a 40 minute period. The solution was then stirred at low temperature (about 5° C.) for 1 hour. A chilled (~5° C.) homogenous solution of N,N-dimethylaniline ($C_6H_5N(CH_3)_2$, MW 121.2, 20 g, 0.165 mol), water (20 cm$^3$) and $H_2SO_4$ (98%, 16 g) was then added to the chilled reaction mixture as one aliquot, at once. (Preparation of the solution prior to addition: N,N-dimethylaniline and water were cooled in an ice bath to approximately 5° C., and then concentrated sulphuric acid was slowly added over a 15-25 minute period in order to prevent thermal run away of the exothermic reaction.) Then, a solution of sodium dichromate dihydrate ($Na_2Cr_2O_7 \cdot 2H_2O$, MW 298.0, 52.0 g, 0.174 mmol) in water (140 cm$^3$) was added dropwise over a 90 minute period. The reaction mixture was stirred at approximately 5° C. for 2 hours. A solution of sodium hydrosulfite ($Na_2S_2O_4$, MW 174.1, 15.2 g, 87.2 mmol) in $H_2O$ (20 cm$^3$) was added to the mixture as one aliquot in one quick addition. The mixture was stirred for another 10 minutes (at about 5° C.). The resulting green-brown suspension was filtered. The residue was washed with water (2×250 cm$^3$) to provide a green solid. The solid was air-dried overnight.

The solid was added to an aqueous HCl solution (900 cm$^3$, pH 2) to form a suspension. Copper (II) sulfate pentahydrate ($CuSO_4 \cdot 5H_2O$, MW 249.7, 4.12 g, 16.5 mmol) was added as one aliquot in a quick addition. The temperature was increased to 85° C. over a 15-20 minute period. The mixture was stirred at this temperature for 1 hour. A deep blue colour was formed. The mixture was cooled to room temperature over a 30 minute period, and the mixture was filtered. (In an alternative example, the mixture was filtered at about 60° C.; however, the filtrate can bump under the reduced vacuum.) The residue was washed with water (2×200 cm$^3$). The filtrate was collected. The filtrate was heated to 65° C. over a 25-30 minute period. The (hot) filtrate was treated with sodium chloride (NaCl, MW 57.96, 200 g, 3.45 mol), and allowed to cool to 22° C. over a 3.5 hour period. Crystalline product was first observed after about 2.5 hours and at about 40° C. The mixture was filtered to provide crude methylthionium chloride (MTC) as a solid (On this scale: 18-24 g or 35%; on a 5 L scale: 60-65 g or >30%).

The crude product was optionally subjected to further treatment (e.g., with sodium sulphide, etc.), as described in Examples 9 to 13, and then optionally (further) purified by recrystallisation, as described in Examples 14 and 15.

Example 8

Methylthioninium Chloride (MTC) 3-Pot Synthesis with Isolation of Intermediate

To a round bottom flask (RBF) was added N,N-dimethylaniline ($C_6H_5N(CH_3)_2$, MW 121.2, 10 g, 82.15 mmol), water (100 cm$^3$), and HCl (37%, 22 cm$^3$). The mixture was cooled to ~5° C. To this mixture was added dropwise an aqueous solution of sodium nitrite ($NaNO_2$, MW 69.0, 6.3 g, 90.8 mmol) in water (50 cm$^3$). The resulting suspension was stirred at a low temperature (5-10° C.) for 1 hour. The mixture was cooled to approximately 5° C. Iron fillings (Fe, MW 55.85, 11.0 g, 197 mmol) and HCl (37%, 22 cm$^3$) were added in one aliquot portions. The mixture was stirred for 2 hours at a temperature below 30° C. The mixture was filtered, and the filtrate collected.

The filtrate was cooled to approximately 5° C. The filtrate was treated with a solution of sodium thiosulfate pentahydrate ($Na_2S_2O_3 \cdot 5H_2O$, MW 248.2, 22.52 g, 90.75 mmol) in water (25 cm$^3$). A solution of sodium dichromate dihydrate ($Na_2Cr_2O_7 \cdot 2H_2O$, MW 298.0, 10.0 g, 33.6 mmol) in water (20 cm$^3$) was added dropwise over a 20 minute period. The solution was then stirred at low temperature (about 5° C.) for 1 hour. A homogenous solution of N,N-dimethylaniline ($C_6H_5N(CH_3)_2$, MW 121.2, 10 g, 82.15 mmol), water (10 cm$^3$) and $H_2SO_4$ (98%, 8 g) was then added to the chilled solution. Then, a solution of sodium dichromate dihydrate ($Na_2Cr_2O_7 \cdot 2H_2O$, MW 298.0, 26.15 g, 87.7 mmol) in water (35 cm$^3$) was added dropwise over a 25 minute period. The mixture was stirred at approximately 5° C. for 2 hours. The resulting green-brown suspension was filtered. The residue was washed with water (4×250 cm$^3$) and tetrahydrofuran (THF) (100 cm$^3$) to provide a green solid. The solid was air-dried overnight.

The solid was added to an aqueous HCl solution (455 cm$^3$, pH 2) of copper (II) sulfate pentahydrate ($CuSO_4 \cdot 5H_2O$, MW 249.7, 2.06 g, 8.25 mmol). The temperature was increased to 85° C. The mixture was stirred at this temperature for 1 hour. A deep blue colour was formed. The mixture was cooled to room temperature. The mixture was filtered. The residue was washed with water (4×100 cm$^3$). The filtrate was collected. The filtrate was treated with sodium chloride (NaCl, MW 57.96, 100 g, 1.73 mol). The mixture was stirred until the deep blue colour disappeared. The mixture was filtered to provide crude methylthioninium chloride (MTC) as a solid (15.3 g, 58%).

The crude product was optionally subjected to further treatment (e.g., with sodium sulphide, etc.), as described in Examples 9 to 13, and then optionally (further) purified by recrystallisation, as described in Examples 14 and 15.

Example 9

Treatment of Crude Product with Sodium Sulphide

Crude MTC product (MW 373.90, 4.5 g, ~12.0 mmol) was fully dissolved in $H_2O$ (125 cm$^3$) at 65° C. The solution was cooled to room temperature. The cooled solution was clarified by filtration to ensure complete dissolution. The solution was treated with a solution of sodium sulphide ($Na_2S$, MW 78.04, >60%, 200 mg, 1.54 mmol, 0.1 equivalent) in $H_2O$ (10 cm$^3$). The resulting mixture was stirred for 10 minutes. The mixture was filtered by vacuum filtration. The filtrate was collected. Sodium chloride (NaCl, MW 57.96, 16 g, 0.276 mol) was added to the filtrate while stirring. The resulting precipitate was collected by vacuum filtration.

Example 10

Treatment of Crude Product with Sodium Sulphide

Crude MTC product (MW 373.90, 5 g, ~13.3 mmol) was fully dissolved in $H_2O$ (230 cm$^3$) at 60° C. The solution was cooled to room temperature. The solution was treated with a solution of sodium sulphide ($Na_2S$, MW 78.04, >60%, 135 mg, ~1.0 mmol, ~0.07 equivalent) in $H_2O$ (20 cm$^3$). The resulting mixture was stirred for 15 minutes. The mixture was filtered by vacuum filtration. The filtrate was collected. The pH of the filtrate was 10.5±0.5. The filtrate was washed with dichloromethane (DCM) (5×100 cm$^3$). The pH of the washed filtrate was adjusted from ~9.5-10.2 to 5.0. The solution was then heated to 60° C. Sodium chloride (NaCl, MW 57.96, 200 g, 3.45 mol) was slowly added to the (hot) solution. (Caution must be exercised because residual DCM may cause the solution to bump.) Slow cooling (in excess of 3.5 hours) caused methylthioninium chloride (MTC) to precipitate in a

Example 11

Treatment of Crude Product with Dimethyldithiocarbamic Acid Sodium Salt

Crude MTC product (MW 373.90, 4.5 g, ~12.0 mmol) was fully dissolved in $H_2O$ (125 cm$^3$) at 65° C. The solution was cooled to room temperature. The cooled solution was clarified by filtration to ensure complete dissolution. The solution was treated with a solution of dimethyldithiocarbamic acid, sodium salt ($(CH_3)_2NCS_2Na$, MW 143.21, 550 mg, 3.84 mmol, 0.1 equivalent) in $H_2O$ (10 cm$^3$). The resulting mixture was stirred for 10 minutes. The mixture was filtered by vacuum filtration. The filtrate was collected. Sodium chloride (NaCl, MW 57.96, 16 g, 0.276 mol) was added to the filtrate while stirring. The resulting precipitate was collected by vacuum filtration.

Example 12

Treatment of Crude Product with Sodium Carbonate

Crude MTC product (MW 373.90, 4.5 g, ~12.0 mmol) was fully dissolved in $H_2O$ (125 cm$^3$) at 65° C. The solution was cooled to room temperature. The cooled solution was clarified by filtration to ensure complete dissolution. The solution was treated with a solution of sodium carbonate ($Na_2CO_3$, MW 105.99, 163 mg, 0.154 mmol, 0.1 equivalent) in $H_2O$ (10 cm$^3$). The resulting mixture was stirred for 10 minutes. The mixture was filtered by vacuum filtration. The filtrate was collected. Sodium chloride (NaCl, MW 57.96, 16 g, 0.276 mol) was added to the filtrate while stirring. The resulting precipitate was collected by vacuum filtration.

Example 13

Treatment of Crude Product with EDTA Disodium Salt

Crude MTC product (MW 373.90, 10.0 g, ~26.7 mmol) was fully dissolved in $H_2O$ (270 cm$^3$). Ethylenediaminetetraacetic acid (EDTA) disodium salt dihydrate (MW 372.24, 1 g, 2.68 mmol, 0.1 equivalents) was added. The mixture was stirred at 65° C. for approximately 1 hour. The mixture was filtered by vacuum filtration. The filtrate was collected. Sodium chloride (NaCl, MW 57.96, 16 g, 0.276 mol, 10 equivalents) was added to the filtrate while stirring. The resulting precipitate was collected by vacuum filtration.

Example 14

Recrystallisation by Cool Acidic Recrystallisation

Crude MTC product or treated crude MTC product (MW 373.90, 20 g, ~53.4 mmol) was dissolved in $H_2O$ (1700 cm$^3$) at 65° C. The mixture was allowed to cool to 22° C. The pH was adjusted to pH 1 using aqueous HCl, generating a suspension which could be filtered. The resulting highly crystalline product was collected by vacuum filtration, and dried in an oven at 75° C. for 16 hours.

Example 15

Recrystallisation by Hot Salting Out

Crude MTC product or treated crude MTC product (MW 373.90, 20 g, ~53.4 mmol) was dissolved in $H_2O$ (1700 cm$^3$) at 65° C. Sodium chloride (NaCl, MW 57.96, 200 g, 3.45 mol) was added. The mixture was allowed to cool slowly to 22° C. over 3.5 hours. The resulting highly crystalline product was collected by vacuum filtration, and dried in an oven at 75° C. for 16 hours.

Example 16

Recrystallisation using THF/$H_2O$

Crude MTC product or treated crude MTC product (MW 373.90, 10 g, ~26.7 mmol) was dissolved in $H_2O$ (200 cm$^3$) at 65° C. The solution was cooled to approximately 22° C. Tetrahydrofuran (THF) (40 cm$^3$) was added. The solution was allowed to cool slowly to approximately 5° C. in an ice bath over several hours. The resulting highly crystalline product was collected by vacuum filtration, and dried in an oven at 100° C. for 2 hours.

Example 17

Methylthioninium Chloride (MTC) The Synthesis, Treatment, and Recrystallisation of MTC N,N-Dimethylaniline (20.0 g, 165 mmol) was placed in the reaction vessel [V1] and stirred. To this vessel was added $H_2O$ (200 cm$^3$) in one aliquot over 1 minute, and the heterogeneous mixture was cooled to 5° C. (±2° C.) over a 15 minute period (±5 minutes) using an ice/water bath. 37% Hydrochloric acid (44 cm$^3$) was added over a 5 minute period (±2 minutes) with an observable temperature rise from 4° C. to 8° C. (±2° C.). (Caution: exothermic reaction.) The reaction vessel was maintained at 5° C. (±2° C.) for an additional 5 minutes period (±2 minutes) to ensure a complete homogenous mixture. Stirring was continuous throughout this process.

Separately the $NaNO_2$ solution was prepared. $NaNO_2$ (12.6 g, 182.6 mmol) was quickly added over 1 minute to a separate flask containing stirred $H_2O$ (100 cm$^3$). The resulting dissolving process is endothermic and a temperature drop from 20° C. to 17° C. (±2° C.) was observed. The complete dissolution took 5 minutes (±2 minutes). An overall volume of approximately 110 cm$^3$ resulted.

The sodium nitrite solution was slowly added dropwise to the reaction vessel [V1] over a 20 minute period (±5 minutes) and a rise in reaction temperature from 5° to 9° C. was observed during the addition. (Caution: exothermic reaction.) An orange colour was observed once the addition began. The reaction mixture was stirred for an additional 60 minutes (±5 minutes) whilst maintaining the temperature at 5° C. (±2° C.) using the ice/water bath. At this stage in the reaction, an orange solution with a lighter coloured precipitate was observed. A small amount of foam was also formed.

37% Hydrochloric acid (44 cm$^3$) was added to the reaction mixture [V1] over a 5 minute period (±2 minutes) with an observable reaction temperature rise from 5° C. to 8° C. (Caution: exothermic reaction.) The reaction mixture was stirred for another 5 minutes (±2 minutes) once addition was complete. Iron fillings (22.0 g, 0.394 mol) were added to the reaction vessel in aliquots of approximately 2 g over a period of 15 minutes (±5 minutes). A temperature rise from 8° C. to 12° C. was observed during the iron addition. (Caution: exothermic reaction.) (Caution: orange fumes are formed; gas is evolved.) The reaction mixture was stirred for an additional 120 minutes (±10 minutes), whilst a reaction temperature of approximately 10° C. (±2° C.) was maintained using the ice/water bath.

The excess iron fillings were collected by vacuum filtration over Celite® over a 5 minute period (±2 minutes), and the remaining solid in the filter funnel was washed with $H_2O$ (20 $cm^3$).

The filtrate (a clear brown liquid) was retained and contained the desired N,N-dimethyl-p-phenylenediamine dihydrochloride salt. The total volume of filtrate was approximately 400 $cm^3$. The pH of the solution at this stage was 2.59 at 20° C. The solution was monitored using ultraviolet spectrophotometry throughout the reaction in order to confirm reaction completion and to calculate the final concentration of the N,N-dimethyl-p-phenylenediamine. Typical conversion was 82%±2%).

The filtrate was placed in another reaction vessel [V2] and cooled to 5° C. (+2° C.) over a period of 15 minutes (±5 minutes) using an ice/water bath.

Separately a solution of $Na_2S_2O_3.5H_2O$ was prepared. $Na_2S_2O_3.5H_2O$ (45.0 g, 181.4 mmol) was added in one aliquot to stirred $H_2O$ (50 $cm^3$) over one minute. The resulting dissolution was endothermic and a temperature drop from 22° C. to 10° C. was observed. This mixture was then stirred for 15 minutes (±5 minutes) to ensure complete dissolution. An overall volume of 76 $cm^3$ resulted.

The $Na_2S_2O_3.5H_2O$ solution was added in one aliquot over a 1 minute period to the reaction mixture in [V2]. The reaction mixture was stirred for an additional 5 minutes (±2 minutes) while maintaining the reaction temperature at 5° C. (±2° C.).

Separately a solution of $Na_2Cr_9O_7.2H_2O$ was prepared. $Na_2Cr_2O_7.2H_2O$ (20.0 g, 67.2 mmol) was added to stirred $H_2O$ (80 $cm^3$) over one minute as one aliquot. The resulting dissolution was endothermic and a temperature drop from 22° C. to 15° C. The mixture was then stirred for 15 minutes (±5 minutes) to ensure complete dissolution. The $Na_2Cr_2O_7.2H_2O$ solution was added slowly to the reaction mixture in [V2] over a 30 minute period (±5 minutes), in order to maintain a reaction temperature of 5° C. to 8° C. (±2° C.). (Caution: exothermic reaction.) The reaction mixture was then stirred for 60 minutes whilst maintaining the reaction temperature at 5° C. (±2° C.) using an ice/water bath.

Separately a solution of N,N-dimethylaniline was prepared. N,N-Dimethylaniline (20.0 g, 165 mmol) was added in one aliquot over 1 minute to a flask containing stirred $H_2O$ (20 $cm^3$). The heterogeneous mixture was cooled to 5° C. (±2° C.) over 15 minutes (±5 minutes) using an ice/water bath, and concentrated (98%) sulphuric acid (16.0 g) was slowly added over a 25 minute period (±5 minutes) to prevent a rapid temperature rise. A temperature rise from 3° C. to 21° C. was observed. (Caution: exothermic reaction.) Upon completion of the acid addition, the mixture was stirred for a further 10 minutes (±5 minutes) to ensure a complete homogenous mixture. This mixture was maintained at 5° C. (±2° C.) until addition to the main reaction vessel [V2]. The overall volume was approximately 48 $cm^3$.

The chilled acidified aqueous N,N-dimethylaniline mixture at 5° C. (±2° C.) was added to the reaction mixture in [V2] as one aliquot over a 1 minute period. The reaction mixture was then stirred for another 5 minutes (±2 minutes) whilst being maintained at 5° C. (±2° C.). No temperature changes were observed with this addition to the main reaction mixture.

Separately a $Na_2Cr_2O_7.2H_2O$ solution was prepared. $Na_2Cr_2O_7.2H_2O$ (52.0 g, 174.4 mmol) was added to a flask containing stirred $H_2O$ (140 $cm^3$) over a 1 minute period.

The $Na_2Cr_2O_7.2H_2O$ solution was added dropwise to the reaction mixture in [V2] over a 90 minute period (±2 minutes), resulting in a temperature rise in the reaction from 5° C. to 10° C. (±2° C.). (Caution: exothermic reaction.) A green precipitate was formed upon addition of the $Na_2Cr_2O_7.2H_2O$ solution. The reaction mixture was stirred for 120 minutes whilst being maintained at 5° C. (+2° C.). The reaction mixture now resembled a dark green slurry. The thiosulphonic acid of Bindschedler Green is the green precipitate in the solution at this stage. The waste effluent (filtrate) was monitored at this point to determine the levels of chromium(VI). By titration with ammonium iron(II) sulphate (0.1 M) in the presence of perchloric acid and sulphuric acid, the levels of Cr(VI) can be calculated so that the effluent can be treated appropriately.

Separately a solution of $Na_2S_2O_4$ was prepared. $Na_2S_2O_4$ (15.2 g, 87.2 mmol) was added to a flask containing stirred $H_2O$ (20 $cm^3$) in one aliquot over a 1 minute period. This mixture was stirred for an additional 30 minutes (±5 minutes) to ensure complete dissolution.

The $Na_2S_2O_4$ solution was added to the reaction mixture [V2] as one aliquot over a 1 minute period, during which no temperature changes were observed. After completion of this addition, the reaction mixture was left to stir for a further 5 minutes (±2 minutes).

The reaction mixture in [V2] was then filtered through a Büchner funnel under vacuum over a 30 minute period (±5 minutes). The solid was removed from the filter funnel and placed in a new vessel with addition of fresh water (250 $cm^3$). This mixture was vigorously stirred for 15 minutes and filtered. The solid was again removed from the filter funnel, placed in a separate vessel with fresh water (250 $cm^3$), stirred, and filtered. All washings were discarded.

The solid thiosulphonic acid of Bindschedler Green collected in the filter funnel was broken up into small pieces and placed in a new clean reaction vessel [V3].

Separately $H_2O$ (900 $cm^3$) was pH adjusted to pH 2.0 (±0.2) using 5 $cm^3$ (±1 $cm^3$) 5 M hydrochloric acid. This acidified water was then added to the reaction vessel containing the thiosulphonic acid of Bindschedler Green in [V3] over a 1 minute period. The content of this vessel [V3] was then stirred. The thiosulphonic acid of Bindschedler Green was suspended in the acidified water [V3]. To this suspension [V3] was added $CuSO_4.5H_2O$ (4.0 g, 16.0 mmol) in one aliquot over a 1 minute period. No exothermic reaction was observed on this scale. The reaction vessel [V3] was then heated to 85° C. (±2° C.) over a 25 minute period (±5 minutes). A blue colour was first observed at 40° C. (±2° C.). Once 85° C. (±2° C.) had been achieved, the reaction vessel [V3], stirring was continued at this temperature for 60 minutes. The vessel [V3] was then cooled over a 20 minute period (±5 minutes) to 60° C. (±2° C.) and the contents were filtered through a Büchner funnel under vacuum over a 20 minute period (±5 minutes). The solid was then washed with fresh water (200 $cm^3$). The solid waste was discarded safely. Because approximately 68 g waste solid (dry weight of solid waste) was observed on a 10 g scale, approximately 146 g waste solid was anticipated. The water washing and filtrate were combined and were ready for purification. The filtrate and washing contain the desired MTC in solution.

The deep blue aqueous filtrate containing the MTC was heated to 65° C. (±2° C.) over a 25 minute period (±5 minutes) and sodium chloride (200 g, 342 mmol) was added over a 10 minute period (±2 minutes). The solution was cooled to 25° C. (±2° C.) over a 360 minute period (±5 minutes) to yield the product as a blue green solid. (Total crude mass of 24.1 g, approximately 40%.)

Alternatively: Hydrochloric acid (15 cm³, 5 M) was added to the deep blue aqueous filtrate containing the MTC, currently at 25° C., over a 10 minute period (±2 minutes) in order to reach pH 1; this generated a suspension. The suspension was heated to 65° C. (±2° C.) over a 25 minute (±5 minutes) and was cooled to 20° C. (±2° C.) over a 360 minute period (±5 minutes) to yield the product as a blue green solid. (Total crude mass of 24.1 g, approximately 40%.) Even this relatively crude product usually has a lower metal content purer than commercially available MTC.

Alternatively: The MTC was then crystallised out of solution by the slow addition of hydrochloric acid (1 M) to reach pH 1. The solid MTC was collected by filtration. Any residual MTC in the filtrate can be recovered with the addition of NaCl.

The product was then subjected to treatment and organic extraction.

MTC (5 g, obtained from the procedure described above) was placed in a vessel, containing water (230 cm³), and heated to 65° C. (±5° C.) over a 20 minute period (±5 minutes) with stirring. Stirring was continued at this temperature for an additional 1 hour (±10 minutes), and the reaction mixture was then cooled to 10° C. (±2° C.) over a 30 minute period (±5 minutes).

Separately a solution of $Na_2S$ was prepared. Sodium sulphide (135 mg) was fully dissolved in water (20 cm³) over a 10 minute period (±5 minutes) whilst being stirred. (Sodium Sulphide has a Strong Repugnant Smell.)

The cooled MTC solution at 10° C. (±2° C.) was treated with the prepared sodium sulphide solution in one aliquot, at once. The combined solutions were stirred for 15 minutes (±5 minutes) while maintaining a temperature of 10° C. (±2° C.) and then the resulting precipitate was removed by filtration. (This removes the complexed metals.) The metal-free MTC is now present in solution in the filtrate liquor.

The pH of the MTC filtrate was approximately 10.8, and if not, it was adjusted to have a pH of approximately 10.8 using aqueous $Na_2S$ solution. The cool MTC solution at 10° C. (±2° C.) was placed in a reaction vessel equipped with an overhead mechanical stirrer attached to a shaft with a paddle as well as a run-off tap at the bottom of the flask. Once the MTC solution (filtrate liquor) was in the vessel, dichloromethane (50 cm³) (Caution: Non-flammable, volatile) is also added to the same vessel and the heterogeneous mixture was stirred for 10 minutes. (The dichloromethane is immiscible in water and forms a separate layer below the water layer containing the MTC.) The lower dichloromethane layer was run-off once separated from the aqueous MTC layer. (The interface is impossible to see; however, the DCM layer is purple and once it has come out of the tap, a clear distinction can be made between that and the dark blue/black aqueous MTC layer.) This addition of dichloromethane, 10 minute stir, and run-off of the lower layer, was repeated four more times, and the temperature was maintained at 10° C. (±2° C.) throughout this extraction process. (The Azure B is removed with the DCM.) The total volume of dichloromethane was 250 cm³.

The deep blue top MTC aqueous layer was now pH adjusted from 9.9 to 5.0 using 10% hydrochloric acid. The MTC solution was then heated to 65° C. (±5° C.) over a 20 minute period (±5 minutes), whilst stirred. Sodium chloride (42 g) was added to the MTC solution, followed immediately by cooling to 25° C. (±2° C.) over a 360 minute period (±5 minutes). The metal-free highly pure MTC precipitated out of solution and was recovered by filtration to give a blue green solid (4.7-4.9 g, 96%±2%).

Alternatively: Hydrochloric acid (15 cm³, 5 M) was added to the deep blue top MTC aqueous layer over a 10 minute period (±2 minutes) in order to reach pH 1; this generated a suspension. The suspension was heated to 65° C. (±2° C.) over a 25 minute period (±5 minutes) and was cooled to 20° C. (±2° C.) over a 360 minute period (±5 minutes) to yield metal-free highly pure MTC as a blue green solid.

Alternatively: The deep blue top MTC aqueous layer was pH adjusted to between pH 3.5-4.5 and the temperature allowed to rise to 25° C. The MTC was then crystallised out of solution by slow addition of hydrochloric acid (1 M) to reach pH 1. The solid MTC was collected by filtration to yield metal-free highly pure MTC as a blue green solid. Any residual MTC in the filtrate can be recovered with the addition of NaCl.

An MTC sample was prepared using the method described in Example 1. The crude product (CM-pd-378) was then crystallised using cool acid re-crystallisation as described in Example 17. The material was then further purified by organic extraction and recrystallised using HCl at 25° C., also as described in Example 17. This yielded highly pure MTC with an organic purity of 98.53% based upon HPLC analyses. The purity data are summarised in the following Table.

TABLE 2

Organic Purity of Synthesized and Purified MTC as Determined by HPLC Analysis

| MTC Source | MTC % | Azure B % | MVB % | Others % |
|---|---|---|---|---|
| Medex ™ | 94.22 | 5.24 | 0.10 | 0.44 |
| CM-pd-378 | 96.60 | 2.89 | 0.33 | 0.06 |
| CM-pd-378b | 98.53 | 1.29 | 0.14 | 0.04 |

Notes:
Medex ™: obtained from Medex Medical Export Co. Ltd. for comparison purposes.
CM-pd-378: crude MTC prepared according to Example 1, then precipitated from $H_2O$/HCl (pH 1); T = 25° C.
CM-pd-378b: pure MTC prepared from crude MTC (CM-pd-378 treated with $Na_2S$ and treated/washed/extracted with DCM at 10° C. and then MTC recrystallised from the aqueous layer using HCl (pH 1); T = 10-25° C.).

Example 18

Ethylthioninium Chloride (ETC) SYNTHESIS using Sodium Sulphide and Iron(III) Chloride N,N-diethyl-p-phenylenediamine ($H_2C_6H_4N(CH_2CH_3)_2$, MW 164.25, 40 g, 244 mmol) was dissolved in diethyl ether (200 cm³). Hydrochloric acid (40 cm³, 37%) was added. The resulting solution was concentrated by rotary evaporation to give N,N-diethyl-p-phenylenediamine dihydrochloride as a light brown solid (57.76 g, 100%). $\delta_H$ (250 MHz; $D_2O$): 7.68 (2H, m, ArH), 3.45 (4H, q, 7.25, $NCH_2$), 1.19 (6H, t, 7.25, $CH_3$).

N,N-diethyl-p-phenylenediamine dihydrochloride ($H_2C_6H_4N(CH_2CH_3)$.2HCl, MW 237.17, 57.76 g, 244 mmol) was dissolved in water (1200 cm³). The pH was adjusted to pH 1.6 using 10% aqueous HCl. A pink colour was formed. Sodium sulphide ($Na_2S$, MW 78.04, 32 g, >60%, 244 mmol) was added. A light yellow solution with a green precipitate was formed. An aqueous solution of iron(III) chloride hexahydrate ($FeCl_3.6H_2O$, MW 270.30, 98.75 g, 365 mmol) in water (400 cm³) was added to the mixture. There was an immediate colour change to blue. The mixture was then aerated for 1 hour. A second aqueous solution of iron(III) chloride hexahydrate ($FeCl_3.6H_2O$, MW 270.30, 98.75 g, 365 mmol) in water (400 cm³) was added to the mixture. The solution was cooled to 5° C. The mixture was filtered. The residue was washed with water. The filtrate was collected. Sodium chloride (NaCl, MW 57.96, 400 g, 6.9 mol) was added to the filtrate. The mixture was stirred for 10 minutes. The colour changed to red/purple as a precipitate was formed. The mixture was filtered and the solid residue collected. The solid was dissolved in dichloromethane ($CH_2Cl_2$, 1000 cm³) and methanol ($CH_3OH$, 100 cm³) and dried over magnesium sulfate (MgSO$_4$). The mixture was filtered, and the filtrate concentrated to give the product, ethylthioninium chloride (ETC) (MW 375.96, 4.28 g, 11.4 mmol, 9.3%) as a green solid. δ$_H$ (250 MHz; D$_2$O): 7.35 (2H, d, ArH), 7.04 (2H, d, ArH), 6.86 (2H, s, ArH), 3.45 (8H, q, 7.25, NCH$_2$), 1.19 (12H, t, 7.25, CH$_3$).

Flash column chromatography may be performed in order to remove residual iron chloride, using, for example, an eluent of 10% methanol: 90% dichloromethane with silica 40-63 μm 60 Å.

Example 19

1,9-Diethyl Methylthioninium Chloride (DEMTC) Synthesis using Sodium Sulphide and Iron(III) Chloride To a 100 cm$^3$ round bottom flask was added 3-ethylaniline (H$_2$C$_6$H$_4$CH$_2$CH$_3$, MW 121.18, 10 g, 82.5 mmol), ethanol (15 cm$^3$), and sodium carbonate (Na$_2$CO$_3$, MW 105.99, 11.81 g, 111.4 mmol). Methyl iodide (CH$_3$I, MW 141.94, 31.63 g, 222 mmol) was added dropwise. The mixture was then heated at 45° C. for 10 hours. The mixture was then cooled to room temperature. Water (100 cm$^3$) was added. The mixture was extracted into diethyl ether (3×100 cm$^3$) and the extracts were dried over magnesium sulfate (MgSO$_4$). The mixture was filtered and the filtrate concentrated to give the product, N,N-dimethyl-m-ethylaniline ((CH$_3$)$_2$NC$_6$H$_4$CH$_2$CH$_3$, MW 149.23, 4.68 g, 31.3 mmol, 38%) as a light yellow oil. δ$_H$ (250 MHz; CDCl$_3$): 7.22 (1H, t, 7.75, ArH), 6.63 (3H, m, ArH), 2.97 (6H, s, NCH$_3$), 2.63 (2H, q, 7.5, CH$_2$), 1.27 (3H, t, 7.5, CH$_3$); δ$_C$ (62.9 MHz; CDCl$_3$): 15.8 (CH$_3$), 29.5 (NCH$_2$), 40.8 (NCH$_3$), 110.3 (ArC), 112.4 (ArC), 116.5 (ArC), 129.1 (ArC), 145.3 (ArC), 150.9 (ArC).

To a 250 cm$^3$ round bottom flask was added N,N-dimethyl-m-ethylaniline ((CH$_3$)$_2$NC$_6$H$_4$CH$_2$CH$_3$, MW 149.23, 4.68 g, 31.3 mmol), water (100 cm$^3$), and hydrochloric acid (HCl, 8.5 cm$^3$, 37%). The solution was cooled to 5° C. A solution of sodium nitrite (NaNO$_2$, MW 69.0, 2.46 g, 35.7 mmol) in water (80 cm$^3$) was then added dropwise. The mixture was stirred for 3 hours at room temperature. Iron fillings (Fe, MW 55.85, 5.24 g, 94 mmol) and hydrochloric acid (HCl, 8.5 cm$^3$, 37%) were added. The mixture was stirred at room temperature for 3 hours. The mixture was filtered, and the filtrate collected. The pH of the filtrate was adjusted to pH 7 using sodium bicarbonate (NaHCO$_3$) solution, and extracted into ethyl acetate (3×50 cm$^3$). The combined extracts were dried over magnesium sulfate (MgSO$_4$). The mixture was filtered and the filtrate concentrated to yield a brown oil. The oil was dissolved in diethyl ether/ethanol (1:1) (175 cm$^3$). Hydrochloric acid (HCl, 5 cm$^3$, 37%) was added. The solution was filtered to give the product, N,N-dimethyl-m-ethyl-p-phenylenediamine dihydrochloride ((CH$_3$)$_2$NC$_6$H$_4$(CH$_2$CH$_3$)NH$_2$.2HCl, MW 237.17, 4.44 g, 1.87 mmol, 60%) as a light brown solid. δ$_H$ (250 MHz; D$_2$O): 7.66 (1H, s, ArH), 7.56 (2H, s, ArH), 3.29 (6H, s, NCH$_3$), 2.74 (2H, q, 7.5, CH$_2$), 1.25 (3H, t, 7.5, CH$_3$); δ$_C$ (62.9 MHz; CDCl$_3$): 15.5 (CH$_3$) 25.6 (NCH$_2$), 48.9 (NCH$_3$), 122.1 (ArC), 124.6 (ArC), 128.1 (ArC), 132.6 (ArC), 143.3 (ArC), 144.9 (ArC).

N,N-dimethyl-m-ethyl-p-phenylenediamine dihydrochloride ((CH$_3$)$_2$NC$_6$H$_4$(CH$_2$CH$_3$)NH$_2$.2HCl, MW 237.17, 1.3 g, 5.5 mmol) was dissolved in water (50 cm$^3$). The pH was adjusted to pH 1.6 using 10% aqueous HCl. A pink colour was formed. Sodium sulphide (Na$_2$S, MW 78.04, 0.71 g, >60%, 5.5 mmol) was added portionwise. An aqueous solution of iron(III) chloride hexahydrate (FeCl$_3$.6H$_2$O, MW 270.30, 2.23 g, 8.2 mmol) in water (50 cm$^3$) was added to the mixture. There was an immediate colour change to purple. The mixture was then aerated for 1 hour. A second aqueous solution of iron(III) chloride hexahydrate (FeCl$_3$.6H$_2$O, MW 270.30, 2.23 g, 8.2 mmol) in water (50 cm$^3$) was added to the mixture. The solution was cooled to 5° C. The mixture was filtered. The residue was washed with water. The filtrate was collected. Sodium chloride (NaCl, MW 57.96, 50 g, 0.86 mol) was added to the filtrate. The mixture was stirred for 10 minutes. The colour changed to red/purple as a precipitate was formed. The mixture was filtered and the solid residue collected. The solid was dissolved in dichloromethane (CH$_2$CH$_2$, 100 cm$^3$) and methanol (CH$_3$OH, 10 cm$^3$) and dried over magnesium sulfate (MgSO$_4$). The mixture was filtered, and the filtrate concentrated to give the product, 1,9-diethyl methylthioninium chloride (DEMTC) (MW 375.96, 0.15 g, 0.40 mmol, 15%) as a green solid. $^6$H (250 MHz; D$_2$O): 6.55 (2H, s, ArH), 6.23 (2H, s, ArH), 2.92 (12H, s, NCH$_3$), 2.56 (4H, q, 7.5, CH$_2$), 0.99 (6H, t, 7.5, CH$_3$).

Flash column chromatography may be performed in order to remove residual iron chloride, using, for example, an eluent of 10% methanol:90% dichloromethane with silica 40-63 μm 60 Å.

Example 20

Ethylthioninium Chloride (ETC) Zinc Chloride (Double Salt) Synthesis Using Manganese Dioxide A stirred mixture of N,N-diethyl-p-phenylenediamine ((CH$_3$CH$_2$)NC$_6$H$_4$NH$_2$, MW 164.25, 5.0 g, 30.4 mmol) in H$_2$O (100 cm$^3$) and sulfuric acid (H$_2$SO$_4$, concentrated, "98%", 1 cm$^3$) was treated with non-reducing zinc chloride solution (ZnCl$_2$, MW 136.29, 7.60 g, 55 mmol, in 15 cm$^3$ of H$_2$O with Na$_2$Cr$_2$O$_7$.2H$_2$O, MW 298.00, 100 mg, 0.3 mmol) to produce a reddish reaction mixture.

Additions of a solution of Al$_2$(SO$_4$)$_3$.16H$_2$O (5.80 g, 9.2 mmol) in H$_2$O (10 cm$^3$); a solution of sodium thiosulfate pentahydrate (Na$_2$S$_2$O$_3$.5H$_2$O, MW 248.18, 8.0 g, 32.2 mmol) in H$_2$O (10 cm$^3$); and one-third of a solution of sodium dichromate dihydrate (Na$_2$Cr$_2$O$_7$.2H$_2$O, MW 298.00, 8.7 g, 29.2 mmol) in H$_2$O (15 cm$^3$) were followed by a rapid rise in temperature to 40° C.

A solution of N,N-diethylaniline ((CH$_3$CH$_2$)$_2$NC$_6$H$_5$, MW 149.24, 3.0 g, 20.1 mmol) in concentrated HCl (4 cm$^3$) was added, followed by addition of the remaining sodium dichromate dihydrate solution. A dark green precipitate was formed. The temperature was rapidly increased to 75° C. A slurry of activated manganese dioxide (MnO$_2$, MW 86.94, 3.80 g, 43.7 mmol) in H$_2$O (5 cm$^3$) was added. The temperature was increased to 85° C. The mixture was stirred at that temperature for 30 minutes. A blue solution with precipitate was observed.

The mixture was cooled to 50° C. and concentrated sulfuric acid (H$_2$SO$_4$, 11 cm$^3$) was slowly added. The mixture was cooled to 20° C. The mixture was vacuum filtered. The residue was collected, and washed with brine (saturated aqueous sodium chloride, NaCl). The black residue was re-dissolved in H$_2$O (250 cm$^3$) at 100° C., cooled to room temperature and vacuum filtered to remove insolubles. The filtrate was treated with zinc chloride (ZnCl$_2$, MW 136.28, 4 g, 29 mmol) and sodium chloride (NaCl, MW 58.44, 23 g, 0.4 mol) and left to stand in a refrigerator for 16 hours. The resulting precipitate was recovered by vacuum filtration, washed with brine (saturated aqueous sodium chloride, NaCl, 30 cm$^3$) and dried in a vacuum oven for 3 hour to give the product, ethylthioninium chloride (ETC) zinc chloride (double salt) (MW 547.70, 5.7 g, 10 mmol, 71%) as a rusty red powder. $\delta_H$ (250 MHz, D$_2$O): 1.20 (12H, br t, CH$_3$), 3.50 (8H, br q, CH$_2$), 6.80 (2H, s, Ph), 7.05 (2H, br d, Ph) and 7.30 (2H, br d, Ph).

Example 21

Quantitative Analysis of Metals Comparison of Obtained Product with Urolene Blue®

Quantitative analysis was performed on a commercially obtained sample of Urolene Blue® as well as a sample of the high purity MTC product obtained using the methods described herein. MTC ("Obtained Product") was obtained by nitrosylation of N,N-dimethylaniline, followed by nitrosyl reduction, thiosulphonic acid formation, oxidative coupling, Cr(VI) reduction using hydrosulfite, ring closure, and chloride salt formation using cold NaCl. This gave crude MTC, which was further purified by sodium sulphide treatment, followed by chloride salt formation using cold NaCl. Analysis was performed using inductively coupled plasma-mass spectrometry (ICP-MS) (using an Agilent 7500® instrument, with and without reaction cell mode (H$_2$)). Samples were prepared according to the standard sample preparation protocol. 10 ppb rhodium was used as an internal standard. The data are summarized in the following table.

TABLE 3

| Metal | Detection Limit (µg/g) | Urolene Blue ® (µg/g) | Obtained Product (µg/g) | European Safety Limits (µg/g) |
|---|---|---|---|---|
| Mg | 0.85 | 585 | 3.5 | — |
| Al | 0.98 | 1939 | 5.0 | 100 |
| Ti | 0.13 | 1331 | 4.2 | — |
| V | 0.08 | 0.5 | <0.08 | — |
| Cr | 0.59 | 10.2 | 2.6 | 10 |
| Mn | 0.06 | 5.2 | <0.06 | 10 |
| Fe | 0.41 | 132 | 6.8 | 100 |
| Cu | 0.47 | 34.4 | 4.4 | 10 |
| Zn | 0.35 | 0.9 | 4.6 | 10 |
| As | 0.22 | 0.9 | <0.22 | — |
| Sr | 0.72 | 104 | <0.72 | — |
| Sn | 0.68 | <0.68 | <0.68 | 1 |
| Pb | 0.07 | 0.3 | 2.4 | 10 |
| U | 0.01 | 0.5 | <0.01 | — |

In addition, the following elements were also detected in Urolene Blue®, but were not detected in the high purity MTC product obtained using the methods described herein: scandium, bromine, yttrium, niobium, palladium, lanthanum, neodymium, samarium, gadolinium, terbium, dysprosium, holmium, erbium, thulium, ytterbium, lutetium, hafnium, tantalum, thorium.

As can be seen from the data, Urolene Blue® exceeds (and in some cases, greatly exceeds) the European safety limits for several metals, including Al, Cr, Fe, Cu, whereas the high purity MTC product obtained using the methods described herein not only meet these standards, but have substantially lower levels of these and other metals.

Example 22

Analysis of Synthesized and Purified MTC

MTC was synthesized and purified according to the methods described herein. The resulting product was analysed for both organic and metal purity. The results are summarised in the following Tables.

TABLE 4

Organic Purity of Synthesized and Purified MTC Determined by HPLC Analysis

| MTC Source | Recrystallisation | MTC % | Azure B % | MVB % | Others % |
|---|---|---|---|---|---|
| Medex ™ | n/a | 94.22 | 5.20 | 0.11 | 0.47 |
| Urolene Blue ® | n/a | 94.27 | 5.23 | 0.09 | 0.41 |
| NTP | n/a | 94.33 | 5.13 | 0.13 | 0.41 |
| DJPS12a | H$_2$O/HCl, pH 1 | 96.37 | 3.07 | 0.15 | 0.07 |
| DJPS13a | H$_2$O/HCl, pH 1 | 96.85 | 2.73 | 0.15 | 0.27 |

Notes:
(1) Medex ™ obtained from Medex Medical Export Co. Ltd.
(2) Urolene Blue ® (MTC formulated as sugar-coated tablets) obtained from Star Pharmaceuticals, Florida, USA.
(3) NTP is an MTC sample from the National Toxicology Program.
(4) DJPS12a & DJPS13a are MTC obtained by nitrosylation of N,N-dimethylaniline, followed by nitrosyl reduction, thiosulphonic acid formation, oxidative coupling, Cr(VI) reduction using hydrosulfite, ring closure, and chloride salt formation using hot NaCl. This gave the crude MTC, which was further purified by cold sodium sulphide treatment, followed by DCM wash, and then cool acidic recrystallisation. There was no residual MTC salted out by NaCl for the samples DJPS12a and DJPS13a.

TABLE 5

ICP-MS Analysis of Metal Contaminants of MTC Samples from Commercial Sources

| | European Pharmacopoeia Limits (ug/g) | | | | |
|---|---|---|---|---|---|
| | Ni | Mo | Cd | Sn | Pb |
| | 10 | 10 | 1 | 1 | 10 |

| # | MTC Source | Metal Content (ug/g) | | | | |
|---|---|---|---|---|---|---|
| 1 | Medex ™ | <0.65 | <0.47 | <0.12 | <0.90 | 1.0 |
| 2 | Urolene Blue ® | 1.0 | 0.30 | <0.03 | <0.68 | 0.3 |
| 3 | NTP | <0.71 | <0.30 | <0.06 | <0.37 | 0.6 |
| 5 | DJPS12a | <0.80 | <0.21 | <0.12 | <0.39 | <0.23 |
| 6 | DJPS13a | <0.80 | <0.21 | <0.12 | <0.39 | <0.23 |

| | European Pharmacopoeia Limits (ug/g) | | | | | |
|---|---|---|---|---|---|---|
| | Al | Cr | Zn | Cu | Fe | Mn |
| | 100 | 10 | 10 | 10 | 100 | 10 |

| # | MTC Source | Metal Content (ug/g) | | | | | |
|---|---|---|---|---|---|---|---|
| 1 | Medex ™ | 8.0 | 125 | <1.25 | 269 | 92.2 | <0.17 |
| 2 | Urolene Blue ® | 1939 | 10.2 | 0.9 | 34.4 | 132 | 5.2 |
| 3 | NTP | 3.4 | 30.1 | <1.0 | 202 | 58.7 | 0.8 |
| 5 | DJPS12a | <0.75 | 1.5 | <1.05 | 2.5 | 16.8 | <0.07 |
| 6 | DJPS13a | <0.75 | 1.4 | <1.05 | <0.68 | <0.32 | <0.07 |

Note that "<" indicates the detection limit of instrument on the day that the analysis was performed.

Note that, unlike the commercial products, the MTC synthesized and purified according to the methods described herein had substantially reduced organic impurity levels, and had metal levels that are less than the EP limits for each of the 11 EP metals.

Example 23

Analysis of Commercially Available MTC Products

Purity data for a range of MTC products obtained from commercial sources are shown in the following tables. Even the Chemical Reference Substance, although relatively organically pure, is relatively impure in regard to metals, and fails to meet the European Pharmacopoeia (EP) standards for copper and chromium.

TABLE 6

HPLC Analysis of Organic Constituents of MTC Samples from Commercial Sources

| # | MTC Source | MTC % | Azure B % | MVB % | Others % |
|---|---|---|---|---|---|
| 1 | Medex ™ | 94.22 | 5.20 | 0.11 | 0.47 |
| 2 | Urolene Blue ® | 94.27 | 5.23 | 0.09 | 0.41 |
| 3 | NTP | 94.33 | 5.13 | 0.13 | 0.41 |
| 4 | Simpson | 95.22 | 4.38 | 0.15 | 0.06 |
| 5 | Martindale | 93.34 | 5.91 | 0.16 | 0.09 |
| 6 | Garuda | 93.72 | 5.74 | 0.12 | 0.09 |
| 7 | Tianjin | 91.15 | 7.52 | 0.21 | 0.28 |
| 8 | Jonas | 94.16 | 4.65 | 0.92 | 0.06 |
| 9 | Amresco | 94.69 | 4.73 | 0.10 | 0.11 |
| 10 | MTC CRS | 96.06 | 3.59 | 0.09 | 0.08 |
| 11 | Aldrich | 94.26 | 5.20 | 0.10 | 0.11 |

Note that all of the commercial products failed to meet the European Pharmacopoeia (EP) limits for copper. Most fail for Chromium. Many fail for aluminium, zinc, and iron. Several fail for other metals, such as nickel, tin, and lead. Many only just meet the EP limits for iron and manganese. Urolene Blue® failed to meet the EP limits for each of copper, chromium, aluminium, and iron.

Note that, additionally, Medex™ contained both iodine and bromine above the detection limit; and that Urolene Blue® also contained high levels of magnesium, titanium, and strontium and levels above the detection limit for uranium, scandium, bromine, yttrium, niobium, palladium, iodine, caesium, lanthanum, cerium, neodymium, samarium, europium, gadolinium, terbium, dysprosium, holmium, thulium, ytterbium, lutetium, hafnium, tantalum, tungsten, and thorium.

Details regarding the MTC Samples from Commercial Sources are set out in the following table.

TABLE 7

ICP-MS Analysis of Metal Contaminants of MTC Samples from Commercial Sources

| | | European Pharmacopoeia Limits (ug/g) | | | | |
|---|---|---|---|---|---|---|
| | | Ni | Mo | Cd | Sn | Pb |
| | | 10 | 10 | 1 | 1 | 10 |
| # | MTC Source | Metal Content (ug/g) | | | | |
| 1 | Medex ™ | <0.65 | <0.47 | <0.12 | <0.90 | 1.0 |
| 2 | Urolene Blue ® | 1.0 | 0.30 | <0.03 | <0.68 | 0.3 |
| 3 | NTP | <0.71 | <0.30 | <0.06 | <0.37 | 0.6 |
| 4 | Simpson | <4.58 | <0.56 | <0.49 | <3.5 | <2.05 |
| 5 | Martindale | 18.9 | 0.4 | <0.03 | <0.20 | 455.4 |
| 6 | Garuda | <4.58 | <0.56 | <0.49 | <3.5 | <2.05 |
| 7 | Tianjin | <4.58 | <0.56 | <0.49 | <3.5 | <2.05 |
| 8 | Jonas | <4.58 | <0.56 | <0.49 | <3.5 | <2.05 |
| 9 | Amresco | <4.58 | <0.56 | <0.49 | 5.1 | <2.05 |
| 10 | MTC CRS | <0.35 | 0.50 | 0.27 | <0.54 | 1.2 |
| 11 | Aldrich | <4.58 | <0.56 | <0.49 | <3.5 | <2.05 |

| | | European Pharmacopoeia Limits (ug/g) | | | | | |
|---|---|---|---|---|---|---|---|
| | | Al | Cr | Zn | Cu | Fe | Mn |
| | | 100 | 10 | 10 | 10 | 100 | 10 |
| # | MTC Source | Metal Content (ug/g) | | | | | |
| 1 | Medex ™ | 8.0 | 125 | <1.25 | 269 | 92.2 | <0.17 |
| 2 | Urolene Blue ® | 1939 | 10.2 | 0.9 | 34.4 | 132 | 5.2 |
| 3 | NTP | 3.4 | 30.1 | <1.0 | 202 | 58.7 | 0.8 |
| 4 | Simpson | <24.9 | 82.2 | <6.93 | 228.1 | 62.8 | 7.2 |
| 5 | Martindale | 161.0 | 175.1 | 76.4 | 1541 | 309.1 | 5.7 |
| 6 | Garuda | <24.9 | 85.2 | <6.93 | 263.5 | 101.6 | 6.5 |
| 7 | Tianjin | <24.9 | 259.6 | 198.8 | 64.3 | 1.8 mg | 11.2 |
| 8 | Jonas | <24.9 | 3.0 | 204.2 | 70.5 | 27.2 | 6.1 |
| 9 | Amresco | 27.2 | 1.0 mg | <6.93 | 276.1 | 96.1 | 6.0 |
| 10 | MTC CRS | 1.3 | 31.4 | 2.6 | 61.1 | 38.6 | 0.6 |
| 11 | Aldrich | <24.9 | 53.5 | <6.93 | 208.7 | 62.4 | 6.5 |

Note that "<" indicates the detection limit of instrument on the day that the analysis was performed.

TABLE 8

Sources of Commercial MTC Samples

| # | Product | Grade; Batch | Source |
|---|---------|--------------|--------|
| 1 | Medex ™ | Methylene blue USP24; Batch No. 030928 | Medex Medical Export Co., Naseby, Northants, UK |
| 2 | Urolene Blue ® | Star Pharmaceuticals formulation; NDC 0076-0501-03; Lot 033797 | Star Pharmaceuticals Inc., Pompano Beach, Florida, USA |
| 3 | NTP | Methylene blue trihydrate, Sample from the National Toxicology Program (NTP); Sigma Batch No. 68H3728 | RTI International, Research Triangle Park, North Carolina, USA |
| 4 | Simpson | Methylene blue BP73; Batch No. 092002 | Simpsons UK Ltd., Caldicot, Gwent, UK |
| 5 | Martindale | Injectable USP formulation (1% w/v); Lot 507565 | Martindale Pharmaceuticals, Romford, Essex, UK |
| 6 | Garuda | Methylene blue(Table XX); Batch No. 021222 | Garuda Chemicals, Andheri (East), Mumbai, India |
| 7 | Tianjin | Methylene blue, zinc free | Tianjin Sanhuan Chemical Co,. Ltd., Tianjin, China |
| 8 | Jonas | Methylene blue, zinc free; Batch No. 17040 | Jonas Chemical Corp., Brooklyn, NY, USA |
| 9 | Amresco | Methylene blue, Reagent grade; Code 0722; Batch No. 0972B70 | Amresco Inc., Ohio, USA |
| 10 | MTC CRS-EP | Methylthioninium chloride Ph. Eur. CRS; Cat. M1800900; Batch 1 (Chemical Reference Substance) | "European Directorate for the Quality of Medicines", (EDQM) Strasbourg, France |
| 11 | Aldrich | Methylene blue trihydrate, Cat. M44907; Batch No. KU05126C | Sigma-Aldrich Chemical Co., Poole, Dorset, UK |

Example 24

Preparation of Capsules

Gelatin capsules comprising MTC and suitable for pharmaceutical use were prepared.

The drug product was Size 1 blue/blue gelatin capsules containing a greenish/blue waxy material, which is a mixture of the active substance, methylthioninium chloride (MTC) in a waxy suspension with Gelucire 44/14 ((Lauroyl macrogol-32 glycerides PhEur, USP) as the suspension vehicle and 2% Aerosil 200® (Colliodal Silicon Dioxide PhEur, USP) as a thixotropic suspending agent.

Three strengths of capsule are manufactured with target strengths of 30, 60 and 100 mg. A bulk mixture of 25% MTC (on anhydrous basis), 73% Gelucire, and 2% Aerosil 200 was prepared and the dose controlled by variation in fill weight with the formulation composition being constant for each dose.

The capsules were manufactured to cGMP by MW Encap Ltd (also known as Encap Drug Delivery), West Lothian, UK. A typical batch formula is shown in the following Table.

TABLE 10

Typical Batch Formula

| Raw Material | Batch Quantity |
|--------------|----------------|
| MTC | 1.25 kg |
| Gelucire 44/14 ® | 5.00 kg |
| Aerosil 200 ® | 100 g |
| Size 1 capsules opaque dark blue | Min 20,000 |
| Gelatin | 1 kg (excess) |
| Purified water | 3 litres (excess) |

The Gelucire was melted at approximately 65° C. and held at approximately 65° C. in the mixing vessel. The MTC (screened through a 600 μm sieve) and Aerosil 200® were

TABLE 9

Capsule Content

| Name of Ingredient | Function | Reference | Quantity (per capsule) | | | |
|---|---|---|---|---|---|---|
| | | | 30 mg | 60 mg | 100 mg | Placebo |
| MTC | Active | USP | 30 | 60 | 100 | 0 |
| Gelucire 44/14 ® | Filler | PhEur USP | 117 mg* | 234 mg* | 390 mg* | 300 mg |
| Aerosil 200 ® | Suspending agent | PhEur USP | 3 mg* | 6 mg* | 10 mg* | 0 |

*Nominally.

added and mixed until the mixture was homogeneous. The mixture was degassed by applying a vacuum for approximately 15 minutes and then transferred to the hopper (set at a temperature of approximately 55° C.) of a capsule-filling machine. Hard gelatin capsules (from Capsugel) were filled and the target fill weight checked at frequent intervals (approximately 30 minute intervals). The capsules were then transferred to a banding machine. A gelatin banding solution (gelatin in purified water) was prepared. The capsules were banded on the banding machine with inspection on-line for bubbles and incomplete seals. The capsules were then passed through a drying oven at 25 to 30° C.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as described herein.

The present invention is not limited to those embodiments that are encompassed by the appended claims, which claims pertain to only some of many preferred aspects and embodiments of the invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Badische Anilin-und Soda-Fabrik, 1877, "Verfahren Zur Darstellung Blauer Farbstoffe Aus Dimethyl-Anilin Und Anderen Tertiaren Aromatischen Monaminen," German Patent No. 1886, published 15 Dec. 1877.

Bernthsen, August, 1885a, "Studien in der Methylenblaugruppe," Justus Liebig's Annalen der Chemie, Band 230, pp. 73-136.

Bernthsen, August, 1885b, "Studien in der Methylenblaugruppe," Justus Liebig's Annalen der Chemie, Band 230, pp. 137-211.

Bernthsen, August, 1889, "Studien in der Methylenblaugruppe," Justus Liebig's Annalen der Chemie, Band 251, pp. 1-96.

Colour Index, Vol. 4 (3rd Edition, 1971), p. 4470, Entry Number 52015.

Fierz-David and Blangley, 1949, "F. Oxazine and Thiazine Dyes," in: *Fundamental Processes of Dye Chemistry*, published by Interscience (London, UK), pp. 308-314.

Guttmann P, Ehrlich P. Über die Wirkung des Methylenblau bei Malaria. Berl Klin Wochenschr 1891; 28: 953-956.

Leventis, N., et al., 1997, "Synthesis of Substituted Phenothiazines Analogous to Methylene Blue by Electrophilic and Nucleophilic Aromatic Substitutions in Tandem. A Mechanistic Perspective," Tetrahedron, Vol. 53, No. 29, pp. 10083-10092.

Lillie, R. D., et al., 1979, "Zinc Chloride Methylene Blue, I. Biological Stain History, Physical Characteristics and Approximation of Azure B Content of Commercial Samples," *Stain Technology*, Vol. 54, No. 1, pp. 33-39.

Lohr, W., Grubhoffer, N., Sohmer, I., Wittekind, D., 1975, "The azure dyes: their purification and physiochemical properties. Purification of Azure B," *Stain Technology*, Vol. 50 (3), pp. 149-156.

Marshall, P. N., Lewis, S. M., 1975a, "The purification of Methylene Blue and Azure B by solvent extraction and crystallisation," *Stain Technology*, Vol. 50(6), pp. 375-381.

Marshall, P. N., Lewis, S. M., 1975b, "Metal contaminants in commercial dyes," *Stain Technology*, Vol. 50 (3), pp. 143-147.

Masuya, Hirotomo, 1992, "Phenothiazine Derivatives, Their Production and Use," European Patent Publication No 0 510 668 A2, published 28 Oct. 1992.

Michaelis, L., et al. 1940, "Semiquinone Radicals of the Thiazines," *Journal of the Americal Chemical Society*, Vol. 62, pp. 204-211.

Rengelshausen, J., Burhenne, J., Frohlich, M., Tayrouz, Y., Singh, S. K., Riedel, K.-D., Muller, O., Hoppe-Tichy, T., Haefeli, W. E., Mikus, G. & Walter-Sack, I. (2004) Pharmacokinetic interaction of chloroquine and methylene blue combination against malaria. European Journal of Clinical Pharmacology 60, 709-715.

Schirmer, H., Coulibaly, B., Stich, A., Scheiwein, M., Merkle, H., Eubel, J., Becker, K., Becher, H., Müller, O., Zich, T., Schiek, W. & Kouyaté, B. (2003) Methylene blue as an antimalarial agent. Redox Report 8, 272-275.

Wischik, C. M., et al., 1996, "Inhibition of Tau-Tau-Association," published international (PCT) patent application publication number WO 96/30766 published 3 Oct. 1996.

Wischik, C. M., et al., 2002, "Materials and Methods Relating to Protein Aggregation in Neurodegenerative Disease," published international (PCT) patent application publication number WO 02/055720 published 18 Jul. 2002.

The invention claimed is:

1. A method of synthesis comprising the steps of, in order:

oxidative coupling (OC), in which a thiosulfuric acid S-{2-(amino)-3-(optionally substituted)-5-(disubstituted amino)-phenyl} ester, 4, is oxidatively coupled to an N,N-disubstituted-3-optionally substituted-aniline, 5, using an oxidizing agent that is or comprises Cr(VI), to give a [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6:

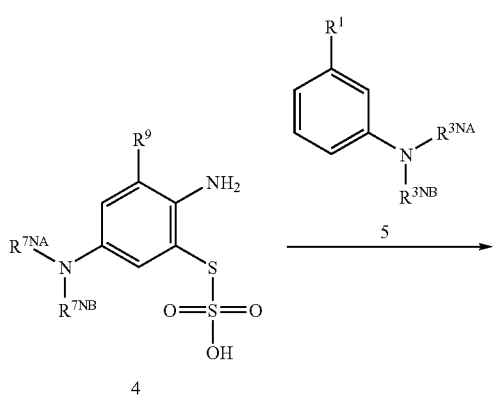

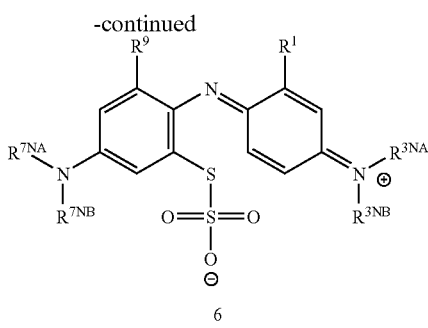

6 isolation and purification of zwitterionic intermediate (IAPOZI), in which said [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, is isolated and purified;

ring closure (RC), in which said isolated and purified [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, is subjected to ring closure to give a 3,7-bis(disubstituted-amino)-1,9-(optionally substituted)-phenothiazin-5-ium salt, 7:

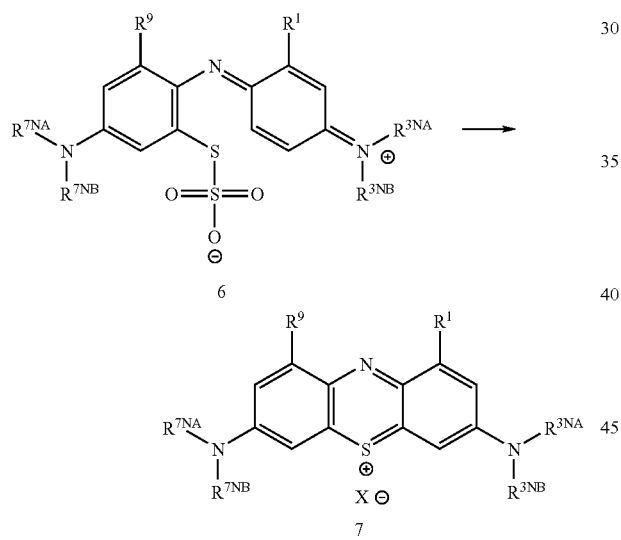

wherein:
each of $R^1$ and $R^9$ is independently selected from: —H; $C_{1-4}$alkyl; $C_{2-4}$alkenyl; and halogenated $C_{1-4}$alkyl;
each of $R^{3NA}$ and $R^{3NB}$ is independently selected from: $C_{1-4}$alkyl; $C_{2-4}$alkenyl; and halogenated $C_{1-4}$alkyl;
each of $R^{7NA}$ and $R^{7NB}$ is independently selected from: $C_{1-4}$alkyl; $C_{2-4}$alkenyl; and halogenated $C_{1-4}$alkyl; and
X is one or more anionic counter ions to achieve electrical neutrality.

2. A method of synthesis according to claim 1, wherein said oxidizing agent for said oxidative coupling (OC) step is $Na_2Cr_2O_7$.

3. A method of synthesis according to claim 1 wherein said oxidative coupling (OC) step is performed under acidic conditions.

4. A method of synthesis according to claim 1, wherein said isolation and purification is by filtration.

5. A method of synthesis according to claim 1, wherein said isolation and purification is by filtration followed by washing.

6. A method of synthesis according to claim 1, wherein said isolation and purification is by filtration followed by washing and drying.

7. A method of synthesis according to claim 1, wherein said ring closure (RC) step is achieved by treatment with Cu(II) sulfate.

8. A method of synthesis according to claim 1, wherein said ring closure (RC) step is performed under acidic conditions.

9. A method of synthesis according to claim 1, further comprising, following said oxidative coupling (OC) step, and preceding said isolation and purification of zwitterionic intermediate (IAPOZI) step, the additional step of:
Cr(VI) Reduction (CR), in which the product of the oxidative coupling (OC) step is treated to convert residual Cr(VI) to Cr(III).

10. A method of synthesis according to claim 9, wherein said treatment to convert residual Cr(VI) to Cr(III) is treatment with a reducing agent.

11. A method of synthesis according to claim 9, wherein said treatment to convert residual Cr(VI) to Cr(III) is treatment with a hydrosulfite.

12. A method of synthesis according to claim 9, wherein said treatment to convert residual Cr(VI) to Cr(III) is treatment with sodium hydrosulfite.

13. A method of synthesis according to claim 9, wherein said treatment to convert residual Cr(VI) to Cr(III) is treatment with an alkanol.

14. A method of synthesis according to claim 9, wherein said treatment to convert residual Cr(VI) to Cr(III) is treatment with an iodide.

15. A method of synthesis according to claim 9, wherein said treatment to convert residual Cr(VI) to Cr(III) is treatment with an acid or a base to achieve a pH of 5.70 to 6.35.

16. A method of synthesis according to claim 1, further comprising, before said oxidative coupling (OC) step, the additional step of:
thiosulfonic acid formation (TSAF), in which an N,N-disubstituted-1,4-diamino-5-optionally substituted benzene, 3, is oxidized in the presence of a thiosulfate to give said thiosulfuric acid S-{2-(amino)-3-(optionally substituted)-5-(disubstituted-amino)-phenyl} ester, 4:

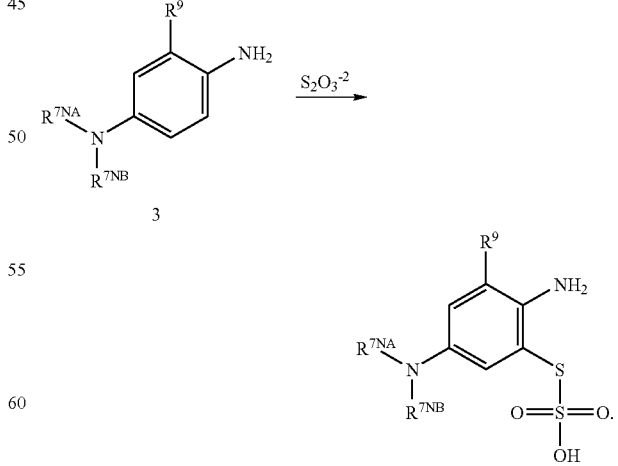

17. A method of synthesis according to claim 16, wherein said thiosulfate is or comprises $Na_2S_2O_3$.

18. A method of synthesis according to claim 16, wherein said oxidation in said thiosulfonic acid formation (TSAF) step is by reaction with an oxidizing agent that is or comprises Cr(VI).

19. A method of synthesis according to claim 16, wherein said oxidation in said thiosulfonic acid formation (TSAF) step is is by reaction with an oxidizing agent that is or comprises $Na_2Cr_2O_7$.

20. A method of synthesis according to claim 16, further comprising, before said thiosulfonic acid formation (TSAF) step, the additional step of:
nitrosyl reduction (NR), in which an N,N-disubstituted-3-optionally substituted-4-nitrosyl aniline, 2, is reduced to form said N,N-disubstituted-1,4-diamino-5-optionally substituted benzene, 3:

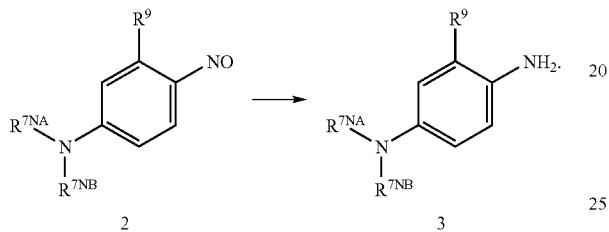

21. A method of synthesis according to claim 20, wherein said reduction in said nitrosyl reduction (NR) step is by reaction with a reducing agent that is or comprises Fe(O).

22. A method of synthesis according to claim 20, wherein said reduction in said nitrosyl reduction (NR) step is by reaction with a reducing agent that is or comprises metallic iron.

23. A method of synthesis according to claim 20, wherein said reduction in said nitrosyl reduction (NR) step is performed in under acidic conditions.

24. A method of synthesis according to claim 20, further comprising, before said nitrosyl reduction (NR) step, the additional step of:
nitrosylation (NOS), in which an N,N-disubstituted-3-optionally substituted aniline, 1, is 4-nitrosylated to give said N,N-disubstituted-3-optionally substituted-4-nitrosyl aniline, 2:

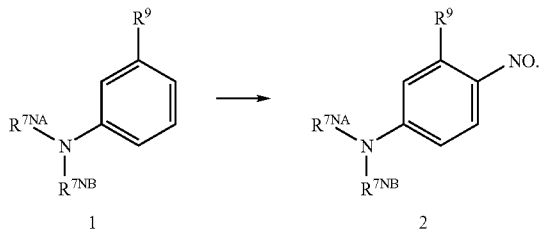

25. A method of synthesis according to claim 24, wherein said nitrosylation is performed using a nitrite.

26. A method of synthesis according to claim 24, wherein said nitrosylation is performed using a sodium nitrite.

27. A method of synthesis according to claim 24, wherein said nitrosylation is performed under acidic conditions.

28. A method of synthesis according to claim 1, further comprising, after said ring closure (RC) step, the additional step of:
chloride salt formation (CSF), in which said 3,7-bis(disubstituted-amino)-1,9-(optionally substituted)-phenothiazin-5-ium salt, 7, is reacted with chloride, to give a 3,7-bis(disubstituted-amino)-1,9-(optionally substituted)-phenothiazin-5-ium chloride salt, 8:

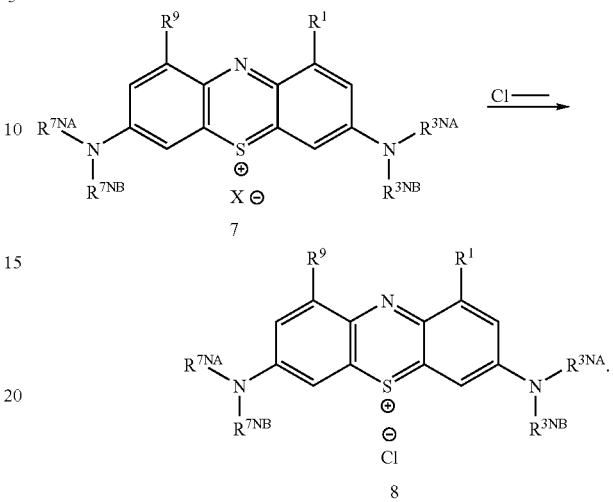

29. A method of synthesis according to claim 28, wherein the chloride is hydrochloric acid.

30. A method of synthesis according to claim 29, wherein chloride salt formation (CSF) is performed at a relatively low pH of 0 to 2.

31. A method of synthesis according to claim 29, wherein chloride salt formation (CSF) is performed at a relatively cool temperature of 0 to 30° C.

32. A method of synthesis according to claim 28, wherein said chloride is sodium chloride.

33. A method of synthesis according to claim 28, further comprising, after said chloride salt formation (CSF) step, the additional step of:
sulphide treatment (ST), in which said 3,7-bis(disubstituted-amino)-1,9-(optionally substituted)-phenothiazin-5-ium chloride salt, 8, is treated with a sulphide.

34. A method of synthesis according to claim 33, wherein said sulphide is a metal sulphide.

35. A method of synthesis according to claim 34, wherein said sulphide is sodium sulphide.

36. A method of synthesis according to claim 33, wherein sulphide treatment (ST) is performed at a temperature of 5 to 15° C.

37. A method of synthesis according to claim 33, wherein the sulphide treatment (ST) is performed at a pH of 9 to 12.

38. A method of synthesis according to claim 33, wherein said treatment with a sulphide is treatment with a sulphide, followed by washing with an organic solvent.

39. A method of synthesis according to claim 33, wherein said treatment with a sulphide is treatment with a sulphide, followed by washing with an organic solvent, followed by treatment with a chloride.

40. A method of synthesis according to claim 33, wherein said treatment with a sulphide is treatment with a sulphide, followed by washing with an organic solvent, followed by adjusting the pH to about 4.5 to about 5.5, followed by treatment with a chloride.

41. A method of synthesis according to claim 38, wherein said organic solvent is dichloromethane.

42. A method of synthesis according to claim 28, further comprising, after said chloride salt formation (CSF) step, the additional step of:
dimethyldithiocarbamate treatment (DT), in which said 3,7-bis(disubstituted-amino)-1,9-(optionally substituted)-phenothiazin-5-ium chloride salt, 8, is treated with a dimethyldithiocarbamate.

43. A method of synthesis according to claim 28, further comprising, after said chloride salt formation (CSF) step, the additional step of:
carbonate treatment (CT), in which said 3,7-bis(disubstituted-amino)-1,9-(optionally substituted)-phenothiazin-5-ium chloride salt, 8, is treated with a carbonate.

44. A method of synthesis according to claim 28, further comprising, after said chloride salt formation (CSF) step, the additional step of:
ethylenediaminetetraacetic acid treatment (EDTAT), in which said 3,7-bis(disubstituted-amino)-1,9-(optionally substituted)-phenothiazin-5-ium chloride salt, 8, is treated with ethylenediaminetetraacetic acid (EDTA) or an EDTA salt.

45. A method of synthesis according to claim 28, further comprising the subsequent additional step of:
organic extraction (OE), in which said 3,7-bis(disubstituted-amino)-1,9-(optionally substituted)-phenothiazin-5-ium chloride salt, 8, in aqueous solution or suspension, is treated with an organic solvent.

46. A method of synthesis according to claim 45, wherein said organic solvent is dichloromethane ($CH_2Cl_2$, DCM).

47. A method of synthesis according to claim 45, wherein the treatment with an organic solvent is performed iteratively using a plurality of aliquots of the organic solvent.

48. A method of synthesis according to claim 45, wherein the aqueous solution or suspension of salt, 8, has a pH of 9 to 12.

49. A method of synthesis according to claim 45, wherein the treatment with an organic solvent is performed at a temperature of 5 to 15° C.

50. A method of synthesis according to claim 28, further comprising the additional final step of:
recrystallisation (RX), in which said 3,7-bis(disubstituted-amino)-1,9-(optionally substituted)-phenothiazin-5-ium chloride salt, 8, is recrystallised.

51. A method of synthesis according to claim 50, wherein said recrystallisation is recrystallisation from water at a relatively cool temperature of 2 to 40° C. by adjusting the pH to a relatively low pH of −1 to 3.

52. A method of synthesis according to claim 51, wherein the relatively cool temperature is 10 to 30° C.

53. A method of synthesis according to claim 51, wherein the relatively cool temperature is about 25° C.

54. A method of synthesis according to claim 51, wherein the relatively low pH is 0 to 2.

55. A method of synthesis according to claim 51, wherein the relatively low pH is about 1.

56. A method of synthesis according to claim 50, wherein said recrystallisation is recrystallisation from water at an initial elevated temperature, in the presence of a chloride.

57. A method of synthesis according to claim 1, comprising the steps of, in order:
nitrosylation (NOS), in which an N,N-disubstituted-3-optionally substituted aniline, 1, is 4-nitrosylated to give said N,N-disubstituted-3-optionally substituted-4-nitrosyl aniline, 2:

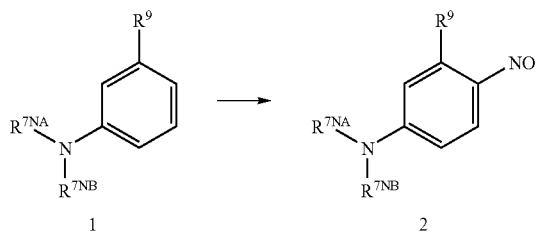

nitrosyl reduction (NR), in which an N,N-disubstituted-3-optionally substituted-4-nitrosyl aniline, 2, is reduced to form said N,N-disubstituted-1,4-diamino-5-optionally substituted benzene, 3:

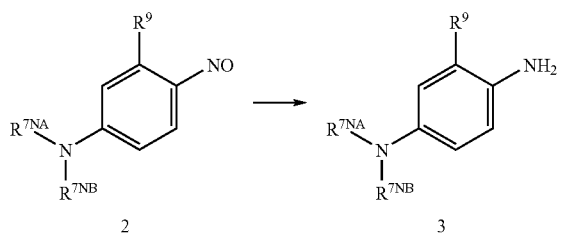

thiosulfonic acid formation (TSAF), in which an N,N-disubstituted-1,4-diamino-5-optionally substituted benzene, 3, is oxidized in the presence of a thiosulfate to give said thiosulfuric acid S-{2-(amino)-3-(optionally substituted)-5-(disubstituted-amino)-phenyl} ester, 4:

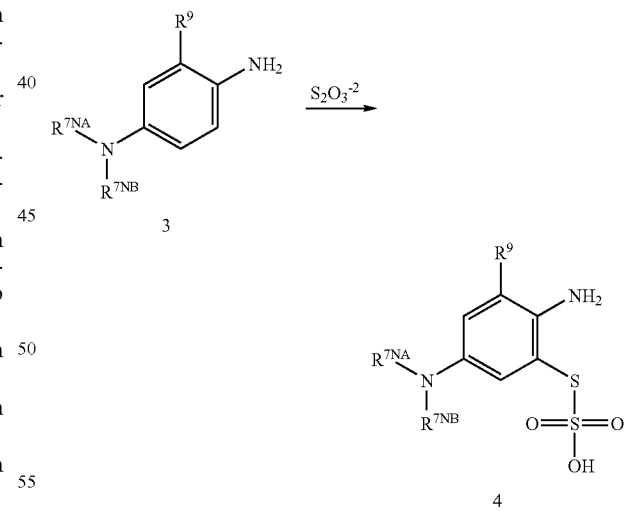

oxidative coupling (OC), in which a thiosulfuric acid S-{2-(amino)-3-(optionally substituted)-5-(disubstituted amino)-phenyl} ester, 4, is oxidatively coupled to an N,N-disubstituted-3-optionally substituted-aniline, 5, using an oxidizing agent that is or comprises Cr(VI), to give a [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6:

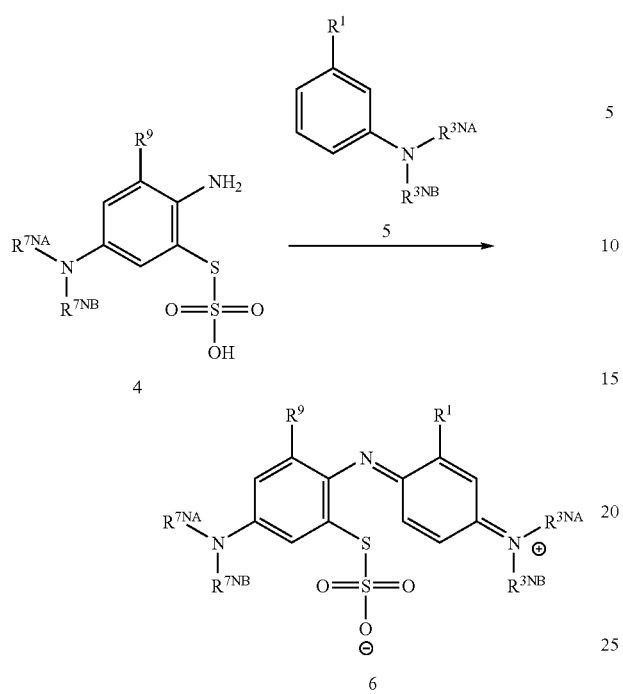

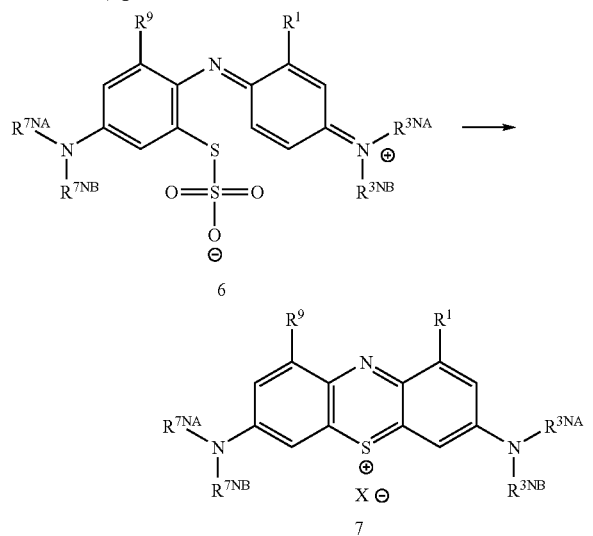

Cr(VI) Reduction (CR), in which the product of the oxidative coupling (OC) step is treated to convert residual Cr(VI) to Cr(III). isolation and purification of zwitterionic intermediate (IAPOZI), in which said [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, is isolated and purified;

ring closure (RC), in which said isolated and purified [4-{2-(thiosulfate)-4-(disubstituted amino)-6-(optionally substituted)-phenyl-imino}-3-(optionally substituted) -cyclohexa-2,5-dienylidene]-N,N-disubstituted ammonium, 6, is subjected to ring closure to give a 3,7-bis(disubstituted-amino)-1,9-(optionally substituted)-phenothiazin-5-ium salt, 7:

chloride salt formation (CSF), in which said 3,7-bis(disubstituted-amino)-1,9-(optionally substituted)-phenothiazin-5-ium salt, 7, is reacted with chloride, to give a 3,7-bis(disubstituted-amino)-1,9-(optionally substituted)-phenothiazin-5-ium chloride salt, 8:

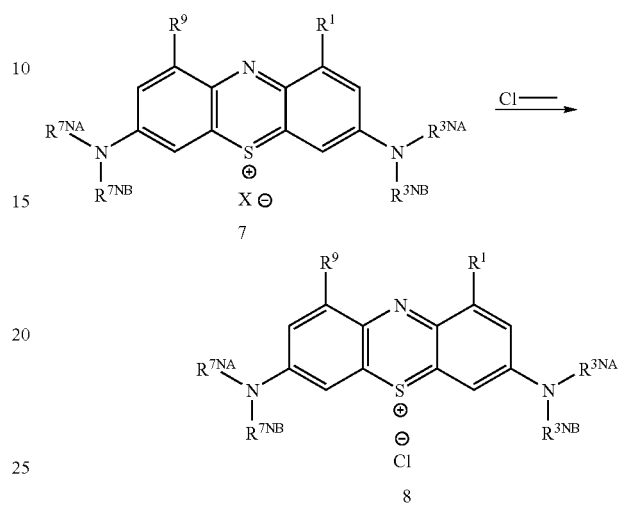

sulphide treatment (ST), in which said 3,7-bis(disubstituted-amino)-1,9-(optionally substituted)-phenothiazin-5-ium chloride salt, 8, is treated with a sulphide;

organic extraction (OE), in which said 3,7-bis(disubstituted-amino)-1,9-(optionally substituted)-phenothiazin-5-ium chloride salt, 8, in aqueous solution or suspension, is treated with an organic solvent;

recrystallisation (RX), in which said 3,7-bis(disubstituted-amino)-1,9-(optionally substituted)-phenothiazin-5-ium chloride salt, 8, is recrystallised;

wherein:

each of $R^1$ and $R^9$ is independently selected from: —H; $C_{1-4}$alkyl; $C_{2-4}$alkenyl; and halogenated $C_{1-4}$alkyl;

each of $R^{3NA}$ and $R^{3NB}$ is independently selected from: $C_{1-4}$alkyl; $C_{2-4}$alkenyl; and halogenated $C_{1-4}$alkyl;

each of $R^{7NA}$ and $R^{7NB}$ is independently selected from: $C_{1-4}$alkyl; $C_{2-4}$alkenyl; and halogenated $C_{1-4\ alkyl}$; and X is one or more anionic counter ions to achieve electrical neutrality.

58. A method of synthesis according to claim 57, wherein said organic solvent is dichloromethane ($CH_2Cl_2$, DCM).

59. A method of synthesis according to claim 57, wherein said recrystallisation is recrystallisation from water at a relatively cool temperature of 10 to 30° C. by adjusting the pH to a relatively low pH of 0 to 2.

60. A method of synthesis according to claim 50, wherein said recrystallisation includes subsequent drying of the recrystallised precipitate.

* * * * *